US012807683B2

(12) United States Patent
Wang et al.

(10) Patent No.: US 12,807,683 B2
(45) Date of Patent: Nov. 24, 2026

(54) ANTI-SARS-COV-2 SPIKE PROTEIN ANTIBODIES AND METHODS OF USE

(71) Applicant: University of Massachusetts, Westborough, MA (US)

(72) Inventors: Yang Wang, Wellesley, MA (US); Mark S.J. Klempner, Boston, MA (US); Qi Li, Westwood, MA (US); Monir Ejemel, Medfield, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 863 days.

(21) Appl. No.: 17/923,546

(22) PCT Filed: May 5, 2021

(86) PCT No.: PCT/US2021/030794
§ 371 (c)(1),
(2) Date: Nov. 4, 2022

(87) PCT Pub. No.: WO2021/226179
PCT Pub. Date: Nov. 11, 2021

(65) Prior Publication Data

US 2023/0192820 A1 Jun. 22, 2023

Related U.S. Application Data

(60) Provisional application No. 63/020,483, filed on May 5, 2020.

(51) Int. Cl.

| | |
|---|---|
| ***C07K 16/104*** | (2026.01) |
| ***A61P 31/14*** | (2006.01) |
| ***C07K 16/102*** | (2026.01) |
| ***C12N 15/63*** | (2006.01) |

(52) U.S. Cl.
CPC ............ *C07K 16/104* (2026.01); *A61P 31/14* (2018.01); *C07K 16/102* (2026.01); *C12N 15/63* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 2004/0071694 | A1 | 4/2004 | DeVries et al. | |
| 2011/0114095 | A1 * | 5/2011 | Smith | B01D 39/1692 424/630 |
| 2014/0314784 | A1 | 10/2014 | Bedian et al. | |
| 2014/0322218 | A1 | 10/2014 | Xiao et al. | |

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Dubel (Handbook of Therapeutic Antibodies, 2007, p. 100-101) (Year: 2007).*
Johnson and Wu (Methods in Molecular Biology, Antibody Engineering: Methods and Protocols, vol. 248, p. 11-25, 2004) (Year: 2004).*
Polyak et Al. (Blood, vol. 99, No. 9, p. 3256-3262, 2002) (Year: 2002).*
Munodzana et Al. (Infection and Immunity, vol. 66 No. 6, p. 2619-2624, 1998) (Year: 1998).*
Wall et Al. (Theriogenology, vol. 45, p. 57-68, 1996) (Year: 1996).*
Houdebine et Al., Journal of Biotechnology, vol. 34, p. 269-287, 1994 (Year: 1994).*
Kappell et Al., Current Opinions in Biotechnology, vol. 3, p. 548-553, 1992 (Year: 1992).*
Houdebine (Comparative Immunology, Microbiology, and Infectious Diseases, vol. 32, p. 107-121, 2009) (Year: 2009).*
International Search Report and Written Opinion for PCT/US2021/030794, mailed Oct. 25, 2021 (12 pages).
Wang et al., "A human monoclonal antibody blocking SARS-CoV-2 infection," Nat Commun. 11(1):2251 (May 4, 2020) (6 pages).
Zheng et al., "Novel antibody epitopes dominate the antigenicity of spike glycoprotein in SARS-CoV-2 compared to SARS-CoV," Cell Mol Immunol. 17(5):536-538 (Mar. 4, 2020) (11 pages).
International Preliminary Report of Patentability for International Application No. PCT/US2021/030794, dated Nov. 8, 2022 (8 pages).
Ejemel et al., "A cross-reactive human IgA monoclonal antibody blocks SARS-CoV-2 spike-ACE2 interaction," Nat Commun. 11(1):4198 (Aug. 2020) (9 pages).
Pinto et al., "Cross-neutralization of SARS-CoV-2 by a human monoclonal SARS-CoV antibody," Nature. 583(7815):290-295 (May 2020) (22 pages).

* cited by examiner

*Primary Examiner* — Thomas J. Visone
(74) *Attorney, Agent, or Firm* — Baker, Donelson, Bearman, Caldwell & Berkowitz, PC

(57) ABSTRACT

The invention provides anti-SARS-COV-2 spike(S) protein antibodies and methods of using the same.

15 Claims, 19 Drawing Sheets

Specification includes a Sequence Listing.

SARS-CoV RBD ($S_{270-510}$)

SARS-CoV-2 RBD ($S_{319-541}$)

MAb362 (SARS2)

SARS2 RBD (MAb362)

SARS2 RBD(ACE2)

| | ELISA EC50 (µg mL$^{-1}$) | Fold change to WT |
|---|---|---|
| Wild type | 0.64 | 1.00 |
| Y449A | 2.03 | 3.18 |
| Y453A | 64.31 | 100.69 |
| L455K | 0.27 | 0.42 |
| A456A | 4.00 | 6.26 |
| A475W | 6.59 | 10.32 |
| F486A | 0.48 | 0.75 |
| N487K | 0.63 | 0.99 |
| Y489A | 13.04 | 20.42 |
| Q493W | 4.54 | 7.11 |
| Q496K | 0.21 | 0.33 |
| Q498A | 0.21 | 0.33 |
| T500A | 0.91 | 1.42 |
| N501A | 0.34 | 0.52 |
| G502K | 0.18 | 0.28 |
| Y505A | 0.42 | 0.65 |

SARS-CoV-2 RBD (Mab362)

SARS-CoV-2 RBD

| Antibody | MAb362 IgG | MAb362 IgA | MAb362 dIgA | MAb362 sIgA |
| --- | --- | --- | --- | --- |
| IC50 ($\mu g\ mL^{-1}$) | 1.56 | 0.84 | 0.63 | 0.94 |

| Antibody | MAb362 IgG | MAb362 IgA | MAb362 dIgA | MAb362 sIgA |
|---|---|---|---|---|
| IC50 ($\mu g\ mL^{-1}$) | 58.67 | 1.26 | 0.03 | 0.01 |

| Antibody | MAb362 IgG | MAb362 sIgA |
|---|---|---|
| IC50 (µg mL$^{-1}$) | >50 | 9.54 ± 5.88 |

Fig. 13A
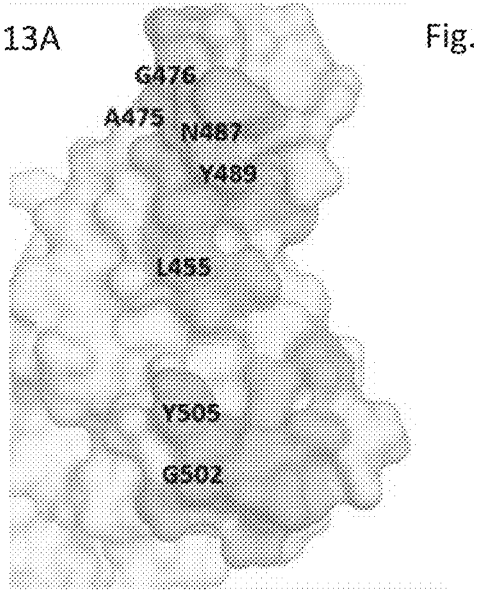
SARS-CoV-2 RBD (ACE2)
Fig. 13B
| | $EC_{50}$ (µg mL^-1) | Fold change to WT |
|---|---|---|
| Wild type | 2.88 | 1.00 |
| Y449A | 2.95 | 1.02 |
| Y453A | 3.88 | 1.35 |
| L455K | 45.06 | 15.63 |
| F456A | 2.66 | 0.92 |
| A475W | 20.92 | 7.26 |
| G476W | 16.70 | 5.79 |
| N487K | 22.52 | 7.81 |
| Y489A | 25.27 | 8.77 |
| Q493W | 1.19 | 0.41 |
| G496K | 9.66 | 3.35 |
| Q498A | 0.29 | 0.10 |
| T500A | 2.86 | 0.99 |
| N501A | 2.61 | 0.91 |
| G502K | 41.62 | 14.44 |
| Y505A | 33.75 | 11.71 |
Fig. 13C
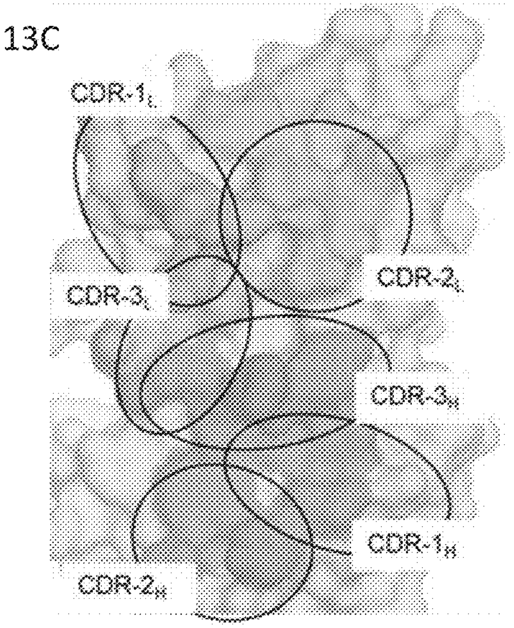
MAb362 (SARS-CoV-2 RBD)

SEQUENCE LISTING

```
<160> NUMBER OF SEQ ID NOS: 21

<210> SEQ ID NO 1
<211> LENGTH: 1273
<212> TYPE: PRT
<213> ORGANISM: Betacoronavirus SARS-CoV-2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160
```

```
Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575
```

-continued

```
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
```

```
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Gly Phe Ser Phe Ser Ser Tyr Gly Met His
1               5                   10


<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3
```

Trp Tyr Asp Gly Ser Asp Lys
1 5

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Ala Arg Glu Arg Tyr Phe Asp Trp Ile Phe Asp Phe
1 5 10

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct

<400> SEQUENCE: 5

Arg Ala Ser Gln Ser Val Ser Ser Ser Tyr Leu Ala
1 5 10

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Gly Ala Ser Ser Arg Ala Thr
1 5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Gln Gln Tyr Gly Ser Ser Trp Thr
1 5

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Glu Ser Gly Gly Gly Val Val Gln Pro Gly Arg
1 5 10 15

Ser Leu Arg Leu Ser Cys Ala Ala Ser
20 25

<210> SEQ ID NO 9
<211> LENGTH: 16
<212> TYPE: PRT
<213> ORGANISM: Artificial Sequence
<220> FEATURE:
<223> OTHER INFORMATION: Synthetic Construct

<400> SEQUENCE: 9

Trp Val Arg Gln Ala Pro Gly Lys Gly Leu Glu Trp Val Ala Val Ile
1 5 10 15

<210> SEQ ID NO 10
<211> LENGTH: 38
<212> TYPE: PRT
<213> ORGANISM: Artificial Sequence
<220> FEATURE:
<223> OTHER INFORMATION: Synthetic Construct

<400> SEQUENCE: 10

Tyr Tyr Ala Asp Ser Val Lys Gly Arg Phe Thr Ile Ser Arg Asp Asn
1 5 10 15

Ser Lys Asn Thr Leu Tyr Leu Gln Leu Asn Ser Leu Arg Ala Glu Asp
20 25 30

Thr Ala Ile Tyr Tyr Cys
35

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Trp Gly Gln Gly Thr Leu Val Thr Val Ser Ser
1 5 10

<210> SEQ ID NO 12
<211> LENGTH: 23
<212> TYPE: PRT
<213> ORGANISM: Artificial Sequence
<220> FEATURE:
<223> OTHER INFORMATION: Synthetic Construct

<400> SEQUENCE: 12

Glu Ile Val Leu Thr Gln Ser Pro Gly Thr Leu Ser Leu Ser Pro Gly
1 5 10 15

Glu Arg Ala Thr Leu Ser Cys
20

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Trp Tyr Gln Gln Lys Pro Gly Gln Ala Pro Arg Leu Leu Ile Tyr
1 5 10 15

<210> SEQ ID NO 14
<211> LENGTH: 32
<212> TYPE: PRT
<213> ORGANISM: Artificial Sequence
<220> FEATURE:
<223> OTHER INFORMATION: Synthetic Construct

<400> SEQUENCE: 14

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Phe Gly Gln Gly Thr Lys Val Glu Ile Lys
1 5 10

<210> SEQ ID NO 16
<211> LENGTH: 119
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asp Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Leu Asn Ser Leu Arg Ala Glu Asp Thr Ala Ile Tyr Tyr Cys
85 90 95

Ala Arg Glu Arg Tyr Phe Asp Trp Ile Phe Asp Phe Trp Gly Gln Gly
100 105 110

Thr Leu Val Thr Val Ser Ser
115

<210> SEQ ID NO 17
<211> LENGTH: 107
<212> TYPE: PRT
<213> ORGANISM: Artificial Sequence
<220> FEATURE:
<223> OTHER INFORMATION: Synthetic Construct

<400> SEQUENCE: 17

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Trp
85 90 95

Thr Phe Gly Gln Gly Thr Lys Val Glu Ile Lys 100 105

<210> SEQ ID NO 18
<211> LENGTH: 1255
<212> TYPE: PRT
<213> ORGANISM: Betacoronavirus SARS-CoV

<400> SEQUENCE: 18

Met Phe Ile Phe Leu Leu Phe Leu Thr Leu Thr Ser Gly Ser Asp Leu
1 5 10 15

Asp Arg Cys Thr Thr Phe Asp Asp Val Gln Ala Pro Asn Tyr Thr Gln
20 25 30

His Thr Ser Ser Met Arg Gly Val Tyr Tyr Pro Asp Glu Ile Phe Arg
35 40 45

Ser Asp Thr Leu Tyr Leu Thr Gln Asp Leu Phe Leu Pro Phe Tyr Ser
50 55 60

Asn Val Thr Gly Phe His Thr Ile Asn His Thr Phe Gly Asn Pro Val
65 70 75 80

Ile Pro Phe Lys Asp Gly Ile Tyr Phe Ala Ala Thr Glu Lys Ser Asn
85 90 95

Val Val Arg Gly Trp Val Phe Gly Ser Thr Met Asn Asn Lys Ser Gln
100 105 110

Ser Val Ile Ile Ile Asn Asn Ser Thr Asn Val Val Ile Arg Ala Cys
115 120 125

Asn Phe Glu Leu Cys Asp Asn Pro Phe Phe Ala Val Ser Lys Pro Met
130 135 140

Gly Thr Gln Thr His Thr Met Ile Phe Asp Asn Ala Phe Asn Cys Thr
145 150 155 160

Phe Glu Tyr Ile Ser Asp Ala Phe Ser Leu Asp Val Ser Glu Lys Ser
165 170 175

Gly Asn Phe Lys His Leu Arg Glu Phe Val Phe Lys Asn Lys Asp Gly
180 185 190

Phe Leu Tyr Val Tyr Lys Gly Tyr Gln Pro Ile Asp Val Val Arg Asp
195 200 205

Leu Pro Ser Gly Phe Asn Thr Leu Lys Pro Ile Phe Lys Leu Pro Leu
210 215 220

Gly Ile Asn Ile Thr Asn Phe Arg Ala Ile Leu Thr Ala Phe Ser Pro
225 230 235 240

Ala Gln Asp Ile Trp Gly Thr Ser Ala Ala Ala Tyr Phe Val Gly Tyr
245 250 255

Leu Lys Pro Thr Thr Phe Met Leu Lys Tyr Asp Glu Asn Gly Thr Ile
260 265 270

Thr Asp Ala Val Asp Cys Ser Gln Asn Pro Leu Ala Glu Leu Lys Cys
275 280 285

Ser Val Lys Ser Phe Glu Ile Asp Lys Gly Ile Tyr Gln Thr Ser Asn
290 295 300

Phe Arg Val Val Pro Ser Gly Asp Val Val Arg Phe Pro Asn Ile Thr
305 310 315 320

Asn Leu Cys Pro Phe Gly Glu Val Phe Asn Ala Thr Lys Phe Pro Ser
325 330 335

Val Tyr Ala Trp Glu Arg Lys Lys Ile Ser Asn Cys Val Ala Asp Tyr
340 345 350

Ser Val Leu Tyr Asn Ser Thr Phe Phe Ser Thr Phe Lys Cys Tyr Gly
355 360 365

```
Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
```

```
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200
```

```
Ala Gly  Leu Ile Ala Ile Val  Met Val Thr Ile Leu  Leu Cys Cys
    1205                 1210                 1215

Met Thr  Ser Cys Cys Ser Cys  Leu Lys Gly Ala Cys  Ser Cys Gly
    1220                 1225                 1230

Ser Cys  Cys Lys Phe Asp Glu  Asp Asp Ser Glu Pro  Val Leu Lys
    1235                 1240                 1245

Gly Val  Lys Leu His Tyr Thr
    1250                 1255


<210> SEQ ID NO 19
<211> LENGTH: 805
<212> TYPE: PRT
<213> ORGANISM: Homo sapiens

<400> SEQUENCE: 19

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
```

```
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735
```

-continued

```
Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
                805


<210> SEQ ID NO 20
<211> LENGTH: 4
<212> TYPE: PRT
<213> ORGANISM: Artificial Sequence
<220> FEATURE:
<223> OTHER INFORMATION: Synthetic Construct

<400> SEQUENCE: 20

Gly Ser Ala Ser
1


<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

His His His His His His His His
1               5
```

ANTI-SARS-COV-2 SPIKE PROTEIN ANTIBODIES AND METHODS OF USE

CROSS-REFERENCE TO RELATED APPLICATIONS

This application is a national phase application, filed under 35 U.S.C. § 371, of International Patent Application No. PCT/US2021/030794, filed May 5, 2021, which claims the benefit of U.S. Provisional Patent Application No. 63/020,483, filed May 5, 2020, each of which is incorporated herein by reference in its entirety.

STATEMENT AS TO FEDERALLY FUNDED RESEARCH

This invention was made with government support under Grant Number AI065315 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 3, 2025, is named 50811-010002_Sequence_Listing_10_3_25_ST25 and is 35,157 bytes in size.

BACKGROUND OF THE INVENTION

Coronaviruses are characterized by club-like spike(S) proteins that project from their surface, an unusually large RNA genome, and a unique replication strategy. Outbreaks of highly pathogenic strains of coronaviruses, such as Severe Acute Respiratory Syndrome Coronavirus (SARS-COV), Middle Eastern Respiratory Syndrome Coronavirus (MERS-COV), and most recently the 2019 novel coronavirus (SARS-CoV-2), have occurred. Like SARS-COV, SARS-COV-2 is a lineage B betacoronavirus that binds to angiotensin-converting enzyme 2 (ACE2) receptor to infect human cells. Binding of SARS-COV-2 and SARS-COV to the ACE2 receptor on target cells is mediated through their respective S proteins.

Very recently, COVID-19, a respiratory disease in humans caused by an infection of SARS-COV-2, emerged in Wuhan, China, and spread worldwide, resulting in the World Health Organization (WHO) declaring a pandemic on Mar. 11, 2020. Currently, worldwide there have been 1,872,073 confirmed cases of COVID-19 and 116,098 reported COVID-19-related deaths in at least 190 countries as of Apr. 13, 2020. To date, there is no vaccine or antiviral treatment shown to be effective for treating COVID-19.

Thus, there is an urgent need for safe and effective therapies and prophylactics for treating individuals having, or at risk of having, a betacoronavirus infection or associated disease, such as COVID-19.

SUMMARY OF THE INVENTION

The invention provides anti-SARS-COV-2 spike(S) protein antibodies and methods of their use.

In one aspect, the invention features an isolated antibody that binds SARS-COV-2 spike(S) protein, wherein the antibody binds to an epitope between amino acid residues 439-541 of SARS-COV-2 S protein (SEQ ID NO: 1). In some embodiments, the antibody binds to an epitope between amino acid residues 439-498 of SARS-COV-2 S protein (SEQ ID NO: 1). In further embodiments, the antibody binds to an epitope including at least one of amino acid residues Y449, F456, and Y489 of SARS-COV-2 S protein (SEQ ID NO: 1). In some embodiments, the epitope further includes at least one of amino acid residues Y453, A475, and Q493 of SARS-COV-2 S protein (SEQ ID NO: 1). In some embodiments, the antibody binds to an epitope comprising at least one of amino acid residues Y449, Y453, F456, A475, Y489, and Q493 of SARS-COV-2 S protein (SEQ ID NO: 1). In some embodiments, the antibody binds to an epitope including amino acid residues Y449, F456, and Y489 of SARS-COV-2 S protein (SEQ ID NO: 1). In some embodiments, the epitope further includes amino acid residues Y453, A475, and Q493 of SARS-COV-2 S protein (SEQ ID NO: 1). In some embodiments, the antibody binds to an epitope comprising the amino acid residues Y449, Y453, F456, A475, Y489, and Q493 of SARS-COV-2 S protein (SEQ ID NO: 1).

In another aspect, the invention features an isolated antibody that binds SARS-COV-2 S protein, wherein the antibody includes the following complementary determining regions (CDRs): (a) a CDR-H1 including the amino acid sequence of GFSFSSYGMH (SEQ ID NO: 2); (b) a CDR-H2 including the amino acid sequence of WYDGSDK (SEQ ID NO: 3); (c) a CDR-H3 including the amino acid sequence of ARERYFDWIFDF (SEQ ID NO: 4); (d) a CDR-L1 including the amino acid sequence of RASQSVSSSYLA (SEQ ID NO: 5); (e) a CDR-L2 including the amino acid sequence of GASSRAT (SEQ ID NO: 6); and (f) a CDR-L3 including the amino acid sequence of QQYGSSWT (SEQ ID NO: 7), or a combination of one or more of the above CDRs and one or more variants thereof having (i) at least about 85% sequence identity (e.g., 86%, 87%, 88%, 89%, 90%, 91%, 92%, 93%, 94%, 95%, 96%, 97%, 98%, or 99% sequence identity) to any one of SEQ ID NOs: 2-7, and/or (ii) one, two, or three amino acid substitutions relative to the amino acid sequence of any one of SEQ ID NOs: 2-7.

In some embodiments, the antibody further includes the following heavy chain framework regions (FRs): (a) an FR-H1 including the amino acid sequence of QVQLVESGGGVVQPGRSLRLSCAAS (SEQ ID NO: 8); (b) an FR-H2 including the amino acid sequence of WVRQAPGKGLEWVAVI (SEQ ID NO: 9); (c) an FR-H3 including the amino acid sequence of YYADSVKGRFTISRDNSKNTLYLQLNSLRAEDTAIYYC (SEQ ID NO: 10); and (d) an FR-H4 including the amino acid sequence of WGQGTLVTVSS (SEQ ID NO: 11), or a combination of one or more of the above FRs and one or more variants thereof having (i) at least about 85% sequence identity (e.g., 86%, 87%, 88%, 89%, 90%, 91%, 92%, 93%, 94%, 95%, 96%, 97%, 98%, or 99% sequence identity) to any one of SEQ ID NOs: 8-11, and/or (ii) one, two, or three amino acid substitutions relative to the amino acid sequence of any one of SEQ ID NOs: 8-11.

In some embodiments, the antibody further includes the following light chain FRs: (a) an FR-L1 including the amino acid sequence of EIVLTQSPGTLSLSPGERATLSC (SEQ ID NO: 12); (b) an FR-L2 including the amino acid sequence of WYQQKPGQAPRLLIY (SEQ ID NO: 13); (c) an FR-L3 including the amino acid sequence of GIPDRFSGSGSGTDFTLTISRLEPEDFAVYYC (SEQ ID NO: 14); and (d) an FR-L4 including the amino acid sequence of FGQGTKVEIK (SEQ ID NO: 15), or a combination of one or more of the above FRs and one or more variants thereof having (i) at least about 85% sequence identity (e.g., 86%, 87%, 88%, 89%, 90%, 91%, 92%, 93%, 94%, 95%, 96%, 97%, 98%, or 99% sequence identity) to any one of SEQ ID NOs: 12-15, and/or (ii) one, two, or three amino acid substitutions relative to the amino acid sequence of any one of SEQ ID NOs: 12-15.

In some embodiments, the antibody includes a heavy chain variable (VH) domain including an amino acid sequence having at least 95%, at least 96%, at least 97%, at least 98%, or at least 99% sequence identity to the amino acid sequence of SEQ ID NO: 16 and a light chain variable (VL) domain including an amino acid sequence having at least 95%, at least 96%, at least 97%, at least 98%, or at least 99% sequence identity to the amino acid sequence of SEQ ID NO: 17.

In another aspect, the invention features an isolated antibody that binds SARS-COV-2 S protein, wherein the antibody includes a VH domain including the amino acid of SEQ ID NO: 16 and a VL domain including the amino acid sequence of SEQ ID NO: 17.

In some embodiments, the antibody binds SARS-COV S protein (SEQ ID NO: 18). In some embodiments, the antibody binds to an epitope between amino acids residues 270-510 of SARS-COV S protein (SEQ ID NO: 18).

In some embodiments, the antibody is capable of inhibiting binding of SARS-COV-2 S protein to angiotensin-converting enzyme 2 (ACE2) receptor. In some embodiments, the antibody is capable of inhibiting binding of SARS-COV-2 S protein to ACE2 receptor by at least about 80% (e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%) at a concentration of about 330 nM or with an $EC_{50}$ of about 40 nM, as determined by an in vitro receptor binding inhibition assay.

In some embodiments, the antibody is capable of neutralizing SARS-COV-2. In some embodiments, the antibody is capable of neutralizing SARS-COV-2 with an $EC_{50}$ of about 5 μg/mL as determined by a plaque reduction neutralization test (PRNT). In some embodiments, the antibody is capable of neutralizing SARS-COV. In some embodiments, the antibody is capable of neutralizing SARS-CoV-2 and SARS-COV.

In some embodiments, the antibody binds SARS-COV-2 S protein with a $K_D$ of between about 100 pM and about 100 nM (e.g., between about 200 μM and about 900 μM, between about 1 nM and about 50 nM, or between about 10 nM and about 20 nM). In some embodiments, the antibody binds SARS-CoV-2 S protein with a $K_D$ of about 300 μM. In some embodiments, the antibody binds SARS-COV-2 S protein with a $K_D$ of about 13 nM. In some embodiments, the antibody binds SARS-COV-2 S protein with a $K_D$ of about 300 μM. In some embodiments, the antibody is an IgG class antibody (e.g., an IgG1 subclass antibody) that binds SARS-COV-2 S protein with a $K_D$ of between about 100 μM and about 100 nM (e.g., between about 1 nM and about 50 nM, or between about 10 nM and about 20 nM). In some embodiments, the antibody is an IgG1 subclass antibody that binds SARS-COV-2 S protein with a $K_D$ of about 13 nM. In some embodiments, the antibody is an IgA class antibody (e.g., an IgA1 subclass antibody) that binds SARS-COV-2 S protein with a $K_D$ of between about 100 μM and about 100 nM (e.g., between about 200 μM and about 900 μM, between about 1 nM and about 50 nM, or between about 10 nM and about 20 nM). In some embodiments, the antibody is an IgA1 subclass antibody that binds SARS-COV-2 S protein with a $K_D$ of about 300 μM.

In some embodiments, the antibody binds SARS-COV S protein with a $K_D$ of between about 10 μM and about 10 nM (e.g., between about 100 μM and about 10 nM, or between about 500 μM and about 2 nM). In some embodiments, the antibody binds SARS-COV S protein with a $K_D$ of about 1.3 nM. In some embodiments, the antibody binds SARS-COV S protein with a $K_D$ of about 1.4 nM. In some embodiments, the antibody is an IgG class antibody (e.g., an IgG1 subclass antibody) that binds SARS-CoV S protein with a $K_D$ of between about 10 μM and about 10 nM (e.g., between about 100 μM and about 10 nM, or between about 500 μM and about 2 nM). In some embodiments, the antibody is an IgG1 subclass antibody that binds SARS-COV S protein with a $K_D$ of about 1.3 nM. In some embodiments, the antibody is an IgA class antibody (e.g., an IgA1 subclass antibody) that binds SARS-COV S protein with a $K_D$ of between about 10 μM and about 10 nM (e.g., between about 100 μM and about 10 nM, or between about 500 μM and about 2 nM). In some embodiments, the antibody is an IgA1 subclass antibody that binds SARS-COV S protein with a $K_D$ of about 1.4 nM.

In some embodiments, the $K_D$ is measured by a surface plasmon resonance assay at 25° C.

In some embodiments, the antibody is a monoclonal antibody.

In another aspect, the invention provides an isolated monoclonal antibody that binds SARS-COV-2 S protein, wherein the antibody competes for binding to SARS-COV-2 S protein with any of the preceding antibodies.

In some embodiments of any of the preceding aspects, the antibody is a human antibody (e.g., a human monoclonal antibody), an IgG class antibody (e.g., an IgG1 subclass antibody), and/or an IgA (e.g., an IgA1 or IgA2 subclass antibody) class antibody (e.g., a secretory IgA (sIgA) or dimeric IgA (dIgA) class antibody). In some embodiments, the IgA class antibody is a secretory IgA (SIgA) class antibody.

In some embodiments, the antibody is a full-length antibody. In other embodiments, the antibody is an antibody fragment that binds SARS-COV-2 S protein selected from the group consisting of Fab, Fab', Fab'-SH, Fv, single chain variable fragment (scFv), and (Fab') 2 fragments.

In another aspect, the invention features an isolated nucleic acid encoding the antibody of any one of the preceding aspects.

In another aspect, the invention features a vector including the nucleic acid of the preceding aspect.

In another aspect, the invention features a host cell including the vector of the preceding aspect. In some embodiments, the host cell is a mammalian cell (e.g., a Chinese hamster ovary (CHO) cell) or a prokaryotic cell (e.g., an *E. coli* cell).

In another aspect, the invention features a method of producing the antibody of any one the preceding aspects, the method including culturing a host cell including the nucleic acid of a preceding accept in a culture medium. In some embodiments, the method further includes recovering the antibody from the host cell or the culture medium.

In another aspect, the invention features a composition including the antibody of any one of the preceding aspects.

In another aspect, the invention features a pharmaceutical composition including the antibody of any one of the preceding aspects. In some embodiments, the pharmaceutical composition further includes a pharmaceutically acceptable carrier, excipient, or diluent. In some embodiments the pharmaceutical composition is formulated for treating a betacoronavirus infection in a subject.

In another aspect, the invention features a method of treating a subject having a betacoronavirus infection or presumed to have a betacoronavirus infection, the method including administering to the subject an effective amount of any one of the preceding antibodies or pharmaceutical compositions, thereby treating the subject.

In another aspect, the invention features a method of treating a subject at risk of having a betacoronavirus infection, the method including administering to the subject an effective amount of any one of the preceding antibodies or pharmaceutical compositions, thereby treating the subject.

In some embodiments, the betacoronavirus infection is with a lineage B betacoronavirus (e.g., SARS-COV-2 or SARS-COV) or a lineage C betacoronavirus (e.g., MERS-COV).

In some embodiments, the subject has or is presumed to have coronavirus disease 19 (COVID-19).

In some embodiments, the subject has or is presumed to have severe acute respiratory syndrome (SARS).

In some embodiments, the antibody is administered to the subject at a dosage of about 0.1 mg/kg to about 100 mg/kg (e.g., about 1 mg/kg to about 80 mg/kg, or about 1 mg/kg to about 40 mg/kg).

In some embodiments, the antibody is administered to the subject intravenously. In other embodiments, the antibody is administered to the subject intranasally. In some embodiments, the antibody is administered to the subject by inhalation.

In some embodiments, the antibody is administered to the subject as a monotherapy.

In some embodiments, the antibody is administered to the subject as a combination therapy. In some embodiments, the combination therapy includes administering to the subject one or more additional therapeutic agents (e.g., a second therapeutic antibody (e.g., gimsilumab), an antifungal agent, an antiviral agent (e.g., remdesivir, favilavir, OYA1, lopinavir, ritonavir, galidesivir, EIDD-1931, EIDD-2801, or SNG001 (inhaled interferon-beta-1a)), an antiparasitic agent (e.g., hydroxychloroquine or chloroquine), an antibacterial agent (e.g., azithromycin), or a combination thereof). In some embodiments, the antibody is administered to the subject prior to, concurrently with, or after administration of the one or more additional therapeutic agents.

In another aspect, the invention features a method of detecting a betacoronavirus (e.g., a lineage B betacoronavirus (e.g., SARS-COV-2 or SARS-COV) or a lineage C betacoronavirus (e.g., MERS-COV)) in a sample from a subject, the method including contacting the sample with the antibody of any one of the preceding aspects under conditions permissive for binding of the antibody to a betacoronavirus and detecting whether a complex is formed between the antibody and the betacoronavirus. In some embodiments, the sample is a swab sample (e.g., a nasopharyngeal swab), a lavage sample (e.g., a bronchoalveolar lavage), a blood sample, a plasma sample, a sputum sample, a urine sample, a stool sample, or a mucosal secretion sample.

In some embodiments, the subject is presumed to have a betacoronavirus infection. In some embodiments, the subject is a mammal (e.g., a human).

In some aspects, the invention features a method of purifying a betacoronavirus (e.g., a lineage B betacoronavirus (e.g., SARS-COV-2 or SARS-COV) or a lineage C betacoronavirus (e.g., MERS-COV)) or betacoronavirus S protein (e.g., a SARS-COV-2 S protein, a SARS-COV S protein, and a MERS-COV S protein) in a sample (e.g., a sample from a subject), the method including contacting the sample with the antibody of any one of the preceding aspects under conditions permissive for binding of the antibody to a betacoronavirus S protein, detecting whether a complex is formed, and optionally disrupting the complex, thereby purifying the betacoronavirus or betacoronavirus S protein.

In another aspect, the invention features a kit including the antibody of any one of the preceding aspects and a package insert including instructions for using the antibody for treating a subject having or at risk of developing a disorder associated with a betacoronavirus infection.

In another aspect, the invention features a kit for detecting a betacoronavirus, the kit including the antibody of any one of the preceding aspects and a package insert including instructions for using the antibody to detect a betacoronavirus. In some embodiments, the antibody is conjugated to a label or a tag.

In another aspect, the invention features a kit for purifying a betacoronavirus (e.g., a lineage B betacoronavirus (e.g., SARS-COV-2 or SARS-COV) or a lineage C betacoronavirus (e.g., MERS-COV)) or a betacoronavirus S protein (e.g., a SARS-COV-2 S protein, a SARS-COV S protein, and a MERS-COV S protein), the kit including the antibody of any one of the preceding aspects and a package insert including instructions for using the antibody to purify a betacoronavirus or betacoronavirus S protein. In some embodiments, the antibody is conjugated to a label, a tag, or a solid support.

In another aspect, the invention features an antibody that binds SARS-COV-2 S protein for treating a subject having a betacoronavirus infection or presumed to have a betacoronavirus infection, wherein the antibody: (a) binds to an epitope between amino acid residues 439-541 of SARS-COV-2 S protein (SEQ ID NO: 1); or (b) includes the following complementary determining regions (CDRs): (i) a CDR-H1 including the amino acid sequence of GFSFSSYGMH (SEQ ID NO: 2); (ii) a CDR-H2 including the amino acid sequence of WYDGSDK (SEQ ID NO: 3); (iii) a CDR-H3 including the amino acid sequence of ARERYFDWIFDF (SEQ ID NO: 4); (iv) a CDR-L1 including the amino acid sequence of RASQSVSSSYLA (SEQ ID NO: 5); (v) a CDR-L2 including the amino acid sequence of GASSRAT (SEQ ID NO: 6); and (vi) a CDR-L3 including the amino acid sequence of QQYGSSWT (SEQ ID NO: 7), or a combination of one or more of the above CDRs and one or more variants thereof having (i) at least about 85% sequence identity (e.g., 86%, 87%, 88%, 89%, 90%, 91%, 92%, 93%, 94%, 95%, 96%, 97%, 98%, or 99% sequence identity) to any one of SEQ ID NOs: 2-7, and/or (ii) one, two, or three amino acid substitutions relative to the amino acid sequence of any one of SEQ ID NOs: 2-7.

In another aspect, the invention features an antibody that binds SARS-COV-2 S protein for treating a subject at risk of having a betacoronavirus infection, wherein the antibody: (a) binds to an epitope between amino acid residues 439-541 of SARS-COV-2 S protein (SEQ ID NO: 1); or (b) includes the following complementary determining regions (CDRs): (i) a CDR-H1 including the amino acid sequence of GFSFSSYGMH (SEQ ID NO: 2); (ii) a CDR-H2 including the amino acid sequence of WYDGSDK (SEQ ID NO: 3); (iii) a CDR-H3 including the amino acid sequence of ARERYFDWIFDF (SEQ ID NO: 4); (iv) a CDR-L1 including the amino acid sequence of RASQSVSSSYLA (SEQ ID NO: 5); (v) a CDR-L2 including the amino acid sequence of GASSRAT (SEQ ID NO:6); and (vi) a CDR-L3 including the amino acid sequence of QQYGSSWT (SEQ ID NO: 7), or a combination of one or more of the above CDRs and one or more variants thereof having (i) at least about 85% sequence identity (e.g., 86%, 87%, 88%, 89%, 90%, 91%, 92%, 93%, 94%, 95%, 96%, 97%, 98%, or 99% sequence identity) to any one of SEQ ID NOs: 2-7, and/or (ii) one, two, or three amino acid substitutions relative to the amino acid sequence of any one of SEQ ID NOs: 2-7.

In some embodiments, the antibody for treating a subject (e.g., a subject having or at risk of having a betacoronavirus infection) binds to an epitope between amino acid residues 439-498 of SARS-CoV-2 S protein (SEQ ID NO: 1). In further embodiments, the antibody binds to an epitope including at least one of amino acid residues Y449, F456, and Y489 of SARS-COV-2 S protein (SEQ ID NO: 1). In some embodiments, the epitope further includes at least one of amino acid residues Y453, A475, and Q493 of SARS-COV-2 S protein (SEQ ID NO: 1). In some embodiments, the antibody binds to an epitope comprising at least one of amino acid residues Y449, Y453, F456, A475, Y489, and Q493 of SARS-COV-2 S protein (SEQ ID NO: 1). In some embodiments, the antibody binds to an epitope including amino acid residues Y449, F456, and Y489 of SARS-COV-2 S protein (SEQ ID NO: 1). In some embodiments, the epitope further includes amino acid residues Y453, A475, and Q493 of SARS-COV-2 S protein (SEQ ID NO: 1). In some embodiments, the antibody binds to an epitope comprising the amino acid residues Y449, Y453, F456, A475, Y489, and Q493 of SARS-COV-2 S protein (SEQ ID NO: 1).

In some embodiments of the two preceding aspects, the betacoronavirus infection is with a lineage B betacoronavirus (e.g., SARS-COV-2 or SARS-COV) or a lineage C betacoronavirus (e.g., MERS-COV).

In some embodiments, the antibody is for use in treating a subject that has or is presumed to have coronavirus disease 19 (COVID-19).

In some embodiments, the antibody is for use in treating a subject that has or is presumed to have severe acute respiratory syndrome (SARS).

In some embodiments, the antibody is formulated for administration to the subject at a dosage of about 0.1 mg/kg to about 100 mg/kg (e.g., about 1 mg/kg to about 80 mg/kg or about 1 mg/kg to about 40 mg/kg). In some embodiments, wherein the antibody is formulated for intravenous administration, intranasal administration, or for administration by inhalation.

In some embodiments, the antibody is formulated for administration to the subject as a monotherapy.

In some embodiments, the antibody is formulated for administration to the subject as a combination therapy. In certain embodiments, the combination therapy further includes one or more additional therapeutic agents (e.g., (e.g., a second therapeutic antibody (e.g., gimsilumab), an antifungal agent, an antiviral agent (e.g., remdesivir, favilavir, OYA1, lopinavir, ritonavir, galidesivir, EIDD-1931, EIDD-2801, or SNG001 (inhaled interferon-beta-1a)), an antiparasitic agent (e.g., hydroxychloroquine or chloroquine), an antibacterial agent (e.g., azithromycin), or a combination thereof) that are formulated for administration to the subject. In some embodiments, the antibody is formulated for administration to the subject prior to, concurrently with, or after administration of the one or more additional therapeutic agents.

In some embodiments, the antibody is formulated for use in treating a subject that is presumed to have a betacoronavirus infection.

In some embodiments, the subject is a mammal (e.g., a human).

BRIEF DESCRIPTION OF THE DRAWINGS

FIG. 2A is a sensorgram showing the binding kinetics of MAb362 IgG1 to the RBD of the S protein of SARS-COV-2 (amino acids 319-541 of the full-length SARS-COV-2 S protein, which has the amino acid sequence of SEQ ID NO: 1). FIG. 2B is a sensorgram showing the binding kinetics of MAb362 IgG1 to the RBD of the S protein of SARS-COV (amino acids 270-510 of the full-length SARS-CoV S protein, which has the amino acid sequence of SEQ ID NO: 18). FIG. 2C is a sensorgram showing the binding kinetics of MAb362 IgA1 to the RBD of the S protein of SARS-COV (amino acids 270-510 of the full-length SARS-COV S protein, which has the amino acid sequence of SEQ ID NO: 18). FIG. 2D is a sensorgram showing the binding kinetics of MAb362 IgA1 to the RBD of the S protein of SARS-COV-2 (amino acids 319-541 of the full-length SARS-COV-2 S protein, which has the amino acid sequence of SEQ ID NO: 1).

FIG. 4A shows the surface representation of a structural model of an MAb362: SARS-COV-2 S protein RBD complex shown in transparency, with the secondary structure shown in ribbon form. FIG. 4B shows the electronegativity of amino acids in the binding site of the structural model of MAb362 and SARS-COV-2 S protein RBD involved in the binding complex formation.

FIG. 5A shows the side chain positions of amino acid residues of MAb362 shown in the structural model to be involved in MAb362 binding to SARS-COV-2 S protein RBD. The location of the CDRs involved in binding are highlighted, in particular residues S150, S151, and Y152 of CDR-L1 (residues 31-33 of SEQ ID NO: 17, respectively) and A171, S172, S173, R174, and G184 of CDR-L2 (residues 52, 53, 54, 55, and 64 of SEQ ID NO: 17, respectively). FIGS. 5B and 5C show the side chain positions of amino acid residues of SARS-COV-2 S protein RBD shown in the structural model to be involved in binding with MAb362 in two crystal structures.

FIG. 6B shows the interaction among residues F456, Y489 of SARS-COV-2 RBD and the light chain residues S173, R174, S183, and G184 (residues 54, 55, 64, and 65 of SEQ ID NO: 17, respectively) of MAb362. FIG. 6C shows the interaction among residues between Y449 of SARS-COV-2 RBD and the light chain residue Y152 (residue 33 of SEQ ID NO: 17) along with the location of residues W104 (residue 104 of SEQ ID NO: 16), Y211, and G212 (residues 92 and 93 of SEQ ID NO: 17, respectively) located within the interaction interface.

FIG. 7A shows a surface representation of MAb362 (green) binding to SARS-COV-2 S protein RBD (purple) overlaid with the ACE2 receptor (orange) binding to SARS-COV-2 S protein. FIG. 7B shows the surface of the SARS-COV-2 RBD and MAb362 shown in transparency.

FIG. 9C is a sensorgram showing the binding kinetics of MAb362 IgG to the RBD of the S protein of SARS-COV. FIG. 9D is a sensorgram showing the binding kinetics of MAb362 IgA to the RBD of the S protein of SARS-COV. FIG. 9E is a sensorgram showing the binding kinetics of MAb362 IgG to the RBD of the S protein of SARS-COV-2.

FIG. 9F is a sensorgram showing the binding kinetics of MAb362 IgA to the RBD of the S protein of SARS-COV-2.

FIG. 10C shows the surface representation of a structural model of an MAb362: SARS-COV-2 S protein RBD complex. The Mab362 heavy chain and light chain variable regions (VH and VL) are indicated. FIG. 10D shows predicted binding interface on the SARS-COV-2 RBD with Mab362. The residues identified by mutagenesis from FIG. 10B are labeled and colored according to influence degree.

FIG. 11A shows a surface representation of MAb362 (green) binding to SARS-COV-2 S protein RBD (purple) overlaid with the ACE2 receptor (orange) binding to SARS-COV-2 S protein. FIG. 11B shows the binding interface on SARS-COV-2 RBD with ACE2 calculated from the co-crystal structure of the complex. The binding interface shown as a darker shade is defined as having vdW contacts great than-0.5 kcal mol-1.

FIG. 11C shows the positioning of MAb362 on SARS-COV-2 RBD (violet) relative to the binding of other currently published SARS-COV-2 RBD-neutralizing antibodies: CR3022 (PDB: 6W41; orange); S309 (PDB: 6WPT; cyan); REGN10933 and REGN10987 (PDB: 6XDG; magenta and yellow); P2B-2F6 (PDB: 7BWJ; salmon); CB6 (PDB: 7C01; wheat) and B38 (PDB: 7BZ5; blue). FIG. 11D shows a predicted MAb362 molecular model on the spike trimer in open conformation with one RBD domain exposed 6VYB.

FIG. 13A is an image of a surface representation of a structural model depicting the predicted binding interface on the SARS-COV-2 RBD with hACE2. Key residues identified as having an effect in mutagenesis are labeled and colored according to influence degree.

FIG. 13B is a table showing strength of binding to hACE2 and fold change relative to wild type for SARS-COV-2 S protein comprising the indicated mutations.

FIG. 13C is an image of a surface representation of a structural model showing the binding interface on MAb362 with SARS-COV-2 RBD. The binding interface shown as darker shade is defined as having vdW contacts greater than-0.5 kcal mol-1. Residues from all CDRs from both heavy and light chains pack against the SARS-COV-2 RBD are labeled by circles.

DETAILED DESCRIPTION OF EMBODIMENTS OF THE INVENTION

I. Definitions

Figure 1A:
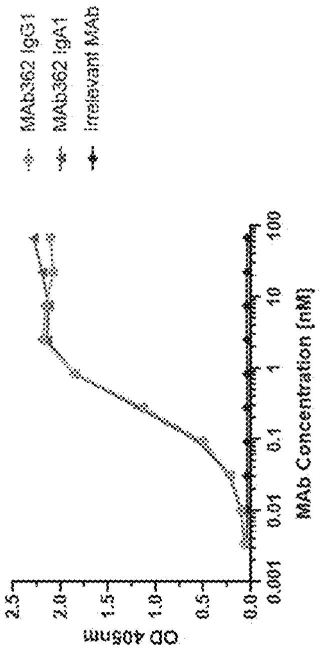
FIGS. 1A-1B are graphs depicting the enzyme linked immunosorbent assay (ELISA) binding curves of MAb362 to the S1 subunit of the SARS-COV (FIG. 1A) and SARS-COV-2 S (FIG. 1B) proteins, and fragments thereof.

The terms "anti-SARS-COV-2 S protein antibody," "an antibody that binds to SARS-COV-2 S protein," and "an antibody that specifically binds to SARS-COV-2 S protein" refer to an antibody that is capable of binding SARS-COV-2 S protein with sufficient affinity such that the antibody is useful as a preventative, diagnostic, and/or therapeutic agent in targeting S protein. In one embodiment, the extent of binding of an anti-S protein antibody to an unrelated, non-S protein is less than about 10% of the binding of the antibody to S protein as measured, e.g., by a surface plasmon resonance (SPR) assay. In certain embodiments, an antibody that binds to S protein has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

The term "antibody" as used herein in the broadest sense encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody" can refer, for example, to a glycoprotein comprising at least two heavy chains (HCs) and two light chains (LCs) inter-connected by disulfide bonds, or an antigen binding portion thereof. Each heavy chain is comprised of a heavy chain variable region (VH) and a heavy chain constant region (CH). The heavy chain constant region may be comprised of three domains, CH1, CH2, and/or CH3. Each light chain is comprised of a light chain variable region (VL) and a light chain constant region (CL). The VH and VL regions can be further subdivided into regions of hypervariability, termed "complementarity determining regions" (CDRs), interspersed with regions that are more conserved, termed "framework regions" (FRs). Each VH and VL may be composed, for example, of three CDRs and four FRs, arranged from amino-terminus to carboxyl-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "coronavirus" as used herein in the broadest sense encompasses enveloped viruses with a positive-sense single-stranded RNA genome and a nucleocapsid of helical symmetry and are characterized by club-like spike proteins (S proteins) that project from their surface. Coronaviruses commonly infect and cause disease in mammals (e.g., humans) and birds. In humans, coronaviruses typically cause upper respiratory infections that can range from mild to lethal. Four genera of coronavirus have been identified: (1) Alphacoronaviruses (e.g., Human coronavirus 229E, Human coronavirus NL63, Miniopterus bat coronavirus 1, Miniopterus bat coronavirus HKU8, Porcine epidemic diarrhea virus, Rhinolophus bat coronavirus HKU2, Scotophilus bat coronavirus 512); (2) Betacoronaviruses (e.g., Betacoronavirus 1 (Bovine Coronavirus, Human coronavirus OC43), Human coronavirus HKU1, Murine coronavirus, *Pipistrellus* bat coronavirus HKU5, Rousettus bat coronavirus HKU9, Severe acute respiratory syndrome-related coronavirus (SARS-COV, SARS-COV-2), *Tylonycteris* bat coronavirus HKU4, Middle East respiratory syndrome-related coronavirus, Hedgehog coronavirus 1 (EriCoV)); (3) Gammavoronavirus (e.g., Beluga whale coronavirus SW1, Infectious bronchitis virus); and (4) Deltacoronavirus (e.g., Bulbul coronavirus HKU11, Porcine coronavirus HKU15). Betavoronaviruses can be further categorized into four lineages: lineage A (including HCoV-OC43 and HCoV-HKU1), lineage B (including SARS-COV, SARS-COV-2), lineage C (including BtCoV-HKU4, BtCoV-HKU5, and MERS-COV), and lineage D (including BtCoV-HKU9). At least three pathogenic strains of coronavirus produce symptoms that are potentially severe: SARS-COV that caused the 2003-2004 SARS outbreak in China, MERS-COV that caused a 2013-2014 outbreak in the Middle East and neighboring countries, and most recently SARS-COV-2 that has caused the COVID-19 worldwide pandemic in the beginning of 2020. These viruses are endemic in human populations and cause more severe disease in neonates, the elderly, and in individuals living with underlying illnesses, with a greater incidence of lower respiratory tract infection in these populations.

The term "COVID-19" as used herein refers to coronavirus disease 2019 (COVID-19), a respiratory disease caused by a SARS-COV-2 coronavirus infection. SARS-COV-2 can spread from person to person (e.g., persons who are in close contact with one another (e.g., within six-ten feet)) and through respiratory droplets produced when a person having been infected with the SARS-COV-2 virus coughs or sneezes and the droplets can come into contact (e.g., contact the nose, the mouth, the eyes, and/or be inhaled into the lungs) with another person thereby exposing the person to the virus. It may also be possible for a person to be exposed to SARS-COV-2 by touching a surface contaminated with the virus and then touching their own mouth, nose, or their eyes. The incubation period before onset of symptoms of COVID-19 is approximately 2-14 days after exposure to SARS-COV-2. Symptoms of COVID-19 may include fever, cough, and difficulty breathing. Severity of symptoms may range from mild (e.g., no reported symptoms) to severe illness, including illness resulting in death. The elderly and persons of all ages with underlying health conditions are at higher risk of developing serious illness. A subject may be at risk of having COVID-19 if they have been exposed to someone who has been diagnosed as having the disease, recently travelled to a location experiencing an outbreak of COVID-19, is elderly, is immunocompromised, or has another comorbid condition as described herein. A subject can be diagnosed as having COVID-19 by one of skill in the art based on symptoms or a diagnostic test (e.g., an ELISA, lateral flow chromatographic immunoassays to detect SARS-COV-2 antibodies, or Abbot ID NOW™ platform).

The terms "severe acute respiratory syndrome" and "SARS," as used herein, refer to the disease caused by SARS-COV. The symptoms of SARS are similar to COVID-19, and may include fever, muscle pain, lethargy, cough, sore throat, and other nonspecific symptoms, such as diarrhea. SARS may eventually lead to shortness of breath and pneumonia. The average incubation period before the onset of symptoms of SARS is believed to be approximately 4-6 days but may be as short as 1 day or as long as 14 days. A subject may be at risk of having a SARS-COV infection if they present with any of the symptoms, including a fever (e.g., a fever of at least 100° F.), and a history of traveling to a location experiencing a SARS-COV outbreak, or had contact with someone with a diagnosis of SARS within the last 10 days.

The terms "Middle Eastern respiratory Syndrome" and "MERS," as used herein, refer to the disease caused by MERS-COV. Symptoms of MERS are like SARS and COVID-19, ranging from fever, cough, shortness of breath, and body aches. Symptoms of MERS differ from SARS and COVID-19 in an increased presentation of gastrointestinal symptoms such as diarrhea, vomiting, and abdominal pain. The average incubation period before the onset of symptoms of MERS is 5.5 days, ranging from 2-15 days. A subject may be at risk of having a MERS-COV infection if they present with any of the symptoms, including a fever (at least 100° F.), and a history of traveling to a location experiencing a MERS-COV outbreak, or had contact with someone with a diagnosis of MERS within the last 10 days.

The terms "full-length antibody," "intact antibody," and "whole antibody," are used herein interchangeably to refer to an antibody having a structure substantially similar to a native antibody structure or having heavy chains that contain an Fc region as defined herein.

The terms "S protein" and "spike protein" refer to the spike glycoprotein encoded by a betacoronavirus (e.g., SARS-COV-2, SARS-COV, or MERS-COV). The term "protein" is used interchangeably with "polypeptide." The full-length SARS-COV-2 S protein has the amino acid sequence of SEQ ID NO: 1. The full-length SARS-COV S protein has the amino acid sequence of SEQ ID NO: 18.

The term "S protein receptor binding domain," "S protein RBD," and "RBD," or a variation thereof, refers to the S1B domain within the S1 subunit of an S protein that contains amino acid residues involved in binding to human angiotensin-converting enzyme 2 (ACE2) receptor. The RBD of SARS-COV-2 S protein contains amino acid residues 319-541 of the full-length SARS-COV-2 S protein, which has the amino acid sequence of SEQ ID NO: 1. The RBD of SARS-COV S protein contains amino acid residues 270-510 of the full-length SARS-COV-2 protein, which has the amino acid sequence of SEQ ID NO: 18. Within each of the RBDs of SARS-COV-2 S protein and SARS-COV S protein is a "RBD core," also referred to herein as "receptor binding subdomain." The RBD core is a region of the SARS-COV-2 and SARS-COV S protein RBD that loops out from the antiparallel betasheet S1B core domain structure and directly engages the ACE2 receptor. In some embodiments, the SARS-COV-2 S protein RBD core consists of amino acid residues 438-498 of the full-length SARS-COV-2 S protein (SEQ ID NO: 1). The SARS-COV S protein RBD core consists of amino acid residues 425-484 of the full-length SARS-COV S protein (SEQ ID NO: 18).

The terms "angiotensin-converting enzyme 2 (ACE2) receptor" and "ACE2 receptor" are used herein interchangeably to refer to angiotensin-converting enzyme 2, an enzyme attached to the outer surface (cell membrane) of cells in the lungs, arteries, heart, kidney, and intestines, which lowers blood pressure by catalyzing the hydrolysis of angiotensin II (a vasoconstrictor peptide) into angiotensin (a vasodilator). ACE2 receptor is a transmembrane protein and serves as the main entry point into cells for some coronaviruses, including HCoV-NL63, SARS-COV (the virus that causes SARS), and SARS-COV-2 (the virus that causes COVID-19). More specifically, the binding of the S proteins of SARS-COV-2 (SEQ ID NO: 1) and SARS-COV (SEQ ID NO: 18) to the enzymatic domain of ACE2 on the surface of cells results in endocytosis and translocation of both the virus and the enzyme into endosomes located within the cell. The amino acid sequence of an exemplary human ACE2 receptor is shown under UniProtKB-Q9BYF1 or in SEQ ID NO: 19.

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) Nature 368 (6474): 856-859); Lonberg, N. (1994) Handbook of Experimental Pharmacology 113:49-101; Lonberg, N. and Huszar, D. (1995) Intern. Rev. Immunol. Vol. 13:65-93, and Harding, F. and Lonberg, N. (1995) Ann. N.Y. Acad. Sci 764:536-546). However, the term "human antibody" does not include antibodies in which CDR sequences derived from the germline of another mammalian species, such as a mouse, have been grafted onto human framework sequences (i.e., humanized antibodies).

The term "monoclonal antibody," as used herein, refers to an antibody obtained from a population of substantially homogenous antibodies that displays a binding specificity and affinity for an epitope on a betacoronavirus S protein (e.g., a SARS-COV-2 S protein, SARS-COV S protein, and/or MERS-COV S protein). Accordingly, the term "human monoclonal antibody," or "HuMAb," refers to an antibody which displays a binding specificity for a betacoronavirus S protein (e.g., a SARS-COV-2 S protein, SARS-COV S protein, and/or MERS-COV S protein) and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

An "antibody fragment" refers to a molecule other than an intact antibody that comprises a portion of an intact antibody that specifically binds to the antigen (e.g., a SARS-COV-2 S protein) to which the intact antibody binds. Examples of antibody fragments include, but are not limited to, Fv, Fab, Fab', Fab'-SH, $F(ab')_2$; diabodies; linear antibodies; single-chain antibody molecules (e.g., scFv); and multispecific antibodies formed from antibody fragments. These antibody fragments are obtained using conventional techniques, and the fragments are screened for utility in the same manner as are intact antibodies. Antibody fragments can be produced by recombinant DNA techniques, or by enzymatic or chemical cleavage of intact immunoglobulins.

The terms "reduce binding" and "inhibit binding" as used herein refer to the ability of an antibody (e.g., an anti-SARS-COV-2 S protein antibody) to reduce the binding of a betacoronavirus S protein (e.g., a SARS-COV-2 S protein) to an ACE2 receptor. Inhibition or reduction in binding may be anywhere from about 20% to about 100% (e.g., about 25% to about 100%, about 30% to about 100%, about 35% to about 100%, about 40% to about 100%, about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 90% to about 100%, or about 95% to about 100%). In some embodiments, inhibition or reduction of binding of SARS-CoV-2 S protein to an ACE2 receptor by an antibody disclosed herein (e.g., an anti-SARS-COV-2 S protein antibody, e.g., Mab32) is by at least about 75%, at least about 80%, at least about 83%, or at least about 83.4% (e.g., at an antibody concentration of around 330 nM, e.g., 333 nM). Inhibition or reduction of binding of SARS-COV or SARS-COV-2 S protein to an ACE2 receptor by an antibody disclosed herein (e.g., an anti-SARS-COV-2 S protein antibody, e.g., Mab32) may be measured as described herein, for example by a flow cytometry-based receptor binding inhibition assay.

The term "neutralize" as used herein refers to the ability of an antibody (e.g., an anti-SARS-COV-2 antibody) to inhibit the infectivity of a virus (e.g., a betacoronavirus (e.g., SARS-COV-2, SARS-COV, and/or MERS-COV)). Neutralization can occur in several ways. For example, the antibody may block viral binding to a receptor (e.g., a SARS-COV-2 S protein binding to an ACE2 receptor), block viral uptake into the cell, prevent uncoating of the genome in an endosome, and/or cause aggregation of the virus particles. Neutralization of a virus by an antibody (e.g., an anti-SARS-COV-2 S protein antibody) may be measured by various means, including a plaque reduction neutralization test (PRNT) that quantifies the titer of neutralizing antibodies for a virus as described in Okba et al. *Emerg. Infect. Dis.* 25:1868-1877, 2019. Other methods, such as hemagglutination and commercial Enzyme immunoassays may be used to measure antibody neutralization.

The term "about" as used herein refers to the usual error range for the respective value readily known to the skilled person in this technical field. Reference to "about" a value or parameter herein includes (and describes) embodiments that are directed to that value or parameter per se.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein.

Specific illustrative and exemplary embodiments for measuring binding affinity are described below.

The term "$K_D$," as used herein, is intended to refer to the dissociation equilibrium constant of a particular antibody-antigen interaction. Typically, the antibodies of the invention bind to betacoronavirus S protein with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower when determined by surface plasmon resonance (SPR) technology in a BIACORE®-3000 instrument using recombinant betacoronavirus S protein as the analyte and the antibody as the ligand.

A "disorder" is any condition that would benefit from treatment including, but not limited to, chronic and acute disorders or diseases including those pathological conditions which predispose the mammal to the disorder in question.

As used herein, the term "disorder associated with a betacoronavirus infection," or "disorder associated with a coronavirus infection," refers to any disease, the onset, progression, or the persistence of the symptoms of which requires the participation of a betacoronavirus. Exemplary disorders associated with a betacoronavirus infection are, for example, coronavirus disease 19 (COVID-19) caused by SARS-COV-2, severe acute respiratory syndrome (SARS) caused by SARS-COV, and Middle Eastern respiratory syndrome (MERS) caused by MERS-COV.

The term "EC50," as used herein, refers to the concentration of an antibody or an antigen-binding portion thereof, which induces a response, either in an in vivo or an in vitro assay, which is 50% of the maximal response (i.e., halfway between the maximal response and the baseline).

The terms "effective amount," "effective dose," and "effective dosage" as used herein are defined as an amount sufficient to achieve, or at least partially achieve, the desired effect. The term "therapeutically effective dose" or "therapeutically effective amount" is defined as an amount sufficient to prevent, cure, or at least partially arrest, the disease (e.g., COVID-19, SARS, or MERS) and its complications in a patient already suffering from the disease or at risk of developing the disease. Amounts effective for this use will depend upon the severity of the disorder being treated and the general state of the patient's own immune system.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance. See, for example, Epitope Mapping Protocols in Methods in Molecular Biology, Vol. 66, G. E. Morris, Ed. (1996). Epitopes can also be defined by point mutations in the target protein (e.g., S protein), which affect the binding of the antibody (e.g., monoclonal antibody).

The term "host cell," as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated antibody" is one which has been identified and separated and/or recovered from a component of its natural environment and/or is substantially free of other antibodies having different antigenic specificities (e.g., an isolated antibody that binds to SARS-COV-2 S protein is substantially free of antibodies that specifically bind antigens other than SARS-COV-2 S protein). Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using COOMASSIE™ blue or, preferably, silver stain. Isolated antibody includes the antibody in situ within recombinant cells since at least one component of the antibody's natural environment will not be present. Similarly, isolated antibody includes the antibody in medium around recombinant cells. Ordinarily, however, isolated antibody will be prepared by at least one purification step. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid," as used herein in reference to nucleic acids molecules encoding antibodies or antibody portions (e.g., VH, VL, CDRs) that bind to S protein, is intended to refer to a nucleic acid molecule in which the nucleotide sequences encoding the antibody or antibody portion are free of other nucleotide sequences encoding antibodies that bind antigens other than S protein, which other sequences may naturally flank the nucleic acid in human genomic DNA.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical composition" refers to a preparation which is in such form as to permit the biological activity of an active ingredient (e.g., antibody that binds SARS-COV-2 S protein) contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE®-3000 instrument, which can be performed, for example, using recombinant S protein as the analyte and the antibody as the ligand. In some embodiments, binding by the antibody to the predetermined antigen is with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody that specifically binds to an antigen" or "an antibody that binds to an antigen."

A "subject" or an "individual" is a mammal. Mammals include, but are not limited to, domesticated animals (e.g., cows, sheep, cats, dogs, and horses), primates (e.g., humans and non-human primates such as monkeys), rabbits, deer, bats, felines, and rodents (e.g., mice and rats). In certain embodiments, the subject or individual is a human.

The terms "treat," "treating," and "treatment," as used herein, refer to preventative or therapeutic measures described herein. The methods of "treatment" employ administration to a subject in need of such treatment an antibody of the present invention, for example, a subject at risk of developing a betacoronavirus infection (e.g., a SARS-COV-2 infection, a SARS-COV-infection, or a MERS-COV infection). In some instances, the treatment is for a subject at risk of developing a disorder associated with a betacoronavirus infection or a subject having a disorder associated with a betacoronavirus infection (e.g., COVID-19, SARS, or MERS), in order to prevent, cure, delay, reduce the severity of, or ameliorate one or more symptoms of the disorder or recurring disorder, or in order to prolong the survival of a subject beyond that expected in the absence of such treatment. In some embodiments, for example, the anti-SARS-COV-2 S protein antibodies of the invention would be administered to a subject at risk of developing a disorder associated with a betacoronavirus infection (e.g., a subject residing or traveling to a geographical location in which a betacoronavirus outbreak is found). Accordingly, desirable effects of treatment include, but are not limited to, preventing occurrence of a disease or disorder, such as a disorder associated with a betacoronavirus infection (e.g., COVID-19, SARS, or MERS). Other desirable effects of treatment may include preventing recurrence of disease, alleviation of symptoms, diminishment of any direct or indirect pathological consequences of the disease, decreasing the rate of disease progression, amelioration or palliation of the disease state, and improved prognosis.

As used herein, "administering" is meant a method of giving a dosage of a compound (e.g., an anti-SARS-COV-2 S protein antibody of the invention or a nucleic acid encoding an anti-SARS-COV-2 S protein antibody of the invention) or a composition (e.g., a pharmaceutical composition, e.g., a pharmaceutical composition including an anti-SARS-COV-2 S protein antibody of the invention) to a subject. The compositions utilized in the methods described herein can be administered or formulated for administration, for example, intravenously, intranasally, by inhalation, intramuscularly, intradermally, percutaneously, intraarterially, intraperitoneally, intralesionally, intracranially, intraarticularly, intraprostatically, intrapleurally, intratracheally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated). Preferably, the compound (e.g., anti-SARS-COV-2 S protein antibody of the invention) or composition (e.g., pharmaceutical composition comprising an anti-SARS-COV-2 S protein antibody of the invention) is administered intravenously or formulated for intravenous administration. In some embodiments, the compound (e.g., anti-SARS-COV-2 S protein antibody of the invention) or composition (e.g., pharmaceutical composition comprising an anti-SARS-COV-2 S protein antibody of the invention) is administered intranasally or formulated for intranasal administration.

As used herein, the term "vector" is meant to include, but is not limited to, a nucleic acid molecule (e.g., a nucleic acid molecule that is capable of transporting another nucleic acid to which it has been linked), a virus (e.g., a lentivirus or an adenovirus, e.g., a recombinant adeno-associated virus (rAAV)), cationic lipid (e.g., liposome), cationic polymer (e.g., polysome), virosome, nanoparticle, or dentrimer. Accordingly, one type of vector is a viral vector, wherein additional DNA segments (e.g., transgenes, e.g., transgenes encoding the heavy and/or light chain genes of an anti-SARS-COV-2 S protein antibody of the invention) may be ligated into the viral genome, and the viral vector may then be administered (e.g., by electroporation, e.g., electroporation into muscle tissue) to the subject in order to allow for transgene expression in a manner analogous to gene therapy. Another type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids.

As used herein, the term "antibacterial agent" refers to a therapeutic agent capable of inhibiting, slowing the progression, and/or ameliorating the symptoms of a bacterial infection. A "bacterial infection" refers to the pathogenic growth of a bacterium. A bacterial infection can be any situation in which the presence of a bacterial population is damaging to a host body. Thus, a subject is "suffering" from a bacterial infection when an excessive amount of a bacterial population is present in or on the subject's body, or when the presence of the bacterial infection is damaging the cells or other tissue of the subject. An antibacterial agent may be selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin clavulanate, ampicillin/sulbactam, piperacillin/tazobactam, ticarcillin/clavulanate, bacitracin, colistin, polymyxin b, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (tmp-smx), sulfonamidochrysoidine, demeclocycline, doxycycline, minocycline, oxytetracycline, tetracycline, clofazimine, dapsone, capreomycin, cycloserine, ethambutol (bs), ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim. In particular embodiments, the antibacterial agent is azithromycin. The preceding list is meant to be exemplary of antibacterial agents known to one skilled in the art for the treatment of infection and is not meant to limit the scope of the invention.

As used herein, the term "antifungal agent" refers to a therapeutic agent capable of inhibiting, slowing the progression, or ameliorating the symptoms of a fungal infection. A "fungal infection" refers to the pathogenic growth of a fungus. A fungal infection can be any situation in which the presence of a fungal population is damaging to a host body. Thus, a subject is "suffering" from a fungal infection when an excessive amount of a fungal population is present in or on the subject's body, or when the presence of the fungal infection is damaging the cells or other tissue of the subject. An antifungal agent may be selected from rezafungin, anidulafungin, caspofungin, micafungin, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, triazoles, albaconazole, efinaconazole, epoxiconazole, fluconazole, isavuconazole, itraconazole, posaconazole, propiconazole, ravuconazole, terconazole, voriconazole, abafungin, amorolfin, butenafine, naftifine, terbinafine, ciclopirox, flucytosine, griseofulvin, tolnaftate, or undecylenic acid.

As used herein, the term "antiparasitic agent" refers to a therapeutic agent capable of inhibiting, slowing the progression, or ameliorating the symptoms of a parasitic infection. A "parasitic infection" refers to the pathogenic growth of a parasite. A parasitic infection can be any situation in which the presence of a parasite population is damaging to a host body. Thus, a subject is "suffering" from a parasitic infection when an excessive amount of a parasite population is present in or on the subject's body, or when the presence of the parasitic infection is damaging the cells or other tissue of the subject. An antiparasitic agent may be selected from hydroxychloroquine or chloroquine.

As used herein, the term "antiviral agent" refers to a therapeutic agent capable of inhibiting, slowing the progression, or ameliorating the symptoms of a viral infection. A "viral infection" refers to the pathogenic growth of a virus. A viral infection can be any situation in which the presence of a viral population is damaging to a host body. Thus, a subject is "suffering" from a viral infection when an excessive amount of a viral population is present in or on the subject's body, or when the presence of the viral infection is damaging the cells or other tissue of the subject. An antiviral agent may be selected from remdesivir, favilavir, OYA1, lopinavir, ritonavir, galidesivir, EIDD-1931, EIDD-2801, or SNG001 (inhaled interferon-beta-1a).

II. Compositions and Methods

In one aspect, the invention is based, in part, on anti-SARS-COV-2 S protein antibodies. Antibodies of the invention are useful, for example, for treating a subject having, or at risk of developing, a disorder associated with an a betacoronavirus infection.

A. Anti-SARS-COV-2 S Protein Antibodies

The invention provides, in one aspect, isolated antibodies that bind to the receptor binding domain (RBD) of the S protein of SARS-COV-2, for example, at an epitope between amino acid residues 439-541 of SARS-COV-2 S protein (SEQ ID NO: 1). In some embodiments, the antibody binds to an epitope between amino acid residues 439-498 of SARS-COV-2 S protein (SEQ ID NO: 1). In further embodiments, the antibody binds to an epitope including at least one (e.g., 1, 2, or 3) of amino acid residues Y449, F456, and Y489 of SARS-COV-2 S protein (SEQ ID NO: 1). In some embodiments, the epitope further includes at least one of amino acid residues Y453, A475, and Q493 of SARS-COV-2 S protein (SEQ ID NO: 1). In some embodiments, the antibody binds to an epitope comprising at least one of amino acid residues Y449, Y453, F456, A475, Y489, and Q493 of SARS-COV-2 S protein (SEQ ID NO: 1). In some embodiments, the antibody binds to an epitope including at least two (e.g., 2 or 3) of amino acid residues Y499, F456, and Y489 of SARS-COV-2 S protein (SEQ ID NO: 1). In some embodiments, the antibody binds to an epitope including amino acid residues Y449, F456, and Y489 of SARS-COV-2 S protein (SEQ ID NO: 1). In some embodiments, the epitope further includes amino acid residues Y453, A475, and Q493 of SARS-COV-2 S protein (SEQ ID NO: 1). In some embodiments, the antibody binds to an epitope comprising the amino acid residues Y449, Y453, F456, A475, Y489, and Q493 of SARS-COV-2 S protein (SEQ ID NO: 1). In some embodiments, the antibody binds to an epitope in the RBD core of SARS-COV-2 S protein (SEQ ID NO: 1).

In another aspect, the invention provides an isolated antibody that binds to SARS-COV-2 S protein, wherein the antibody includes the following complementarity determining regions (CDRs): (a) a CDR-H1 comprising the amino acid sequence of GFSFSSYGMH (SEQ ID NO: 2); (b) a CDR-H2 comprising the amino acid sequence of WYDGSDK (SEQ ID NO: 3); (c) a CDR-H3 comprising the amino acid sequence of ARERYFDWIFDF (SEQ ID NO: 4), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2-4, and/or (ii) one, two, or three amino acid substitutions relative to the amino acid sequence of any one of SEQ ID NOs: 2-4.

In another aspect, the invention provides an isolated antibody that binds to SARS-COV-2 S protein, wherein the antibody includes the following CDRs: (a) a CDR-L1 comprising the amino acid sequence of RASQSVSSSYLA (SEQ ID NO: 5); (b) a CDR-L2 comprising the amino acid sequence of GASSRAT (SEQ ID NO: 6); and (c) a CDR-L3 comprising the amino acid sequence of QQYGSSWT (SEQ ID NO: 7), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 5-7, and/or (ii) one, two, or three amino acid substitutions relative to the amino acid sequence of any one of SEQ ID NOs: 5-7.

In some instances, the anti-SARS-COV-2 S protein antibodies may include the following heavy chain framework regions (FRs): (a) an FR-H1 comprising the amino acid sequence of QVQLVESGGGVVQPGRSLRLSCAAS (SEQ ID NO: 8); (b) an FR-H2 comprising the amino acid sequence of WVRQAPGKGLEWVAVI (SEQ ID NO: 9); (c) an FR-H3 comprising the amino acid sequence of YYADSVKGRFTISRDNSKNTLYLQLNSLRAED-TAIYYC (SEQ ID NO: 10); and (d) an FR-H4 comprising the amino acid sequence of WGQGTLVTVSS (SEQ ID NO: 11), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 8-11.

In some instances, the anti-SARS-COV-2 S protein antibodies may include the following light chain FRs: (a) an FR-L1 comprising the amino acid sequence of EIVLTQSPGTLSLSPGERATLSC (SEQ ID NO: 12); (b) an FR-L2 comprising the amino acid sequence of WYQQKPGQAPRLLIY (SEQ ID NO: 13); (c) an FR-L3 comprising the amino acid sequence of GIPDRFSGSGSGTDFTLTISRLEPEDFAVYYC (SEQ ID NO: 14); and (d) an FR-L4 comprising the amino acid sequence of FGQGTKVEIK (SEQ ID NO: 15), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12-15.

For example, the anti-SARS-COV-2 S protein antibody includes the following six CDRs: (a) a CDR-H1 comprising the amino acid sequence of GFSFSSYGMH (SEQ ID NO: 2); (b) a CDR-H2 comprising the amino acid sequence of WYDGSDK (SEQ ID NO: 3); (c) a CDR-H3 comprising the amino acid sequence of ARERYFDWIFDF (SEQ ID NO: 4); (d) a CDR-L1 comprising the amino acid sequence of RASQSVSSSYLA (SEQ ID NO: 5); (e) a CDR-L2 comprising the amino acid sequence of GASSRAT (SEQ ID NO: 6); and (f) a CDR-L3 comprising the amino acid sequence of QQYGSSWT (SEQ ID NO: 7), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2-7, and/or (ii) one, two, or three amino acid substitutions relative to the amino acid sequence of any one of SEQ ID NOs: 2-7. In some instances, the antibody includes the following four heavy chain FRs: (a) an FR-H1 comprising the amino acid sequence of QVQLVES-GGGVVQPGRSLRLSCAAS (SEQ ID NO: 8); (b) an FR-H2 comprising the amino acid sequence of WVRQAPGKGLEWVAVI (SEQ ID NO: 9); (c) an FR-H3 comprising the amino acid sequence of YYADSVKGRFTISRDNSKNTLYLQLNSLRAED-TAIYYC (SEQ ID NO: 10); and (d) an FR-H4 comprising the amino acid sequence of WGQGTLVTVSS (SEQ ID NO: 11), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 8-11. In some instances, the antibody includes the following four light chain FRs: (a) an FR-L1 comprising the amino acid sequence of EIVLTQSPGTLSLSPGERATLSC (SEQ ID NO: 12); (b) an FR-L2 comprising the amino acid sequence of WYQQKPGQAPRLLIY (SEQ ID NO: 13); (c) an FR-L3 comprising the amino acid sequence of GIPDRFSGSGSGTDFTLTISRLEPEDFAVYYC (SEQ ID NO: 14); and (d) an FR-L4 comprising the amino acid sequence of FGQGTKVEIK (SEQ ID NO: 15), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12-15.

In another aspect, the invention provides an isolated antibody that binds to SARS-COV-2 S protein, wherein the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 16; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 17; or (c) a VH sequence as in (a) and a VL sequence as in (b). In some instances, the antibody comprises (a) a heavy chain variable domain (VH) sequence of SEQ ID NO: 16, or a variant thereof having up to about 23 (e.g., about 1, about 2, about 3, about 4, about 5, about 6, about 7, about 8, about 9, about 10, about 11, about 12, about 13, about 14, about 15, about 16, about 17, about 18, about 19, about 20, about 21, about 22, or about 23) amino acid residue substitutions; (b) a light chain variable domain (VL) sequence of SEQ ID NO: 17, or a variant thereof having up to about 23 (e.g., about 1, about 2, about 3, about 4, about 5, about 6, about 7, about 8, about 9, about 10, about 11, about 12, about 13, about 14, about 15, about 16, about 17, about 18, about 19, about 20, about 21, about 22, or about 23), amino acid substitutions; or (c) a VH sequence as in (a) and a VL sequence as in (b). In particular instances, the antibody is the exemplary anti-SARS-COV-2 S protein antibody MAb362.

In one aspect, the invention also provides isolated antibodies that bind to the RBD of the SARS-CoV-2 S protein that are also capable of cross-reacting with the SARS-COV S protein. In some embodiments, the anti-SARS-COV-2 S protein antibody binds to the RBD of the S protein of SARS-COV at an epitope between amino acid residues 270-510 of SARS-COV S protein (SEQ ID NO: 18). In some embodiments, the anti-SARS-COV-2 S protein antibodies are capable of cross-reactivity with SARS-COV S protein. In some embodiments, the anti-SARS-COV-2 S protein antibodies bind to an epitope in the RBD core of SARS-COV S protein (SEQ ID NO: 18).

Antibodies that bind to SARS-COV-2 S protein of the invention may, for example, be monoclonal, human, humanized, or chimeric. For example, in some instances, the antibody is monoclonal. In some instances, the antibody is a human antibody. In some instances, the antibody is a human monoclonal antibody. The antibodies can be full-length antibodies or antibody fragments thereof (e.g., an antibody fragment that binds S protein). The antibody fragment may be selected from the group consisting of Fab, Fab'-SH, Fv, scFv, and (Fab') 2 fragments. In some instances, the antibody is an IgG antibody (e.g., an IgG1 antibody). An antibody of the invention may have a half-life of ≥3 days (e.g., ≥1 week, e.g., ≥2 weeks, e.g., ≥1 month, e.g., ≥2 months, e.g., ≥3 months, e.g., ≥4 months, e.g., ≥5 months, e.g., ≥6 months).

The anti-SARS-COV-2 S protein antibodies of the invention may be any immunoglobulin antibody isotype, including IgG, IgE, IgM, IgA, or IgD (e.g., IgG or IgA). Additionally, the anti-SARS-COV-2 S protein antibodies may be any IgG subtype (e.g., IgG1, IgG2a, IgG2b, IgG3, or IgG4). In particular embodiments, the anti-SARS-COV-2 antibodies are IgG1 antibodies. In some embodiments, the anti-SARS-Cov-2 S protein antibodies are IgA antibodies. IgA is an antibody that plays a crucial role in the immune function of mucous membranes. Subclasses of IgA antibodies include secretory IgA (sIgA) and dimeric IgA (dIgA). In some embodiments, the anti-SARS-COV-2 S protein antibody may be any IgA subtype (e.g., dIgA1, dIgA2, sIgA1, and sIgA2).

In one aspect, the invention provides an antibody (e.g., a monoclonal antibody) that competes for binding to a SARS-COV-2 S protein with an antibody that includes the following six CDRs: (a) a CDR-H1 comprising the amino acid sequence of GFSFSSYGMH (SEQ ID NO: 2); (b) a CDR-H2 comprising the amino acid sequence of WYDGSDK (SEQ ID NO: 3); (c) a CDR-H3 comprising the amino acid sequence of ARERYFDWIFDF (SEQ ID NO: 4); (d) a CDR-L1 comprising the amino acid sequence of RASQSVSSSYLA (SEQ ID NO: 5); (e) a CDR-L2 comprising the amino acid sequence of GASSRAT (SEQ ID NO: 6); and (f) a CDR-L3 comprising the amino acid sequence of QQYGSSWT (SEQ ID NO: 7), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2-7, and/or (ii) one, two, or three amino acid substitutions relative to the amino acid sequence of any one of SEQ ID NOs: 2-7. In one aspect, the invention provides an antibody (e.g., a monoclonal antibody) that competes for binding to a SARS-COV-2 S protein with an antibody that includes the following four heavy chain FRs: (a) an FR-H1 comprising the amino acid sequence of QVQLVESGGGVVQPGRSLRLSCAAS (SEQ ID NO: 8); (b) an FR-H2 comprising the amino acid sequence of WVRQAPGKGLEWVAVI (SEQ ID NO: 9); (c) an FR-H3 comprising the amino acid sequence of YYADSVKGRFTISRDNSKNTLYLQLNSLRAED-TAIYYC (SEQ ID NO: 10); and (d) an FR-H4 comprising the amino acid sequence of WGQGTLVTVSS (SEQ ID NO: 11), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 8-11.

In one embodiment, the invention provides an antibody (e.g., a monoclonal antibody) that competes for binding to an S protein of SARS-COV-2 with an antibody that comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 16; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 17; or (c) a VH sequence as in (a) and a VL sequence as in (b).

In one aspect, the invention provides an antibody (e.g., a monoclonal antibody) that competes for binding to the S protein of SARS-COV-2 with an antibody that binds to the S1 subunit of the S protein of SARS-COV-2. In certain embodiments, the antibody (e.g., a monoclonal antibody) competes for binding to the S protein of SARS-COV-2 with an antibody that binds to an epitope between amino acid residues 439-541 of SARS-COV-2 S protein (SEQ ID NO: 1). In some embodiments, the antibody (e.g., a monoclonal antibody) competes for binding to the S protein of SARS-COV-2 with an antibody that binds to an epitope between amino acid residues 439-498 of SARS-COV-2 S protein (SEQ ID NO: 1). In further embodiments, the antibody (e.g., a monoclonal antibody) competes for binding to the S protein of SARS-CoV-2 with an antibody that binds to an epitope including at least one of amino acid residues Y449, F456, and Y489 of SARS-COV-2 S protein (SEQ ID NO: 1). In some embodiments, the epitope further includes at least one of amino acid residues Y453, A475, and Q493 of SARS-COV-2 S protein (SEQ ID NO: 1). In some embodiments, the antibody binds to an epitope comprising at least one of amino acid residues Y449, Y453, F456, A475, Y489, and Q493 of SARS-COV-2 S protein (SEQ ID NO: 1). In some embodiments, the antibody (e.g., a monoclonal antibody) competes for binding to the S protein of SARS-CoV-2 with an antibody that binds to an epitope including amino acid residues Y449, F456, and Y489 of SARS-COV-2 S protein (SEQ ID NO: 1). In some embodiments, the epitope further includes amino acid residues Y453, A475, and Q493 of SARS-COV-2 S protein (SEQ ID NO: 1). In some embodiments, the antibody binds to an epitope comprising the amino acid residues Y449, Y453, F456, A475, Y489, and Q493 of SARS-COV-2 S protein (SEQ ID NO: 1).

In certain embodiments, labeled anti-SARS-COV-2 S protein antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In a further aspect, an anti-SARS-COV-2 S protein antibody according to any of the above embodiments may incorporate any of the features, singly or in combination, as described in Sections 1-7 below.

1. Antibody Affinity

In certain embodiments, an antibody provided herein may have a dissociation constant ($K_D$) of between about 0.01 nM and about 100 nM. In some instances, the antibody may have a $K_D$ of ≤10 UM, ≤1 μM, ≤100 nM, ≤10 nM, ≤1 nM, ≤0.1 nM, or ≤0.01 nM.

In one embodiment, an antibody provided herein may bind SARS-COV-2 S protein with a $K_D$ of between about 100 μM and about 100 nM (e.g., between about 5 nM and about 100 nM, between about 15 nM and about 100 nM, between about 25 nM and about 100 nM, between about 35 nM and about 100 nM, between about 45 nM and about 100 nM, between about 55 nM and about 100 nM, between about 65 nM and about 100 nM, between about 75 nM and about 100 nM, between about 85 nM and about 100 nM, or between about 95 nM and about 100 nM). In some embodiments, the antibody may bind SARS-CoV-2 S protein with a $K_D$ between about 1 nM and about 50 nM (e.g., between about 5 nM and about 50 nM, between about 8 nM and about 40 nM, between about 11 nM and about 30 nM, or between about 14 nM and about 20 nM). In particular embodiments, an antibody provided herein may bind SARS-COV-2 S protein with a $K_D$ of about 15 nM.

In one embodiment, an antibody provided herein may bind SARS-COV S protein with a $K_D$ of between about 10 pM and about 10 nM (e.g., between about 50 pM and about 10 nM, between about 100 pM and about 10 nM, between about 200 pM and about 10 nM, between about 300 pM and about 10 nM, between about 400 pM and about 10 nM, between about 500 pM and about 10 nM, between about 600 pM and about 10 nM, between about 700 pM and about 10 nM, between about 800 pM and about 10 nM, between about 900 pM and about 10 nM, between about 1 nM and about 10 nM, between about 2 nM and about 10 nM, between about 3 nM and about 10 nM, between about 4 nM and about 10 nM, between about 5 nM and about 10 nM, between about 6 nM and about 10 nM, between about 7 nM and about 10 nM, between about 8 nM and about 10 nM, or between about 9 nM and about 10 nM). In some embodiments, the antibody may bind SARS-COV-2 S protein with a $K_D$ between about 500 pM and about 1 nM (e.g., between about 500 pM and about 1 nM, between about 600 pM and about 1 nM, between about 700 pM and about 1 nM, between about 800 pM and about 1 nM, between about 900 pM and about 1 nM, between about 500 pM and about 980 pM, between about 600 pM and about 940 pM, between about 700 pM and about 920 pM, between about 800 pM and about 910 pM, or between about 850 pM and about 900 pM). In particular embodiments, an antibody provided herein may bind SARS-COV S protein with a $K_D$ of about 870 pM.

In one embodiment, $K_D$ is measured using a BIACORE® surface plasmon resonance assay. For example, an assay using a BIACORE®-3000 (BIAcore, Inc., Piscataway, NJ) is performed at 25° C. with immobilized antigen CM5 chips at ~25 to ~100 response units (RU) of MAb362 (18 ng). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Various concentrations of soluble recombinant SARS-COV and SARS-COV-2 S protein RBD antigen ranging from 6.25 nM to 100 nM is injected at a flow rate of 30 μl/minute. An association step of 600 s was followed by a dissociation step of 180 s, and the final dissociation step was 1200 s. Regeneration of the sensor chip is accomplished using 3 M $MgCL_2$. Association rates ($k_{on}$) and dissociation rates ($k_{off}$) are calculated using a simple one-to-one Langmuir binding model (BIACORE® T200 Evaluation Software version 3.0) by simultaneously fitting the association and dissociation sensorgrams. The equilibrium dissociation constant ($K_D$) is calculated as the ratio $k_{on}/k_{off}$. See, for example, Chen et al., *J. Mol. Biol.* 293:865-881 (1999). If the on-rate exceeds $10^6 M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In another embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [125]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (Tween® 20) in PBS. When the plates have dried, 150 μl/well of scintillant (MICROSCINT™-20; Packard) is added, and the plates are counted on a TOPCOUNT™ gamma counter (Packard) for ten minutes. Concentrations of each Fab that give less than or equal to 20% of maximal binding are chosen for use in competitive binding assays.

2. Inhibition of Angiotensin-Converting Enzyme 2 Receptor Binding

In certain embodiments, an antibody provided herein is an antibody capable of inhibiting the binding of SARS-COV-2 S protein to ACE2 receptor on a cell. In some instances, the antibody of the invention is capable of inhibiting S protein binding to ACE2 receptor by at least 20% (e.g., about 25%, about 30%, about 40%, about 50%, about 55%, about 60%, about 65%, about 70%, about 75%, about 80%, about 85%, about 90%, about 95%, or about 100%). In some embodiments, the antibody of the invention is capable of inhibiting SARS-COV-2 S protein binding to ACE2 receptor by between about 20% and 100% (e.g., between about 20% and about 40%, between about 35% and about 50%, between about 45% and about 60%, between about 55% and about 70%, between about 65% and about 80%, between about 75% and about 90%, or between about 85% and about 100%). In some embodiments, an antibody provided herein is an antibody capable of inhibiting the binding of SARS-COV-2 S protein to ACE2 receptor on a cell by between 60% and 100% (e.g., between about 65% to about 95%, between about 70% to about 90%, between about 75% to about 85%, or between about 82% and about 84%). In particular embodiments, the antibody of the invention is capable of inhibiting SARS-COV-2 S protein binding the ACE2 receptor by at least 83% (e.g., at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100%) at a concentration of 333 nM. In some embodiments, the anti-SARS-COV-2 antibody of the invention is capable of inhibiting the binding of SARS-COV-2 S protein to ACE2 receptor on a cell with an $EC_{50}$ of between about 1 nM and 100 nM. (e.g., between about 5 nM and about 100 nM, between about 15 nM and about 100 nM, between about 25 nM and about 100 nM, between about 35 nM and about 100 nM, between about 45 nM and about 100 nM, between about 55 nM and about 100 nM, between about 65 nM and about 100 nM, between about 75 nM and about 100 nM, between about 85 nM and about 100 nM, or between about 95 nM and about 100 nM). In some embodiments, an antibody provided herein is an antibody capable of inhibiting the binding of SARS-COV-2 S protein to ACE2 receptor on a cell with an $EC_{50}$ of between about 1 nM and about 60 nM (e.g., between about 5 nM and about 60 nM, between about 15 nM and about 55 nM, between about 25 nM and about 45 nM, or between about 35 nM and about 40 nM). In particular embodiments, an antibody provided herein is capable of inhibiting the binding of SARS-COV-2 S protein to ACE2 receptor on a cell with an $EC_{50}$ of about 40 nM. In any of the above embodiments, binding inhibition may be measured by an in vitro flow cytometry binding inhibition assay, as described herein.

3. Neutralization of SARS-COV-2

In certain embodiments, an antibody provided herein is an antibody capable of neutralizing SARS-COV-2. Neutralization can occur in several ways, for example, the antibody may block viral binding to a receptor (e.g., a SARS-COV-2 S protein binding to an ACE2 receptor), block viral uptake into the cell, prevent uncoating of the genome in an endosome, and/or cause aggregation of the virus particles. Neutralization of a virus by an antibody (e.g., an anti-SARS-COV-2 S protein antibody) may be measured by a plaque reduction neutralization test (PRNT) that quantifies the titer of neutralizing antibodies for a virus. Other methods, such as hemagglutination and commercial enzyme immunoassays may be used to measure antibody neutralization.

In one aspect, an anti-SARS-COV-2 antibody provided herein is an antibody capable of neutralizing SARS-COV-2 with an $EC_{50}$ of between about 0.1 μg/mL and about 100 μg/mL. In some embodiments, an anti-SARS-COV-2 antibody provided herein is an antibody capable of neutralizing SARS-COV-2 with an $EC_{50}$ of between about 1 μg/mL and about 10 μg/mL (e.g., about 1.5 g/mL, about 2 μg/mL, about 2.5 μg/mL, about 3 μg/mL, about 3.5 μg/mL, about 4 μg/mL, about 4.5 μg/mL, about 5 μg/mL, about 5.5 μg/mL, about 6 μg/mL, about 6.5 μg/mL, about 7 μg/mL, about 7.5 μg/mL, about 8 μg/mL, about 8.5 μg/mL, about 9 μg/mL, or about 9.5 μg/mL). In some embodiments, an anti-SARS-COV-2 antibody provided herein is an antibody capable of neutralizing SARS-COV-2 with an $EC_{50}$ of about 5 μg/mL. In preferred embodiments, neutralization of SARS-COV-2 by an anti-SARS-COV-2 antibody provided herein is measured by a PRNT. In certain embodiments, an anti-SARS-COV-2 antibody provided herein is an antibody capable of cross-neutralization of SARS-COV-2 and SARS-COV.

4. Antibody Fragments

In certain embodiments, an antibody provided herein is an antibody fragment. Antibody fragments include, but are not limited to, Fab, Fab', Fab'-SH, $F(ab')_2$, Fv, and scFv fragments, which are known in the art. Also included are diabodies, which have two antigen-binding sites that may be bivalent or bispecific, as is known in the art. Triabodies and tetrabodies are also known. Single-domain antibodies are also antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells (e.g., *E. coli* or phage), as described herein.

5. Chimeric and Humanized Antibodies

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

6. Human Antibodies

In certain embodiments, an antibody provided herein is a human antibody (e.g., a human monoclonal antibody (HuMAb), e.g., an anti-SARS-COV-2 S protein HuMAb). Human antibodies can be produced using various techniques known in the art.

In some instances, human antibodies are obtained by cloning the heavy and light chain genes directly from human B cells obtained from a human subject. The B cells are separated from peripheral blood (e.g., by flow cytometry, e.g., FACS), stained for B cell marker(s), and assessed for antigen binding. The RNA encoding the heavy and light chain variable regions (or the entire heavy and light chains) is extracted and reverse transcribed into DNA, from which the antibody genes are amplified (e.g., by PCR) and sequenced. The known antibody sequences can then be used to express recombinant human antibodies against a known target antigen (e.g., SARS-COV-2 S protein).

In some instances, human antibodies may be prepared by administering an immunogen (e.g., SARS-COV-2 S protein) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. Human variable regions from intact antibodies generated by such animals may be further modified, for example, by combining with a different human constant region.

In some instances, human antibodies can also be made by hybridoma-based methods, as described in further detail below. Human myeloma and mouse-human heteromyeloma cell lines for the production of human monoclonal antibodies have been described.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

7. Antibody Variants

In certain embodiments, amino acid sequence variants of the anti-SARS-COV-2 S protein antibodies of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process, and/or residues that contact antigen, with the resulting variant VH or VL being tested for binding affinity. Affinity maturation by constructing and reselecting from secondary libraries is known in the art. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity.

Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two, or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, And Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, alternations may be made to the Fc region of an antibody. These alterations can be made alone, or in addition to, alterations to one or more of the antibody variable domains (i.e., VH or VL regions) or regions thereof (e.g., one or more CDRs or FRs). The alterations to the Fc region may result in enhanced antibody effector functions (e.g., complement-dependent cytotoxicity (CDC)), for example, by increasing C1q avidity to opsonized cells. Exemplary mutations that enhance CDC include, for example, Fc mutations E345R, E430G, and S440Y. Accordingly, anti-SARS-CoV-2 S protein antibodies of the invention may contain one or more CDC-enhancing Fc mutations, which promote IgG hexamer formation and the subsequent recruitment and activation of C1, the first component of complement (see, e.g., Diebolder et al. *Science.* 343:1260-1263, 2014).

In certain embodiments, alterations of the amino acid sequences of the Fc region of the antibody may alter the half-life of the antibody in the host. Certain mutations that alter binding to the neonatal Fc receptor (FcRn) may extend half-life of antibodies in serum. For example, antibodies that have tyrosine in heavy chain position 252, threonine in position 254, and glutamic acid in position 256 of the heavy chain can have dramatically extended half-life in serum (see, e.g., U.S. Pat. No. 7,083,784).

B. Production of Human Antibodies to SARS-COV-2 S Protein

1. Immunizations

The present invention features human monoclonal antibodies (HuMAbs) that bind SARS-COV-2 S protein. Exemplary human monoclonal antibodies that bind S protein include MAb362.

Human monoclonal antibodies of the invention can be produced using a variety of known techniques, such as the standard somatic cell hybridization technique described by Kohler and Milstein, Nature 256:495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for generating hybridomas which produce human monoclonal antibodies of the invention is the murine system. Hybridoma production in the mouse is well known in the art, including immunization protocols and techniques for isolating and fusing immunized splenocytes.

In one embodiment, human monoclonal antibodies directed against SARS-COV-2 S protein are generated using transgenic mice carrying parts of the human immune system rather than the mouse system. In one embodiment, the invention employs transgenic mice, referred to herein as "HuMAb mice," which contain a human immunoglobulin gene miniloci that encodes unrearranged human heavy (μ and γ) and K light chain immunoglobulin sequences, together with targeted mutations that inactivate the endogenous u and K chain loci. Accordingly, the mice exhibit reduced expression of mouse IgM or K, and in response to immunization, the introduced human heavy and light chain transgenes undergo class switching and somatic mutation to generate high affinity human IgG K monoclonal antibodies.

To generate fully human monoclonal antibodies to SARS-COV-2 S protein, transgenic mice containing human immunoglobulin genes and inactivated mouse heavy and kappa light chain genes (Bristol-Myers Squib) can be immunized with a purified or enriched preparation of the SARS-COV-2 S protein antigen (e.g., the N-terminal adhesion domain of the SARS-COV-2 S protein) and/or cells expressing SARS-COV-2 S protein, as described, for example, by Lonberg et al. (1994) Nature 368 (6474): 856-859; Fishwild et al. (1996) Nature Biotechnology 14:845-851 and WO 98/24884. As described herein, HuMAb mice are immunized either with recombinant SARS-COV-2 S protein polypeptides or cell lines expressing S protein as immunogens. Alternatively, mice can be immunized with DNA encoding SARS-COV-2 S protein. Preferably, the mice will be 6-16 weeks of age (e.g., 6-10 weeks of age) upon the first infusion. For example, a purified or enriched preparation (10-100 μg, e.g., 50 μg) of the recombinant SARS-COV-2 S protein antigen can be used to immunize the HuMAb mice, for example, intraperitoneally. In the event that immunizations using a purified or enriched preparation of the SARS-COV-2 S protein antigen do not result in antibodies, mice can also be immunized with cells expressing SARS-COV-2 S protein polypeptides, e.g., a cell line, to promote immune responses.

In some instances, to generate fully human monoclonal antibodies to SARS-COV-2 S protein, transgenic mice containing human immunoglobulin genes and inactivated mouse heavy and kappa light chain genes (Bristol-Myers Squib) can be immunized with a purified or enriched preparation of a betacoronavirus S protein having a similar sequence and/or structural homology to SARS-COV-2 S protein (e.g., the N-terminal adhesion domain of a betacoronavirus S protein) and/or cells expressing a betacoronavirus S protein having similar sequence and/or structural homology to SARS-COV-2 S protein (e.g., SARS-COV S protein).

Cumulative experience with various antigens has shown that the HuMAb transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retro-orbital or facial vein bleeds. The plasma can be screened by ELISA (as described below), and mice with sufficient titers of anti-SARS-CoV-2 S protein human immunoglobulin can be used for fusions. Mice can be boosted intravenously with antigen 3 days before sacrifice and removal of the spleen.

2. Generation of Hybridomas Producing HuMAbs to SARS-COV-2 S Protein

To generate hybridomas producing human monoclonal antibodies to SARS-COV-2 S protein, splenocytes and lymph node cells from immunized mice can be isolated and fused to an appropriate immortalized cell line, such as a mouse myeloma cell line (e.g., P3X-AG8.653). The resulting hybridomas can then be screened for the production of antigen-specific antibodies. For example, single cell suspensions of splenic lymphocytes from immunized mice can be fused to SP2/0-AG8.653 non-secreting mouse myeloma cells (ATCC, CRL 1580) with 50% PEG (w/v). Cells can be plated at approximately $1\times10^5$ in flat bottom microtiter plate, followed by a two-week incubation in selective medium containing besides usual reagents 10% fetal Clone Serum, and 1×HAT (Sigma). After approximately two weeks, cells can be cultured in medium in which the HAT is replaced with HT. Individual wells can then be screened by ELISA for human anti-SARS-COV-2 S protein monoclonal IgG and IgA antibodies, or for binding to the surface of a betacoronavirus expressing S protein with similar sequence and/or structural homology to SARS-COV-2 S protein by, for example, FLISA (fluorescence-linked immunosorbent assay). Once extensive hybridoma growth occurs, medium can be observed usually after $10^{-14}$ days. The antibody secreting hybridomas can be re-plated, screened again, and, if still positive for human IgG, anti-SARS-COV-2 S protein monoclonal antibodies can be subcloned at least twice by limiting dilution. The stable subclones can then be cultured in vitro to generate antibody in tissue culture medium for characterization.

3. Generation of Transfectomas Producing HuMAbs to SARS-COV-2 S Protein

Human antibodies of the invention also can be produced in a host cell transfectoma using, for example, a combination of recombinant DNA techniques and gene transfection methods as is well known in the art. For example, in one embodiment, the gene(s) of interest, e.g., human antibody genes, can be ligated into an expression vector such as a eukaryotic expression plasmid. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes can be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells. Alternatively these cloned antibody genes can be expressed in other expression systems such as *E. coli* or in complete organisms or can be synthetically expressed.

4. Recombinant Generation of HuMAbs to SARS-COV-2 S Protein

Anti-SARS-COV-2 S protein antibodies of the invention (e.g., anti-SARS-COV-2 S protein antibody MAb362, or a variant thereof) may be produced using recombinant methods and compositions, for example, as described in U.S. Pat. No. 4,816,567. In one embodiment, isolated nucleic acid encoding an anti-SARS-COV-2 S protein antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell or lymphoid cell (e.g., Y0, NS0, Sp20 cell). In one embodiment, a method of making an anti-SARS-COV-2 S protein antibody is provided, wherein the method comprises culturing a host cell comprising a nucleic acid encoding the antibody, as provided above, in a culture medium under conditions suitable for expression of the antibody, and optionally recovering the antibody from the host cell (or host cell culture medium).

For recombinant production of an anti-SARS-COV-2 S protein antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria (e.g., *E. coli*), in particular when glycosylation and Fc effector function are not needed. In some embodiments, the host cell is a prokaryotic cell (e.g., an *E. coli* cell). After expression, the antibody or antibody fragment thereof may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells, and myeloma cell lines such as Y0, NS0, and Sp2/0.

The anti-SARS-COV-2 S protein antibodies having $V_H$ and $V_K$ sequences disclosed herein can be used to create new anti-SARS-COV-2 S protein antibodies by modifying the $V_H$ and/or $V_K$ sequences, or the constant region(s) thereto. Thus, in another aspect, the structural features of an anti-SARS-COV-2 S protein antibody, e.g., MAb362, are used to create structurally related anti-SARS-COV-2 S protein antibodies that retain at least one functional property of the antibodies, such as binding to the SARS-COV-2 S protein, or neutralizing SARS-COV-2 in vitro and/or in vivo. For example, one or more CDR regions of MAb362, or mutations thereof, can be combined recombinantly with known framework regions and/or other CDRs to create additional, recombinantly-engineered, anti-SARS-COV-2 S protein antibodies, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) can be used as the starting material to create a "second generation" sequence(s) derived from the original sequence(s) and then the "second generation" sequence(s) is prepared and expressed as a protein.

The functional properties of the altered antibodies can be assessed using standard assays available in the art and/or described herein, such as those set forth in the Examples (e.g., flow cytometry and binding assays).

In certain embodiments of the methods of engineering the new antibodies described herein, mutations can be introduced randomly or selectively along all or part of an anti-SARS-COV-2 S protein antibody coding sequence and the resulting modified anti-SARS-COV-2 S protein antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

C. Characterization of Human Monoclonal Antibodies to S Protein

Sequence information for human monoclonal antibodies of the invention can be ascertained using sequencing techniques which are well known in the art.

Similarly, affinity of the antibodies for SARS-COV-2 S protein can also be assessed using standard techniques. For example, BIACORE®-3000 can be used to determine the affinity of HuMAbs to SARS-COV-2 S protein. HuMAbs are captured on the surface of a BIACORE® chip (GE healthcare), for example, via amine coupling (Sensor Chip CM5). The captured HuMAbs can be exposed to various concentrations of SARS-COV-2 S protein in solution, and the $k_{on}$ and $k_{off}$ for an affinity ($K_D$) can be calculated, for example, by BIAevaluation software.

Human monoclonal antibodies of the invention can also be characterized for binding to SARS-CoV-2 S protein using a variety of known techniques, such as ELISA, Western blot, etc. Generally, the antibodies are initially characterized by ELISA. Briefly, microtiter plates can be coated with purified SARS-COV-2 S protein in PBS followed by incubation overnight at 4° C., and then blocked with irrelevant proteins such as bovine serum albumin (BSA) diluted in PBS. Hybridoma supernatant or purified anti-SARS-COV-2 S protein antibody is added to each well and incubated for 1-2 hours at room temperature. The plates are washed with PBS/TWEEN® 20 and then incubated with a goat-anti-human IgG Fc-specific polyclonal reagent conjugated to alkaline phosphatase for 1 hour at 37° C. After washing, the plates are developed with PNPP substrate, and analyzed. Preferably, mice which develop the highest titers will be used for fusions.

In some instances, an ELISA assay as described above can be used to screen for antibodies and, thus, hybridomas that produce antibodies that show positive reactivity with the S protein immunogen. Hybridomas that bind, preferably with high affinity, to SARS-COV-2 S protein can then be subcloned and further characterized. One clone from each hybridoma, which retains the reactivity of the parent cell (by ELISA), can then be chosen for making a cell bank, and for antibody purification.

In some instances, the antibodies are evaluated by a plaque reduction neutralization test (PRNT) (Schmidt et al. *J. Clin. Microbiol.* 4 (1): 61-66, 1976). A PRNT assay is used to quantify the titer of neutralizing antibody for a virus. The serum sample or solution of antibody (e.g., an anti-SARS-COV-2 S protein antibody) to be tested can be diluted and mixed with a viral suspension. The mixture can be incubated to allow the antibody to react with the virus. After incubation, the mixture is poured over a confluent monolayer of host cells. The surface of the cell layer can then be covered in a layer of agar or carboxymethyl cellulose to prevent indiscriminate spreading of the virus. The concentration of plaque forming units can be estimated by the number of plaques (regions of infected cells) formed after a few days. The concentration of serum to reduce the number of plaques by 50% compared to the serum free virus gives the measure of how much antibody is present or how effective it is. This measurement is denoted as the PRNT50 value, and can be determined as described in Ramakrishnan (World *J. Virol.* 5 (2): 85-86, 2016).

In other instances, competition assays may be used to identify an antibody that competes with an anti-SARS-COV-2 S protein antibody of the invention for binding to SARS-COV-2 S protein. In certain embodiments, such a competing antibody binds to the same epitope (e.g., a linear or a conformational epitope) that is bound by an anti-SARS-COV-2 S protein antibody of the invention. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized SARS-COV-2 S protein is incubated in a solution comprising a first labeled antibody that binds to SARS-COV-2 S protein and a second unlabeled antibody that is being tested for its ability to compete with the first antibody for binding to SARS-COV-2 S protein. The second antibody may be present in a hybridoma supernatant. As a control, immobilized SARS-COV-2 S protein is incubated in a solution comprising the first labeled antibody but not the second unlabeled antibody. After incubation under conditions permissive for binding of the first antibody to SARS-COV-2 S protein, excess unbound antibody is removed, and the amount of label associated with immobilized S protein is measured. If the amount of label associated with immobilized SARS-COV-2 S protein is substantially reduced in the test sample relative to the control sample, then that indicates that the second antibody is competing with the first antibody for binding to SARS-COV-2 S protein.

D. Pharmaceutical Compositions

In another aspect, the present invention provides a composition, e.g., a pharmaceutical composition, containing one or more (e.g., 1, 2, 3, or 4 or more) of the anti-SARS-COV-2 S protein human monoclonal antibodies (HuMAbHuMAbs), or antibody fragments thereof, of the present invention, e.g., formulated for treating a betacoronavirus infection in a subject (e.g., a SARS-COV-2 infection, a SARS-CoV infection, or a MERS-COV infection). The pharmaceutical compositions may be formulated together with a pharmaceutically acceptable carrier, excipient, or diluent. In some instances, the pharmaceutical compositions include two or more of the anti-SARS-COV-2 S protein HuMAbs of the invention. Preferably, each of the antibodies of the composition binds to a distinct, pre-selected epitope of SARS-CoV-2 S protein.

A pharmaceutical composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

Depending on the route of administration and the dosage, an anti-SARS-COV-2 antibody or a pharmaceutical composition thereof used in the methods described herein will be formulated into suitable pharmaceutical compositions to permit facile delivery. An anti-SARS-COV-2 antibody or a pharmaceutical composition thereof may be formulated to be administered intravenously (e.g., as a sterile solution and in a solvent system suitable for intravenous use), intranasally, by inhalation, intramuscularly, intradermally, intraarterially, intraperitoneally, intralesionally, intracranially, intraarticularly, intraprostatically, intrapleurally, intratracheally, intravitreally, intravaginally, intrarectally, topically, intratumorally, peritoneally, subcutaneously, subconjunctival, intravesicularlly, mucosally, intrapericardially, intraumbilically, intraocularally, orally (e.g., a tablet, capsule, caplet, gel cap, or syrup), topically (e.g., as a cream, gel, lotion, or ointment), locally, by injection, or by infusion (e.g., continuous infusion, localized perfusion bathing target cells directly, catheter, lavage, in cremes, or lipid compositions). Depending on the route of administration, an anti-SARS-COV-2 antibody or a pharmaceutical composition thereof may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice. In certain embodiments, an anti-SARS-COV-2 antibody or a pharmaceutical composition thereof may be formulated to be administered intravenously (e.g., as a sterile solution and in a solvent system suitable for intravenous use). In some embodiments, an anti-SARS-COV-2 antibody or a pharmaceutical composition thereof may be formulated to be administered intranasally (e.g., as an aerosol, in a nanoparticle such as a liposome, or in a solvent system suitable for intranasal use, optionally including permeation enhancers, mucolytic agents, mucoadhesive agents, in situ gelling agents, and/or enzyme inhibitors). In some embodiments, an anti-SARS-COV-2 antibody or a pharmaceutical composition thereof may be formulated to be administered by inhalation (e.g., as a dry powder).

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions of the invention also can be administered in combination therapy, i.e., combined with other agents. For example, the combination therapy can include a composition of the present invention with at least one or more additional therapeutic agents as necessary for the particular indication (e.g., COVID-19, SARS, or MERS) being treated. In some embodiments, the one or more additional therapeutic agents are a second therapeutic antibody, an antifungal agent, an antiviral agent, an antiparasitic agent, an antibacterial agent, or a combination thereof. In one embodiment, the one or more additional therapeutic agents comprise an antiviral agent (e.g., remdesivir, favilavir, OYA1, lopinavir, ritonavir, galidesivir, EIDD-1931, EIDD-2801, or SNG001 (inhaled interferon-beta-1a). In some embodiments, one or more therapeutic agents comprise an antiparasitic agent (e.g., hydroxychloroquine or chloroquine). In certain embodiments, the one or more therapeutic agents comprise an antibacterial agent (e.g., azithromycin). In some embodiments, the one or more therapeutic agents comprise a second therapeutic antibody (e.g., gimsilumab).

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, such as TWEEN® 80. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, genes encoding the anti-SARS-COV-2 S protein antibodies of the invention may be delivered directly into the subject for expression rather than administering purified antibodies for prevention or therapy. For example, viral vectors, such as recombinant viruses, can be used to deliver the heavy and light chain genes. In one example, rAAV virus particles can be used to deliver anti-HIV monoclonal antibodies (Balazs et al. *Nature.* 481:81, 2012). Antibody genes could also be effectively delivered by electroporation of muscle cells with plasmid DNA containing heavy and/or light chain genes (e.g., VH and/or VL genes) (Muthumani et al. *Hum Vaccin Immunother.* 10:2253, 2013). Lentivirus vectors or other nucleic acids (e.g., RNA) capable of delivering transgenes could also be used to deliver antibody genes to establish serum antibody levels capable of prevention.

E. Therapeutic Methods and Compositions for Use

The anti-SARS-COV-2 S protein antibodies of the invention (e.g., HuMAbHuMAb anti-SARS-COV-2 S protein antibody MAb362 and variants thereof) and compositions containing the antibodies described herein can be used to treat a subject having a betacoronavirus (e.g., SARS-COV-2, SARS-COV, or MERS-COV) infection.

Betavoronaviruses are a species of coronavirus that cause respiratory tract infections with extrapulmonary involvement. Betavoronaviruses can be further categorized in four lineages, lineage A (include HCoV-OC43 and HCoV-HKU1), lineage B (including SARS-COV, SARS-COV-2), lineage C (including BtCoV-HKU4, BtCoV-HKU5, and MERS), and lineage D (including BtCoV-HKU9). These viruses are endemic in human populations and cause more severe disease in neonates, the elderly, and in individuals living with underlying illnesses, with a greater incidence of lower respiratory tract infection in these populations.

COVID-19 is a respiratory disease caused by an infection of the SARS-COV-2 coronavirus. SARS-COV-2 can spread from person to person (e.g., persons who are in close contact with one another (e.g., within six feet)) and through respiratory droplets produced when a person having been infected with the SARS-COV-2 virus coughs or sneezes and the droplets can come into contact (e.g., contact the nose, the mouth, the eyes, and/or be inhaled into the lungs) with another person thereby exposing the person to the virus. It may also be possible for a person to be exposed to SARS-COV-2 by touching a surface contaminated with the virus and then touching their own mouth, nose, or their eyes. The incubation period before onset of symptoms of COVID-19 is approximately 2-14 days after exposure to SARS-COV-2. Symptoms of the disease may include fever, cough, and difficulty breathing. Severity of symptoms may range from mild (e.g., no reported symptoms) to severe illness, including illness resulting in death. The elderly and persons of all ages with underlying health conditions are at higher risk of developing serious illness. A subject may be at risk of having COVID-19 if they have been exposed to someone who has been diagnosed as having the disease, recently travelled to a location experiencing an outbreak of COVID-19, is elderly, is immunocompromised, or has another comorbid condition as described herein. A subject can be diagnosed as having COVID-19 by one of skill in the art based on symptoms or a diagnostic test (e.g., an ELISA, lateral flow chromatographic immunoassays to detect SARS-COV-2 antibodies, or Abbot ID NOW™ platform).

Any of the anti-SARS-COV-2 S protein antibodies of the invention (e.g., HuMAb anti-SARS-COV-2 S protein antibody MAb362 and variants thereof) and compositions containing the antibodies can be used in a variety of in vivo therapeutic applications.

In one aspect, the invention features a method of treating a subject having a betacoronavirus infection (e.g., a SARS-COV-2 infection, a SARS-COV infection, or a MERS-COV infection) comprising administering a therapeutically effective amount of an antibody (e.g., a human monoclonal antibody or composition described herein) that specifically binds to SARS-COV-2 S protein, or a pharmaceutical composition thereof, thereby treating the subject.

In one embodiment, the invention features a method of treating a subject having a disorder associated with a betacoronavirus infection (e.g., SARS, COVID-19, or MERS) comprising administering a therapeutically effective amount of an antibody (e.g., a human monoclonal antibody or composition described herein) that specifically binds to SARS-COV-2 S protein, or a pharmaceutical composition thereof, thereby treating the subject.

In another aspect, an anti-SARS-COV-2 S protein antibody of the invention may be used in a method of treating a subject having a betacoronavirus infection (e.g., a SARS-COV-2 infection, a SARS-CoV infection, or a MERS-COV infection). In one embodiment, the method comprises administering to a subject having such a betacoronavirus infection (e.g., a SARS-COV-2 infection, a SARS-COV infection, or a MERS-COV infection) a therapeutically effective amount of one or more (e.g., 1, 2, 3, or 4 or more) anti-SARS-COV-2 S protein antibodies of the invention or a pharmaceutical composition including the one or more anti-SARS-COV-2 S protein antibodies.

In another aspect, an anti-SARS-COV-2 S protein antibody of the invention may be used in a method of treating a subject having a disorder associated with a betacoronavirus infection. In one embodiment, the method comprises administering to a subject having such a disorder associated with a betacoronavirus infection (e.g., SARS, COVID-19, or MERS) a therapeutically effective amount of one or more (e.g., 1, 2, 3, or 4 or more) anti-SARS-COV-2 S protein antibodies of the invention or a pharmaceutical composition including the one or more anti-SARS-COV-2 S protein antibodies.

In another aspect, an anti-SARS-COV-2 S protein antibody of the invention may be used in a method of treating a subject at risk of developing a betacoronavirus infection (e.g., treating a subject at risk of developing a betacoronavirus infection with an anti-SARS-COV-2 S protein antibody of the invention in order to prevent the subject from developing a betacoronavirus infection, such as an infection with SARS-COV-2, SARS-COV, or MERS-COV). In one embodiment, the method comprises administering to a subject at risk of developing a betacoronavirus infection a therapeutically effective amount of one or more (e.g., 1, 2, 3, or 4 or more) anti-SARS-COV-2 S protein antibodies of the invention or a pharmaceutical composition including the one or more anti-SARS-COV-2 S protein antibodies. In some instances, a subject can be considered at risk of developing a betacoronavirus infection if the subject is in a geographic region in which a betavoronavirus outbreak has occurred. In particular embodiments, a subject can be considered at risk of developing an infection with SARS-COV-2 if the subject is in a geographic region in which a SARS-COV-2 outbreak has occurred (e.g., in Asia, the Middle East, Africa, Central and South America, North America, Europe, Australia, India, and the United Kingdom). In other instances, subject can be considered at risk of developing a betacoronavirus infection if the subject had travelled, or will travel, to a geographic region in which a betacoronavirus outbreak has occurred.

In another aspect, an anti-SARS-COV-2 S protein antibody of the invention may be used in a method of treating a subject at risk of developing a disorder associated with a betacoronavirus infection (e.g., treating a subject at risk of developing a disorder associated with a betacoronavirus infection with an anti-SARS-COV-2 S protein antibody of the invention in order to prevent the subject from developing a disorder associated with a betacoronavirus infection, such as SARS, COVID-19, or MERS). In one embodiment, the method comprises administering to a subject at risk of developing a disorder associated with a betacoronavirus infection a therapeutically effective amount of one or more (e.g., 1, 2, 3, or 4 or more) anti-SARS-COV-2 S protein antibodies of the invention or a pharmaceutical composition including the one or more anti-SARS-COV-2 S protein antibodies. In some instances, a subject can be considered at risk of developing a disorder associated with a betacoronavirus infection if the subject is in a geographic region in which a betavoronavirus outbreak has occurred. In particular embodiments, a subject can be considered at risk of developing a disorder associated with a SARS-COV-2 infection (e.g., COVID-19) if the subject is in a geographic region in which a SARS-COV-2 outbreak has occurred (e.g., in Asia, the Middle East, Africa, Central and South America, North America, Europe, Australia, India, and the United Kingdom). In other instances, subject can be considered at risk of developing a disorder associated with a betacoronavirus infection if the subject had travelled, or will travel, to a geographic region in which a betacoronavirus outbreak has occurred.

In another aspect, an anti-SARS-COV-2 S protein antibody of the invention may be used in a method of treating a subject having or at risk of developing a betacoronavirus infection, where the betacoronavirus infection is with a lineage B betacoronavirus (e.g., SARS-COV-2 or SARS-COV) or a lineage C betacoronavirus (e.g., MERS-COV). In another embodiment, an anti-SARS-COV-2 S protein antibody of the invention may be used in a method of treating a subject that has or is presumed to have COVID-19. In another embodiment, an anti-SARS-COV-2 S protein antibody of the invention may be used in a method of treating a subject that has or is presumed to have SARS. In another embodiment, an anti-SARS-COV-2 S protein antibody of the invention may be used in a method of treating a subject that has or is presumed to have MERS.

Antibodies of the invention can be used either alone (i.e., as a monotherapy) or in combination with one or more additional therapeutic agents (i.e., as a combination therapy). For instance, an antibody of the invention may be co-administered with at least one or more additional therapeutic agents (e.g., a second therapeutic antibody, an antifungal agent, an antiviral agent, an antiparasitic agent, an antibacterial agent, or a combination thereof). In some embodiments, the one or more additional therapeutic agents are an antiviral agent (e.g., remdesivir, favilavir, OYA1, lopinavir, ritonavir, galidesivir, EIDD-1931, EIDD-2801, or SNG001 (inhaled interferon-beta-1a)). In some embodiments, the one or more additional therapeutic agents are an antiparasitic agent (e.g., hydroxychloroquine or chloroquine). In some embodiments, the one or more additional therapeutic agents are an antibacterial agent (e.g., azithromycin). In some embodiments, the one or more additional therapeutic agent is a second therapeutic antibody (e.g., gimsilumab). Such combination therapies encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-SARS-COV-2 S protein antibody (e.g., HuMAb anti-SARS-COV-2 S protein antibody MAb362) and administration of an additional therapeutic agent occur within about one month, or within about one, two or three weeks, or within about one, two, three, four, five, or six days, of each other.

An antibody of the invention, such as HuMAb anti-SARS-COV-2 S protein antibodyMAb362, (and/or any additional therapeutic agent) can be administered by any suitable means, including oral, parenteral, intrapulmonary, and intranasal, and, if desired for local treatment, intralesional administration. Parenteral infusions include intramuscular, intravenous, intraarterial, intraperitoneal, or subcutaneous administration. Preferably, the antibodies are administered by inhalation, intranasally, or intravenously. In certain instances, antibody genes (e.g., genes encoding any one or more of the anti-SARS-COV-2 S protein antibodies of the invention could be administered as a gene therapy to produce the one or more anti-SARS-COV-2 S protein antibodies in the subject using either DNA vectors or viral vectors (e.g., rAAV vectors). Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, such as diarrhea, the appropriate dosage of an antibody of the invention (when used alone or in combination with one or more other additional therapeutic agents) will depend on the type of disease to be prevented/treated, the duration of effective antibody concentration required, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. In some embodiments, a dosing schedule can include delivery, for example oral delivery, 1-3 days before a subject is at risk of developing a disorder associated with a betacoronavirus infection (e.g., −3 days, −2 days, and/or −1 day), on the day a subject is at risk of developing a disorder associated with a betacoronavirus infection (e.g., 0 day), and/or 1-3 days after a subject was at risk of developing a disorder associated with a betacoronavirus infection (e.g., +1 day, +2 days, and/or +3 days). In some embodiments, a dosing schedule can include delivery, for example oral delivery, on the day before a subject is at risk of developing a disorder associated with a betacoronavirus infection (e.g., −1 days), the day a subject is at risk of developing a disorder associated with a betacoronavirus infection (e.g., 0 day), and/or on the day after a subject is at risk of developing a disorder associated with a betacoronavirus infection (e.g., +1 day).

As a general proposition, the therapeutically effective amount of the anti-SARS-COV-2 S protein antibody administered to a human will be in the dose range of about 0.01 to about 500 mg/kg of patient body weight whether by one or more administrations. In some embodiments, the antibody is administered at a dose of about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.1 to about 10 mg/kg, or about 1 to about 10 mg/kg administered one (single administration) or more times (multiple administrations, e.g., daily administrations). In some embodiments, the antibody is administered at a dose of about 1 mg/kg to about 80 mg/kg, about 1 mg/kg to about 75 mg/kg, about 1 mg/kg to about 70 mg/kg, about 1 mg/kg to about 65 mg/kg, about 1 mg/kg to about 60 mg/kg, about 1 mg/kg to about 55 mg/kg, about 1 mg/kg to about 50 mg/kg, about 1 mg/kg to about 45 mg/kg, about 1 mg/kg to about 40 mg/kg, about 1 mg/kg to about 35 mg/kg, about 1 mg/kg to about 30 mg/kg, about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 5 mg/kg to about 80 mg/kg, about 10 mg/kg to about 80 mg/kg, about 15 mg/kg to about 80 mg/kg, about 20 mg/kg to about 80 mg/kg, about 25 mg/kg to about 80 mg/kg, about 30 mg/kg to about 80 mg/kg, about 35 mg/kg to about 80 mg/kg, about 40 mg/kg to about 80 mg/kg, about 45 mg/kg to about 80 mg/kg, about 50 mg/kg to about 80 mg/kg, about 55 mg/kg to about 80 mg/kg, about 60 mg/kg to about 80 mg/kg, about 65 mg/kg to about 80 mg/kg, or about 70 mg/kg to about 80 mg/kg. In one embodiment, the antibody administered to a human at a dose of about 1 mg/kg to 80 mg/kg. In one embodiment, the antibody is administered at a dose of about 1 mg/kg to 40 mg/kg. In one embodiment, an anti-SARS-COV-2 S protein antibody described herein is administered to a human at a flat dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.01 mg/kg to about 10 mg/kg. Such doses may be administered intermittently, for example, every week or every three weeks (e.g., such that the patient receives from about two to about twenty, or, for example, about six doses of the anti-SARS-COV-2 S protein antibody). An initial higher loading dose, followed by one or more lower doses may be administered. The progress of this therapy is easily monitored by conventional techniques and assays.

Actual dosage levels of the active ingredients in the pharmaceutical compositions of the present invention may be varied so as to obtain an amount of the active ingredient which is effective to achieve the desired therapeutic response and duration for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of compositions of the invention will be that amount of the compound which is the lowest dose effective to produce a therapeutic effect. Such an effective dose will generally depend upon the factors described above. If desired, the effective daily dose of therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. The liposomes may comprise one or more moieties which are selectively transported into specific cells or organs, thus enhance targeted drug delivery. Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

In some instances, the antibody-based therapy may be combined with an additional therapy for more efficacious treatment (e.g., additive or synergistic treatment) of the subject. Accordingly, subjects treated with antibodies of the invention can be additionally administered (prior to, simultaneously with, or following administration of a human antibody of the invention) with another therapeutic agent which enhances or augments the therapeutic effect of the human antibodies.

F. Diagnostic Methods, Purification Methods, and Related Compositions

In certain embodiments, any of the anti-SARS-COV-2 S protein antibodies of the invention are useful for in vitro or in vivo detection of the presence of SARS-COV-2 S protein in a biological sample from a subject (e.g., a mammal, e.g., a human). The term "detecting" as used herein encompasses quantitative or qualitative detection. In certain embodiments, a biological sample comprises a cell or tissue.

In one embodiment, an anti-SARS-COV-2 S protein antibody for use in a method of diagnosis (e.g., diagnosis of a betacoronavirus infection and/or a disorder associated with a betacoronavirus infection) or detection (e.g., detection of a betacoronavirus infection) is provided. In a further aspect, a method of detecting the presence of SARS-COV-2 S protein in a biological sample (e.g., a swab sample (e.g., a nasopharyngeal swab), a lavage sample (e.g., a bronchoalveolar lavage), a blood sample, a plasma sample, a sputum sample, a urine sample, a stool sample, or a mucosal secretion sample) is provided. In certain embodiments, the method comprises contacting the biological sample with an anti-SARS-COV-2 S protein antibody as described herein under conditions permissive for binding of the anti-SARS-COV-2 S protein antibody to SARS-COV-2 S protein, and detecting whether a complex is formed between the anti-SARS-COV-2 S protein antibody and SARS-COV-2 S protein. Such method may be an in vitro or in vivo method. In particular embodiments, detecting the presence of a SARS-COV-2 S protein in a biological sample from a subject identifies the subject as having a SARS-COV-2 infection.

In certain embodiments, labeled anti-SARS-COV-2 S protein antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In some embodiments, an anti-SARS-COV-2 S protein antibody are provided for use in a method of detection or purification of a betacoronavirus (e.g., a lineage B betacoronavirus (e.g., SARS-COV-2 or SARS-COV) or a lineage C betacoronavirus (e.g., MERS-COV). In other embodiments, the anti-SARS-CoV-2 S protein antibody is provided for use in a method of purifying a betacoronavirus S protein (e.g., a lineage B betacoronavirus S protein (e.g., SARS-COV-2 or SARS-COV S protein) or a lineage C betacoronavirus (e.g., MERS-COV S protein). In still other embodiments, an anti-SARS-COV-2 S protein antibody may be used in the purification of a SARS-COV-2 S protein (e.g., a SARS-COV-2 S protein or antigenic fragment thereof). In some embodiments, an anti-SARS-COV-2 S protein antibody may be used in the purification of a SARS-COV S protein (e.g., a SARS-COV S protein or antigenic fragment thereof). In some embodiments, an anti-SARS-COV-2 S protein antibody may be used in the purification of a MERS-COV S protein (e.g., a MERS-COV S protein or antigenic fragment thereof). In some embodiments, an anti-SARS-COV-2 S protein antibody is provided for use as an affinity reagent for a column purification method for SARS-COV-2 S protein, or an antigenic fragment thereof. As an affinity reagent for a column purification, an anti-SARS-COV-2 S protein antibody may be coupled (e.g., bound) to a solid support by any means known in the art (e.g., random coupling (e.g., with a free lysine group), oriented coupling (e.g., with carbohydrate sidechains or a free hinge region cysteine), and/or indirect coupling (e.g., by way of Protein A or G with cross linking). After the anti-SARS-COV-2 S protein is coupled to the solid support, a sample (e.g., a sample including a betacoronavirus, or a betacoronavirus S protein or an antigenic fragment thereof) may be passed over the column under conditions permissive for binding of the anti-SARS-COV-2 S protein antibody to the antigen. After the other sample components are washed away, the bound antigen may be stripped from the support, resulting in its purification from the original sample. Exemplary methods of affinity purification may be found, for example, in Bonner, P. (2018). *Protein Purification* (2nd ed. Taylor & Francis).

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. In some embodiments, the invention provides a kit comprising an antibody of the invention and a package insert with instructions for using the antibody for treating a subject having or at risk of developing a disorder associated with a betacoronavirus infection. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Also within the scope of the present invention are kits including anti-SARS-COV-2 S protein antibodies of the invention and, optionally, instructions for use. The kits can further contain one or more additional reagents, such as a second, different anti-SARS-COV-2 S protein antibody having a complementary activity that binds to an epitope on SARS-COV-2 S protein that is distinct from the epitope to which the first anti-SARS-COV-2 S protein antibody binds.

In some embodiments, diagnostic kits are provided that include anti-SARS-COV-2 S protein antibodies of the invention and, optionally, instructions for use of the antibody as an internal standard for a diagnostic test. In some embodiments, the diagnostic test is for detecting the presence of a SARS-CoV-2 S protein in a biological sample (e.g., a swab sample (e.g., a nasopharyngeal swab), a lavage sample (e.g., a bronchoalveolar lavage), a blood sample, a plasma sample, a sputum sample, a urine sample, a stool sample, or a mucosal secretion sample). In certain embodiments, the kit includes instructions for contacting the biological sample with an anti-SARS-COV-2 S protein antibody as described herein under conditions permissive for binding of the anti-SARS-COV-2 S protein antibody to SARS-COV-2 S protein, and detecting whether a complex is formed between the anti-SARS-COV-2 S protein antibody and SARS-COV-2 S protein. Such kits may be used for in vitro or in vivo detection of SARS-COV-2 S protein. In some embodiments, diagnostic kits are provided that include labeled anti-SARS-COV-2 S protein antibodies of the invention and, optionally, instructions for use of the labeled antibody for the detection of SARS-COV-2 S protein.

In some embodiments, the kits include anti-SARS-COV-2 S protein antibodies of the invention and, optionally, instructions for use of the antibody as an internal standard for a diagnostic test. In some embodiments, the kits include anti-SARS-COV-2 S protein antibodies of the invention and, optionally, an affinity purification column and/or instructions for use of the antibodies and the column in the purification of a betacoronavirus, SARS-COV-2 S protein, or SARS-COV-2 protein.

Other embodiments of the present invention are described in the following Examples. The present invention is further illustrated by the following examples which should not be construed as further limiting. The contents of Sequence Listing, figures and all references, patents and published patent applications cited throughout this application are expressly incorporated herein by reference.

III. EXAMPLES

The following are examples of the methods and compositions of the invention. It is understood that various other embodiments may be practiced, given the description provided herein.

Example 1. Materials and Methods

S Glycoprotein Expression and Purification

SARS-COV and SARS-COV-2 S glycoproteins were expressed and purified as previously described (Greenough et al. *J. Infect. Dis.* 194 (4): 507-514, 2005). Briefly, the amino acid sequence of the SARS-COV S glycoprotein (Urbani strain, National Center for Biotechnology Information [strain no. AAP13441]) and SARS-COV-2 S glycoprotein sequence (GeneBank: MN908947) were used to design a codon-optimized version for mammalian cell expression of the gene encoding the ectodomain of the S glycoproteins a.a. 1-1255 [S1-1255] for SARS-COV and a.a. 1-1273 [S1-1273] for SARS-COV-2, as described elsewhere (Wrapp, D. et al. *Science* 367:1260-1263, 2020). The synthetic gene was cloned into pcDNA3.1 Myc/His in-frame with c-Myc and 6-histidine epitope tags that enabled detection and purification. Truncated soluble S glycoproteins were generated by polymerase chain reaction (PCR) amplification of the desired fragments from the vectors encoding S1255 and S1273. The SARS-COV-2 RBD constructs carrying point mutation were generated by following the standard protocol from QUIKCHANGE® || XL Kit (Agilent). The cloned genes were sequenced to confirm that no errors had accumulated during the PCR process. All constructs were transfected into EXPIT cells using EXPIFECTAMINE™ 293 Transfection Kit (Thermo Fisher).

The plasmid of stabilized trimer of ectodomain of SARS-COV-2, NIAID VRC7471, and its expression and purification protocol was provided by Dr. Kizzmekia S. Corbett, PhD, at Vaccine Research Center of National Institute of Allergy and Infectious Diseases as part of large-scale production contract awarded to MassBiologics of UMMS (U24AI126683; Wrapp et al., *Science,* 367:1260-1263, 2020). In this construct, a gene encoding residues 1-1208 of SARS-COV-2 S glycoprotein sequence (GenBank: MN908947) was modified by adding two proline substitutions at residues 986 and 987, a "GSAS" (SEQ ID NO: 20) substitution at residues 682-685, a C-terminal T4 fibritin trimerization motif, an HRV3C protease cleavage site, a TWIN-STREP-TAG® and an 8×HisTag (SEQ ID NO: 21). The construct was cloned into the mammalian expression vector pCDNA 3.1. The construct was then transfected into EXPI293™ cells using EXPIFECTAMINE™ 293 Transfection Kit (Thermo Fisher). Protein was purified from using STREP-TACIN® resin (IBA) followed by size-exclusion chromatography using a SUPEROSE® 6 10/300 column (GE Healthcare).

All recombinant proteins were purified by immobilized metal chelate affinity chromatography using nickel-nitrilotriacetic acid (Ni-NTA) agarose beads. Proteins were eluted from the columns using 250 mmol/L imidazole and then dialyzed into phosphate buffered saline (PBS), pH 7.2 and checked for size and purity by sodium dodecyl sulfate polyacrylamide gel electrophoresis (SDS-PAGE). The stabilized trimer was also analyzed by high performance liquid chromatography (HPLC).

Generation of MAbs

Previously generated frozen hybridomas of anti-SARS-COV MAbs (Greenough et al. *J. Infect. Dis.,* 191:507-514, 2005) were recovered and scaled up. Hybridoma supernatants were screened for reactivity to the SARS-COV-2 S protein. Positive cell clones were selected for antibody sequencing. For MAb362, the heavy chain and light chain variable regions were amplified from hybridoma cells and cloned into an immunoglobulin G1 (IgG1) expression vector. Isotype switching was conducted using primers designed to amplify the variable heavy chain of the IgG antibody. Products were digested and ligated into a pcDNA 3.1 vector containing the heavy constant IgA1 chain. The vector was transformed in NEB5-α competent cells, and sequences were verified ahead of transient transfection. IgG1 and monomeric IgA1 antibodies were transfected in EXPI293T cells. Cell supernatants were harvested 5 days post transfection for antibody purification by protein A SEPHAROSE® for IgG and CAPTO™ L resin for IgA (GE Life Sciences). For dimeric IgA (dIgA), the heavy and light chain vectors were co-transfected with pcDNA-containing DNA for the connecting J chain. For secretory IgA1 (sIgA) expression, a pcDNA-vector containing gene sequence of secretory component was added to the transfection reaction in a 1:1 ratio.

Supernatant was run through a column of CAPTO™ L resin to capture the light chain of antibodies (GE Life Sciences). Purified antibodies were dialyzed against PBS before being moved onto size-exclusion chromatography on fast performance liquid chromatography to separate out the desired dimeric or secretory antibodies using a HILOAD™ 26/600 SUPERDEX™ 200-pg size-exclusion column (GE Life Sciences). The desired fractions were pooled, concentrated, and quality analyzed by SDS-PAGE and HPLC (Giuntini et al., *Infect. Immun.,* 86: e00355-18, 2018).

ELISA

Dilutions of purified MAbs were tested in ELISA for reactivity against recombinant S protein. Briefly, 96-well plates were coated with S proteins followed by incubation overnight at 4° C. The plates were blocked with 1% BSA with 0.05% TWEEN® 20 in PBS. Hybridoma supernatant or purified antibody diluted in 1×PBS plus 0.1% TWEEN® 20 and added to the 96-well plates and incubated for 1 hour at room temperature. The plates were stained with horseradish peroxidase-conjugated anti-kappa (Company Southern Biotech, #2060-05, 1:2000 dilution) for 1 h and developed using 3,3',5,5'-tetramethylbenzidine. Absorbance at an optical density at 450 nm (OD450) was measured on an EMAX® precision plate reader (Molecular Devices) using SOFTMAX® software. Absorbance at an optical density at 450 nm (OD450) was measured on an EMAX® precision plate reader (Molecular Devices) using SOFTMAX® Pro v4.3.1 LS.

ELISA-Based ACE2-Binding Assay

In all, 250 ng of ACE2 protein was coated on ELISA plates overnight at 4° C. After blocking with 1% BSA in PBS with 0.05% TWEEN® 20 for 1 h at room temperature, threefold of serial dilutions started from 10 μg $ml^{-1}$ of wild type and point mutations S protein were added into the plates and incubated for 1 h at room temperature. Then plates were stained with mouse-anti-Myc antibody (BD Pharmingen #551101), at 2 μg $ml^{-1}$ for 1 h, followed by horseradish peroxidase-conjugated goat anti-mouse (Jackson ImmnuoResearch #115-035-062, 1:2000 dilution) for 1 h and developed using 3,3',5,5'-tetramethylbenzidine. Absorbance at an optical density at 450 nm (OD450) was measured on an EMAX® precision plate reader (Molecular Devices) using SOFTMAX® Pro v4.3.1 LS.

Flow Cytometry-Based Receptor Binding Inhibition Assay

Vero E6 cells were harvested with PBS containing 5 mM ethylenediaminetetraacetic acid (EDTA) and aliquoted to $1\times10^6$ cells per reaction. Cells were pelleted then resuspended in PBS containing 10% FBS. Before mixing with the cells, Myc-tagged SARS-COV S1-590 or SARS-COV-2 S1-604 was incubated with the MAb at varying concentrations for 1 hour at room temperature, then the S protein was added to the Vero cells to a final concentration of 10 nM. The cells-S protein mixture was incubated for 1 h at room temperature. After incubation, the cell pellets were washed and then resuspended in PBS with 2% FBS and incubated with 10 μg/mL of mouse-anti-Myc antibody (BD Pharmingen #551101, 1:100 dilution) for 1 hour at 4° C. Pellets were washed again then subsequently incubated with a Phycoerythrin-conjugated anti-mouse IgG (Jackson Immuno Research) for 40 minutes at 4° C. Cells were washed twice then subjected to flow cytometric analysis using a MACSQUANT® Flow Cytometer (Miltenyi Biotec) and analyzed by MACSQUANTIFY™ Software v2.11 and FLOWJO™ v10. Binding was expressed as relative to cells incubated with S proteins only.

Pseudotyped Virus Neutralization Assay

Production of pseudotyped SARS-COV and SARS-COV-2 was performed as previously described (Wang et al., Antiviral Res. August: 91 (2): 187-94, 2011). Pseudovirus was generated employing an HIV backbone that contained a mutation to prevent HIV envelope glycoprotein expression and a luciferase gene to direct luciferase expression in target cells (pNL4-3.Luc.R-E-, obtained from Dr. Nathaniel Landau, NIH). SARS-COV and SARS-COV-2 spike protein was provided in trans by co-transfection of 293T cells with pcDNA-G with pNL4-3.Luc.R-E-. Supernatant containing virus particles was harvested 48-72 h post-transfection, concentrated using CENTRICON® 70 concentrators, aliquoted and stored frozen at −80 degree. Before assessing antibody neutralization, the 293T cells were transient transfected with 100 ng pcDNA-ACE2 each well in 96 well plates, and the cells were used for the pseudovirus infection 24 hours after transfection. A titration of pseudovirus was performed on 293T cells transiently transfected with human ACE2 receptor to determine the volume of virus need to generate 50,000 counts per second (cps) in the infection assay. The appropriate volume of pseudovirus was pre-incubated with varying concentrations of MAbs for 1 h at room temperature before adding to 293T cells expressing hACE2. 24 hours after the infection, the pseudovirus was replaced by fresh complete media, and 24 hours after media changing the infection was quantified by luciferase detection with BRIGHT-GLO™ luciferase assay (Promega) and read in a VICTOR$^{3}$™ plate reader (Perkin Elmer) for light production.

Plaque Reduction Neutralization Assay (PRNT)

Monoclonal antibody was serially diluted and incubated with ~70 plaque forming units of wild-type SARS-COV-2 (2019-nCOV/Victoria/1/2020), for 1 h at 37° C. in a humidified box. The virus/antibody mixture was then allowed to absorb onto monolayers of Vero E6 [(ECACC 85020206, European Collection of Authenticated Cell Cultures, UK] for 1 h at 37° C. in a humidified box. Overlay media [MEM (Life Technologies, California, USA) containing 1.5% carboxymethylcellulose (Sigma), 5% (v/v) fetal calf serum (Life Technologies) and 25 mM 4-(2-hydroxyethyl)-1-piperazineethanesulfonic acid buffer (Sigma)] was added and the 24-well plates were incubated in a humidified box at 37° C. for 5 days. Plates were fixed overnight with 20% (w/v) formalin/PBS, washed with tap water and stained with methyl crystal violet solution (0.2% v/v) (Sigma). The neutralizing antibody titers were defined as the amount of antibody (μg mL-1) resulting in a 50% reduction relative to the total number of plaques counted without antibody, by performing a Spearman-Kärber analysis (Dougherty and Harris, R J C Harris, Ed., 169, 1964) using MICROSOFT® EXCEL® v2016. An internal positive control for the PRNT assay was run using a sample of human MERS convalescent serum known to neutralize SARS-COV-2 (National Institute for Biological Standards and Control, United Kingdom).

Structural Modeling and Analyses.

Three crystal structures, 2GHW the complex of 80R: SARS-COV-RBD (Hwang, W. C., et al., *J. Biol. Chem.* 281 (45): 34610-34616, 2006), 2AJF the complex of ACE2: SARS-COV-RBD (Li, F., et al., *Science* 309 (5742): 1864-1868, 2005) and 6VW1 the complex of ACE2: SARS-COV-2-RBD (Shang, J., et al., *Nature* 581:221-224, 2020) were used as initial scaffolds in the determinations of the models of MAb362: SARS-COV-RBD and MAb362: SARS-COV-2-RBD. The amino acid sequence of MAb362 was aligned to the amino acid sequences of 80R bound SARS-COV-1 crystal structure (PDB: 2GHW). The point mutational studies of SARS-COV-2 RBD were used as restraints to guide the protein-protein docking of MAb362 against SARS-COV-2 RBD. The docking was performed using Glide (Schrödinger software suite v19-4) and Modeller v9.23. The highest scored docking pose that also best satisfied the mutational analysis was further optimized through 300 ns molecular dynamic (MD) simulations. The MD simulations were performed using DESMOND® (Schrödinger software suite v19-4) as previously described in, for example, Harder et al. (*J. Chem. Theory Comput.* 12:281-296, 2016) and Leidner et al. (*J. Chem. Theory Comput.* 14:2784-2796, 2018). The final frame of the MD simulations was used as the final structural model of MAb362-RBD complex.

The structural model of MAb362 binding to the SARS-COV-2 Spike trimer was based on 6VYB (Walls et al., *Cell* 180:281-292, 2020). All figures were made within PYMOL™ Molecular Graphics System v2.3.4 (Schrödinger). The residue van der Waals potential between the various complexes was extracted from the structures energies using the energy potential within DESMOND®.

Mutational Scanning to Identify MAb362-Binding Residues

SARS-COV-2 RBD residues predicted by modeling were individually mutated with a combination of alanine (to introduce a loss of interaction), tryptophan (to introduce a steric challenge), and lysine mutations to introduce charge using QUIKCHANGE™ II XL Kit (Agilent) or BIOXP™ 3200 System (SGI-DNA). The genes were cloned into RBD expression vectors and RBD proteins were purified as described above. Mutant RBD were confirmed intact expression on proteins gels, and the same amount of proteins were coated on the plate for ELISA assays.

Dilutions of purified MAbs were tested in ELISA for reactivity against mutant RBD proteins. In all, 96-well plates were coated with 100 μl of 5 μg of RBD mutants followed by incubation overnight at 4° C. The plates were blocked with 1% BSA with 0.05% TWEEN® 20 in PBS. Purified antibody diluted in 1×PBS plus 0.1% TWEEN® 20 and added to the 96-well plates and incubated for 1 h at room temperature. Plates were stained with alkaline phosphatase AFFINIPURE® goat anti-Human IgG (Jackson ImmunoResearch #109-055-098, 1:1000 dilution) for 1 h at room temperature. Alkaline phosphatase AFFINIPURE® goat anti-Mouse IgG (Jackson ImmunoResearch #115-055-003, 1:1000 dilution) was used to detect his tag in a separate ELISA to verify protein expression and coating. Plates were developed using p-Nitrophenyl Phosphate (Thermo Fisher Scientific). Absorbance at an optical density at 405 nm (OD405) was measured on an EMAX® precision plate reader (Molecular Devices) using SOFTMAX® Pro v4.3.1 LS. ELISAs assay was performed to determine binding of the MAbs to the mutant proteins compared with the wild type. Key residues were identified by RBD mutations that reduced $EC_{50}$ values relative to the wild-type RBD.

Affinity Determination

Bio-layer interferometry (BLI) with an OCTET® HTX (PALL/ForteBio) was used to determine the affinity of MAb362 IgG1 and IgA1 to the RBD of SARS-COV and SARS-COV-2 S protein. MAbs were added to 96 wells plates at 1000 nM and titrated 1:2 to 62 nM using PBS. RBD of SARS-COV, RBD, and ectodomains of SARS-COV-2 were biotinylated (Thermo Fisher) and immobilized on Streptavidin (SA) Biosensors (ForteBio) for 120 seconds at 1600 nM concentration. After a baseline step, MAb362-antigen binding rate was determined when the biosensors with immobilized antigen were exposed to MAb362 IgG1 or IgA1 at different concentrations for 120 seconds. Following association, the MAb362-antigen complex was exposed to PBS and the rate of the MAb362 dissociation from antigen was measured. Each assay was performed in triplicate. Binding affinities for MAb362 were calculated using association and dissociation rates with FORTEBIO® Data analysis software v8.1 (PALL).

Statistical Analysis

Statistical calculations were performed using Prism version 8.1.1 (GraphPad Software, La Jolla, CA). EC50 and IC50 values were calculated by sigmoidal curve fitting using nonlinear regression analysis.

Example 2. Anti-SARS-COV-2 S Protein HuMAb MAb362 Binds to Recombinant SARS-COV-2 and SARS-COV S Protein RBD

Introduction

Interventions for the prevention or treatment of COVID-19 are crucial for the ongoing outbreak. Pre- or post-exposure immunotherapies with neutralizing antibodies would be of great use by providing immediate mucosal immunity against SARS-COV-2.

The present examples describe the discovery of a cross-neutralizing human IgA monoclonal antibody, MAb362 IgA. This IgA antibody binds to SARS-COV-2 RBD with high affinity, competing at the ACE2 binding interface by blocking interactions with the receptor. MAb362 IgA neutralizes both pseudotyped SARS-COV and SARS-COV-2 in 293 cells expressing ACE2. The secretory IgA form of MAb326 also neutralizes authentic SARS-COV-2 virus. The results demonstrate that the IgA isotype may play a critical role in SARS-COV-2 neutralization.

Results

A panel of human MAbs that targets the RBD of the SARS-COV S glycoprotein, isolated from transgenic mice expressing human immunoglobulin genes, was previously developed and characterized (Greenough et al., *J. Infect. Dis.,* 191:507-514, 2005; Roberts et al., *J. Infect. Dis.,* 193:685-692, 2006). These transgenic mice contain human immunoglobulin genes and inactivated mouse heavy chain and kappa light chain genes (Bristol-Myers Squibb). Transgenic mice were immunized weekly with 10 mg of SARS-COV spike protein and adjuvants for 6-8 weeks. Hybridomas were generated following a standard fusion protocol. A panel of over 36 hybridomas were isolated based on various neutralization activities against SARS-COV with lead antibodies showing protective potency in mice and hamster models. To explore the possibility that some of the SARS-COV-specific hybridoma may have cross-reactivity against SARS-COV-2, these hybridomas were recovered and screened by ELISA against the SARS-COV-2 spike protein.

Figure 1B:
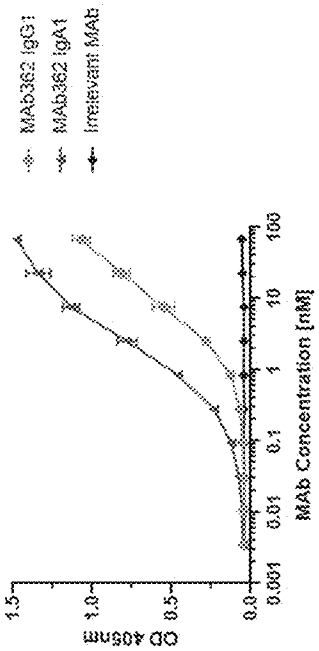
Figure 2A:
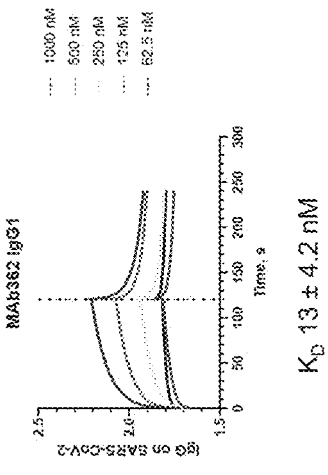
FIGS. 2A-2D are sensorgrams depicting the binding kinetics of MAb362 to the receptor binding domains (RBD) of the S protein of SARS-COV-2 and SARS-COV as determined by surface plasmon resonance (SPR).
Figure 2B:
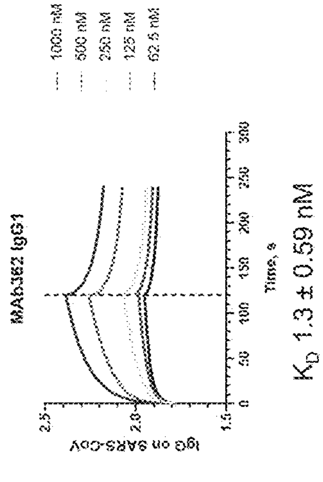
Figure 2C:
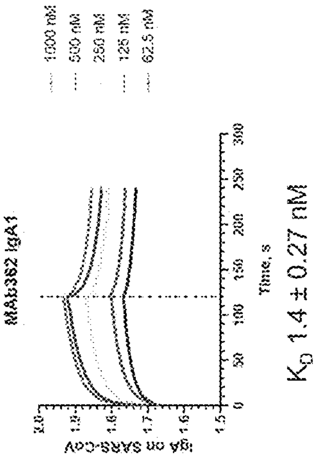
Figure 2D:
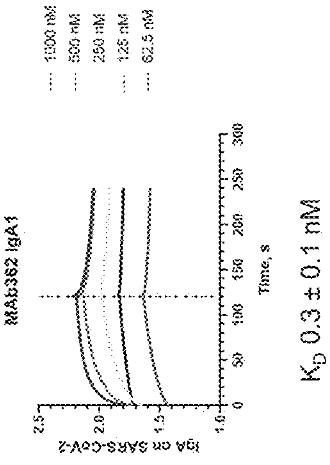

ELISA results show that MAb362 binds to the S1 subunit of the SARS-COV (amino acids 1-590) and SARS-COV-2 (amino acids 1-604) S protein. MAb362 binding to amino acid truncations of SARS-CoV S protein (270-510) and SARS-COV-2 S protein (319-541) indicates that the antibody binds specifically to the receptor binding domain (RBD) of the SARS-COV-2 S protein (FIG. 1). Antibody affinity was analyzed by surface plasmon resonance using recombinant SARS-COV S protein RBD (amino acid 270-510) and SARS-COV-2 S protein RBD (amino acid 319-541). MAb362 IgG shows high affinity for SARS-COV-2 S protein RBD with dissociation constant ($K_D$) value of 13±4.2 nM (FIG. 2A) and an affinity for SARS-COV S protein RBD with a $K_D$ of 1.3±0.59 nM (FIG. 2B). MAb362 IgA shows an affinity to SARS-COV S protein RBD with a $K_D$ of 1.4±0.27 nM (FIG. 2C). Affinity of MAb362 IgA with RBD of SARS-COV-2 is significantly higher ($K_D$=0.3±0.1 nM) than that of IgG due to a much slower dissociation rate as an IgA ($k_{off}$=$1.13\times10^{-3\pm1.06}\times10^{-4}$) compared to an IgG ($k_{off}$=$7.75\times10^{-5}\pm5.46\times10^{-5}$) (FIG. 2D).

Figures 9A, 9B, 9C, 9D, 9E, 9F, 9G, 9H:
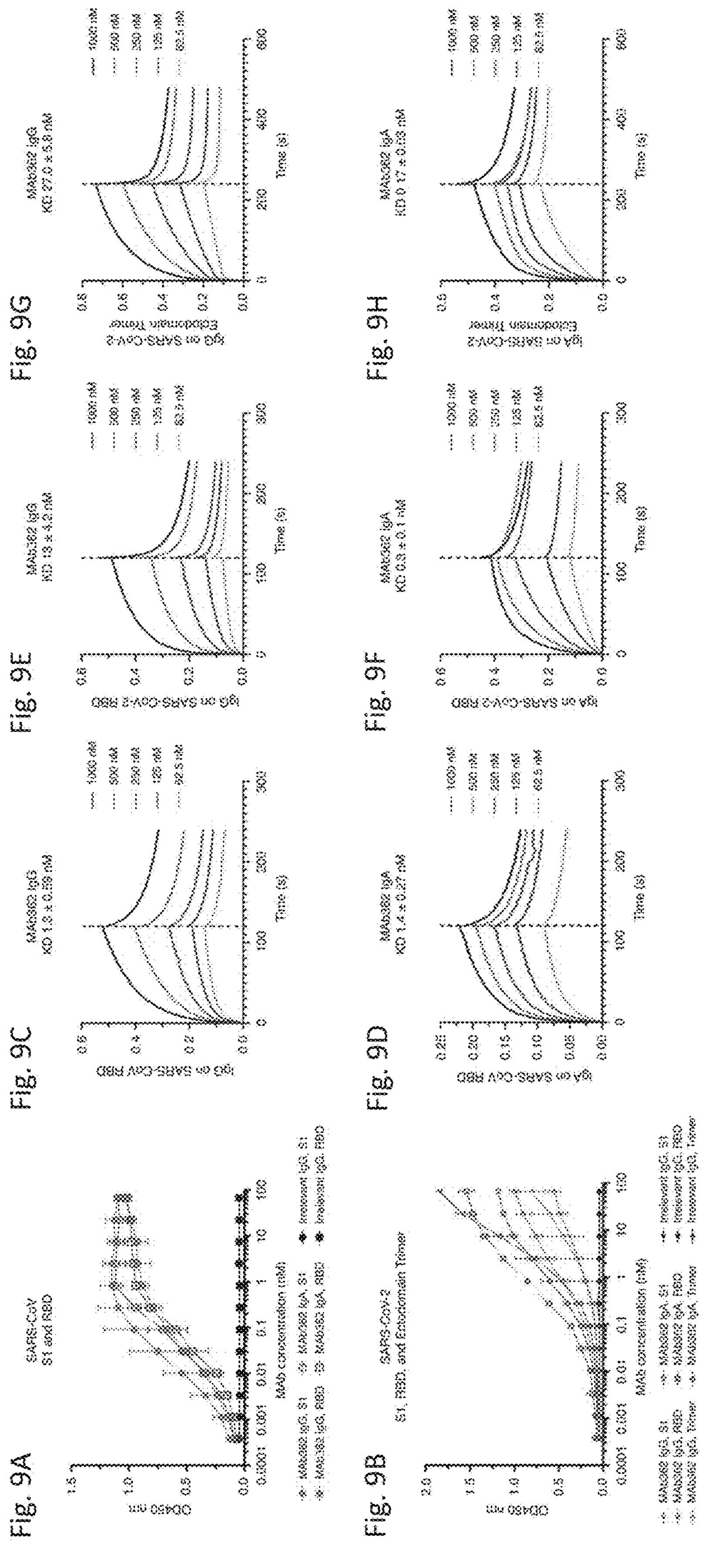
FIGS. 9A-9B are graphs depicting the enzyme linked immunosorbent assay (ELISA) binding curves of MAb362 to the S1 subunit of the SARS-COV (FIG. 9A) and SARS-COV-2 S (FIG. 9B) proteins, and fragments thereof.
FIGS. 9C-9F are sensorgrams depicting the binding kinetics of MAb362 to the RBD of the S protein of SARS-COV-2 and SARS-COV as determined by SPR.
FIG. 9G is a sensorgram depicting the binding kinetics of MAb362 IgG to a stabilized trimer form of the full ectodomain of the SARS-COV-2 spike protein.
FIG. 9H is a sensorgram depicting the binding kinetics of MAb362 IgA to a stabilized trimer form of the full ectodomain of the SARS-COV-2 spike protein.

While both IgG and IgA are expressed at the mucosa, IgA is more effective on a molar basis and thus the natural choice for mucosal passive immunization, as recently demonstrated in other mucosal infectious disease (Stoppato et al., *Vaccine,* 38:2333-239, 2020; Hu et al., *J. Pharm. Sci.,* 109:407-421, 2020). To further characterize the functionality of MAb362, variable sequences of MAb362 were cloned into expression vectors as either IgG or monomeric IgA isotypes. Both MAb362 IgG and IgA were assessed in ELISA-binding assays against the RBD of the S1 subunit for SARS-COV (S270-510) and SARS-COV-2 (S319-541) (FIGS. 9A and 9B). MAb362 IgA showed better binding activities, compared with its IgG counterpart against SARS-COV-2 S319-541 (FIG. 9B). Assessment of the binding kinetics was consistent with the ELISA-binding trends. The binding affinity of IgA with RBD of SARS-COV-2 is significantly higher (0.3 nM) than that of IgG (13 nM) due to a much slower dissociation rate as an IgA ($K_{off}$=$1.13\times10^{-3}\pm1.06\times10^{-4}$) compared to an IgG ($K_{off}$=$7.75\times10^{-5}\pm5.46\times10^{-5}$) (FIGS. 9E and 9F). Of note, MAb362 IgA and IgG showed similar binding affinity with SARS-COV S270-510 (FIGS. 9C and 9D).

To confirm binding results, the full ectodomain of spike was expressed including residues 1-1208 of SARS-COV-2 with stabilizing proline mutations and a C-terminal T4 fibritin trimerization motif as described recently (Wrapp et al., *Science,* 367:1260-1263, 2020). MAb362 IgA still showed better binding activities with the stabilized trimer form as compared with its IgG isotype in ELISA (FIG. 9B) and affinity assays. The binding affinity of MAb362 IgA with the ectodomain of SARS-COV-2 is 0.17 nM as compared with the 27 nM of IgG (FIGS. 9G and 9H).

Example 3. Virus Neutralization Assay

Neutralization of authentic SARS-COV-2 (Australian WHO strain) was preformed using a plaque reduction neutralization test (PRNT) as described in Example 1. PRNT50 was calculated by the method of Herr'n, Spearman and Karber (Hamilton et. al. *Environ. Sci. & Technol.* 11 (7): 714-719, 1977). MAb362 neutralized SARS-COV-2 with an $EC_{50}$ of ~5 µg/mL (Table 2).

TABLE 2

| Plaque reduction neutralization test (PRNT) | | | |
|---|---|---|---|
| Antibody | Buffer | Concentration (mg/mL) | PRNT50 |
| Irrelevant MAb | Phosphate Buffered Saline | 1.33 | <7 |
| MAb362 | Phosphate Buffered Saline | 0.142 | 27 |
| Positive Control | Serum | | 124 |

Example 4. Receptor Binding Inhibition Assay

Figure 3A:
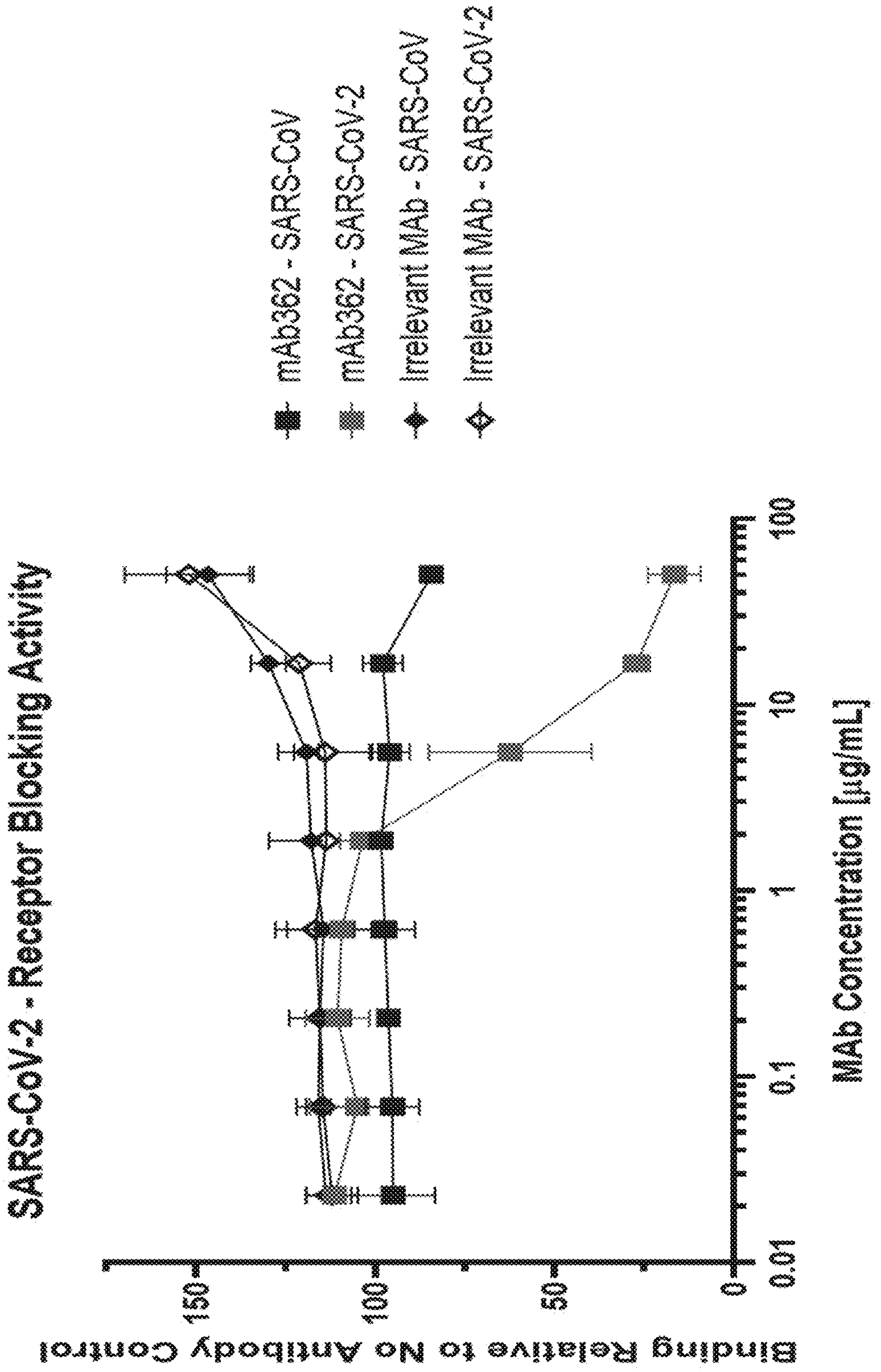
FIG. 3A is a graph depicting the concentration-dependent blocking activity of MAb362 against SARS-COV-2 binding to angiotensin-converting enzyme 2 (ACE2) receptor-expressing Vero cells.
Figure 3B:
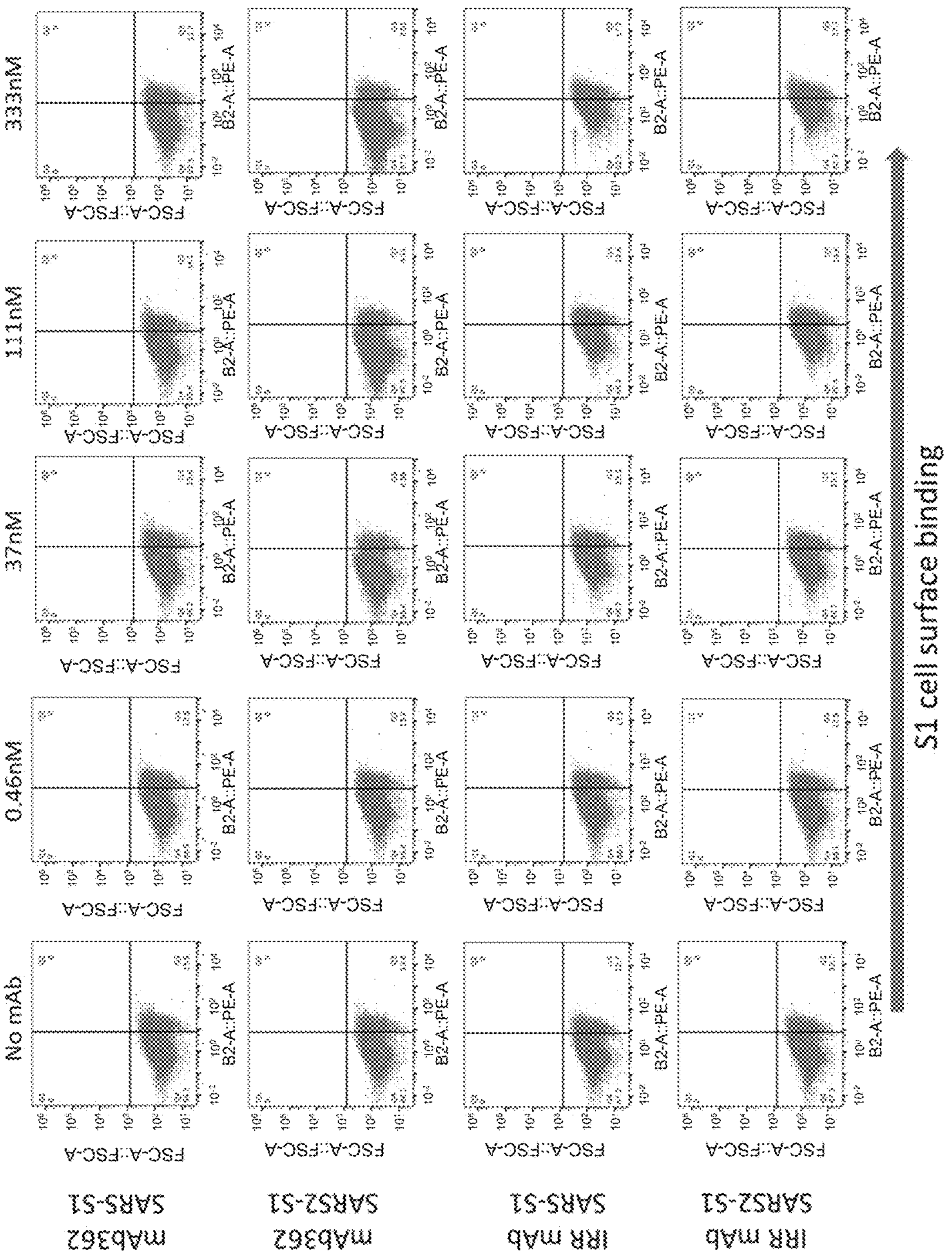
FIG. 3B is a set of plots depicting the concentration-dependent blocking activity of MAb362 against SARS-COV-2 binding to ACE2 receptor-expressing Vero cells.

Flow cytometry-based receptor binding inhibition assay was performed as described herein. MAb362 demonstrated concentration dependent binding to the RBD of the S protein SARS-COV-2, which competes with human ACE2 receptor binding to the RBD (FIGS. 3A and 3B). MAb362 was capable of inhibiting the binding of the ACE2 receptor to the RBD of SARS-COV-2 S protein by at least 83% at a concentration of 333 nM. Furthermore, MAb362 was capable of inhibiting the binding of the ACE2 receptor to the RBD of SARS-COV-2 S protein with an $EC_{50}$ of ~40 nM. This demonstrates that MAb362 can inhibit SARS-COV-2 binding to ACE2 receptor expression cells.

Example 5. Modeling MAb362 Binding to the Core Domain of SARS-COV and SARS-COV-2 S Protein RBD, and Identification of Key Epitope Residues by Mutagenesis Structure modeling of MAb362 binding to the core domain of RBD was performed as described in Example 1.

Figures 10A, 10B:
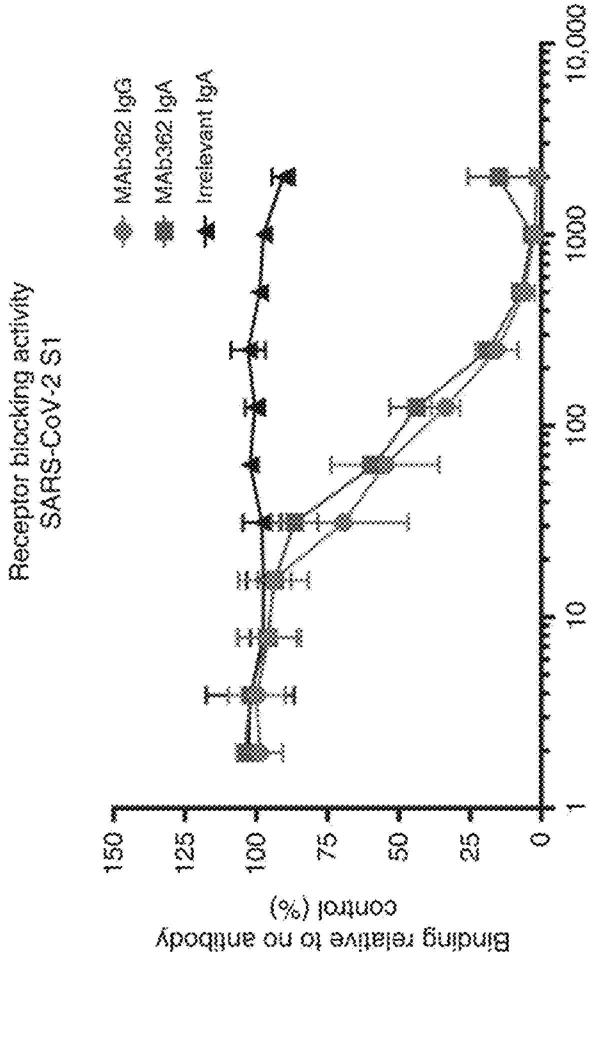
FIG. 10A is a graph depicting the concentration-dependent blocking activity of MAb362 IgG or IgA against SARS-COV-2 binding to ACE2 receptor-expressing Vero cells.
FIG. 10B is a table showing strength of binding to Mab362 and fold change relative to wild type for SARS-COV-2 S protein comprising the indicated mutations.
Figure 10D:
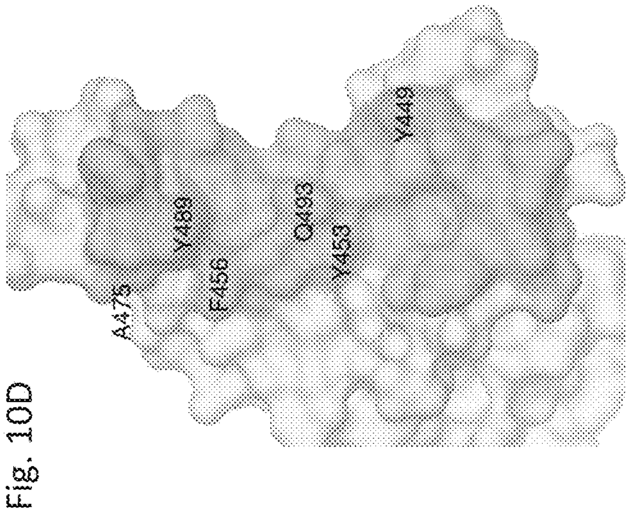
FIGS. 10C-10D are images of surface representations of a structural model depicting the binding domain of MAb362 and SARS-COV-2 S protein RBD.

To correlate the epitope binding with functionality, MAb362 IgG and IgA were tested in a receptor-blocking assay with Vero E6 cells. The result suggested that both MAb362 IgG and IgA block SARS-CoV-2 RBD binding to receptors in a concentration-dependent manner starting at ~30 nM (FIG. 10A). Mutational scanning with a combination of alanine (to introduce a loss of interaction), tryptophan (to introduce a steric challenge), and lysine to introduce charge mutations were performed to better delineate the binding surface (FIG. 10B).

The results showed that that key residues (Y449A, Y453A, F456A, A475W, Y489A, and Q493W) were critical for the complex and presumably, alterations in the packing caused marked loss of binding affinity (FIG. 10B). Among the tested mutants, A475W and Y489A also disrupted ACE2 binding (FIGS. 13A-13C). Interestingly, introduction of lysine mutations had little effect on binding, and some even showed enhanced binding, presumably owing to an overall more favorable charged interaction with the MAb362.

Figure 10C:
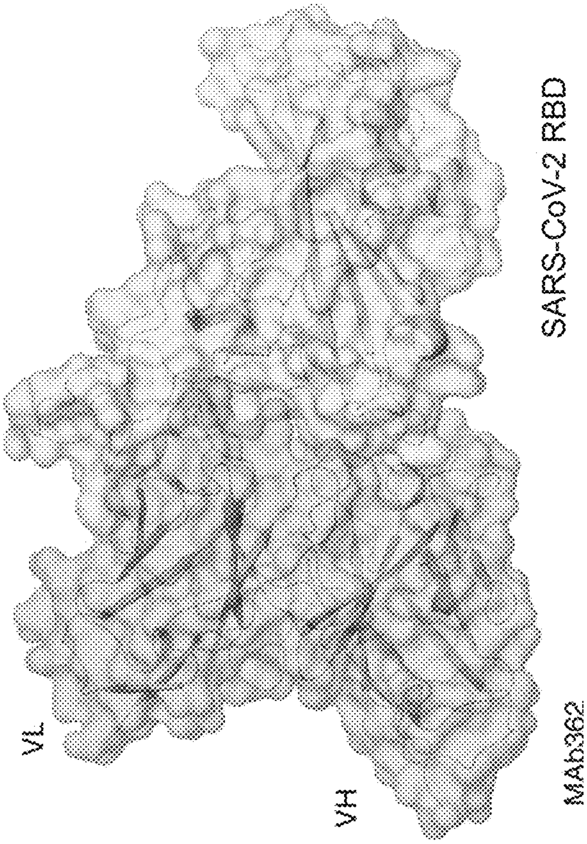

To better define the antibody-binding epitope, known co-crystal and cryo-electron microscopy complexes from SARS-COV and MERS spike protein in complex with neutralizing antibodies were evaluated for their potential to competitively block ACE2 binding, based on the structural interface of ACE2-SARS-COV-2-RBD (PDB ID-6VW1) (Shang et al., *Nature,* 581:221-224, 2020). The 80R-SARS-CoV-RBD complex (PDB ID-2GHW) (Hwang t al., *J. Biol. Chem.,* 281:34610-34616, 2006), a crystal structure of SARS-COV-RBD in complex with a neutralizing antibody, 80 R, was found most closely to have these characteristics. When the sequence was evaluated, it was ascertained that the two antibodies, MAb362 and 80 R, had frameworks with 90% amino-acid sequence identity. Thus, the crystal structure 2GHW provided a suitable scaffold to generate a homology model of MAb362. Protein-protein docking was performed using the Schrodinger suite with tethers based on the mutational analysis. The complex that satisfied the energetics and mutational data was then further interrogated with a 300 ns fully solvated molecular dynamics simulation in which the complex-structure remained stable after equilibration. The final frame of the simulation is the current model of the structure of the MAb362: SARS-CoV-2-RBD complex (FIG. 10C).

The interface of the complex is predicted to form an extensive interface (FIGS. 10D and 13A-13C) with the CDRs of both the heavy and light chains forming interactions with SARS-COV-2-RBD. Interestingly, the mutational analysis in combination with this model indicates that the light chain's contribution to this complex may be more significant than the heavy chain. Complementing the receptor-blocking assay and mutational analysis, our structural analysis further confirms that the MAb362 epitope is directly competing for the ACE2 binding epitope on SARS-COV-2 spike protein.

Figure 11A:
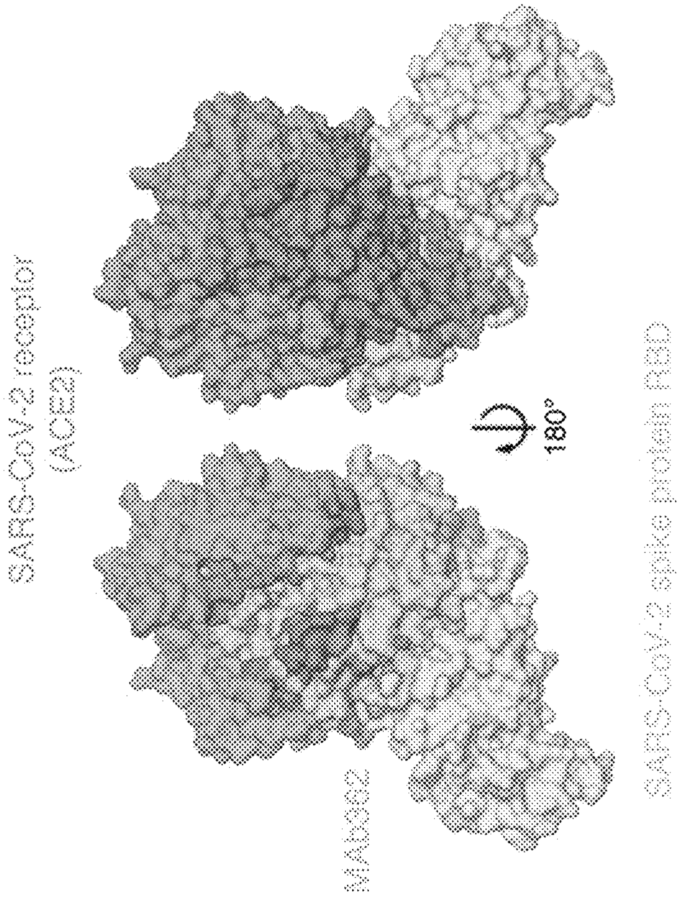
FIGS. 11A-11B are images of surface representations of a structural model depicting the binding of MAb362 to the receptor binding domain of SARS-COV-2 S protein.
Figure 11B:
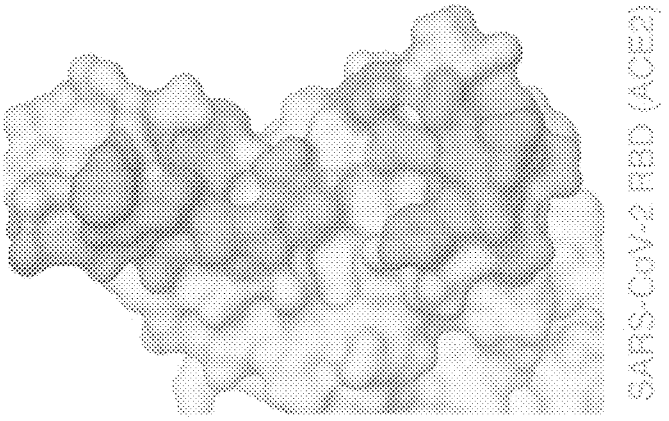
Figure 11C:
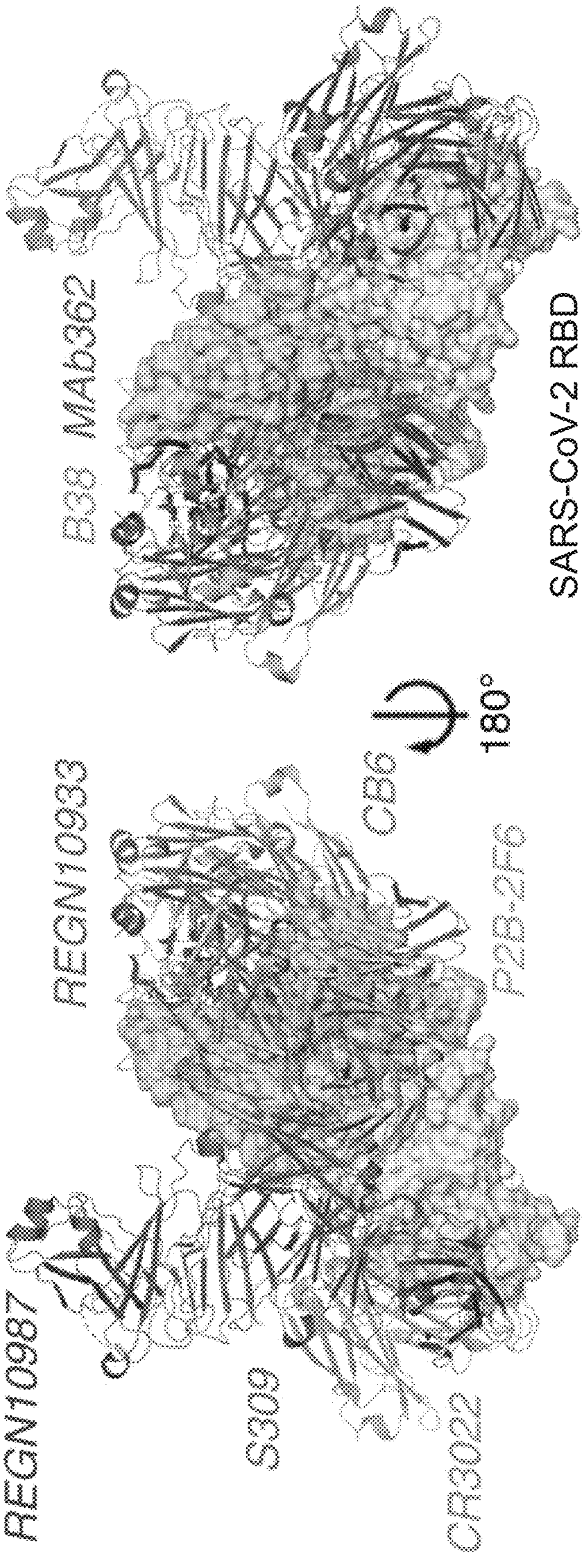
FIGS. 11C-11D are images of structural models depicting the binding of MAb362 to the receptor binding domain of SARS-COV-2 S protein.

The model of the structure of the MAb362: SARS-COV-2-RBD complex permitted the superposition of the ACE2: SARS-COV-2-RBD (PDB: 6VWI23) (FIG. 11A). MAb362 is predicted to overlap with the ACE2 epitope on the RBD. This interface of MAb362 (FIG. 10D) is very similar with the ACE2 interface projected onto the SARS-COV-2-RBD (FIG. 11B). However, this predicted epitope of MAb362 is different from the other recently reported MAb complexes to the SARS-COV-2-RBD (FIG. 11C), including: CR302217 (PDB: 6W41); S30916 (PDB: 6WPT); REGN10933 and REGN1098725; (PDB: 6XDG); P2B-2F626 (PDB: 7BWJ); CB627 (PDB: 7C01) and B3828 (PDB: 7BZ5). MAb362 is predicted to block ACE2-binding interface through a unique epitope conserved between SARS-COV and SARS-COV-2. This finding was consistent with the strong activity of MAb362 of compromising RBD-receptor interaction.

Figure 4B:
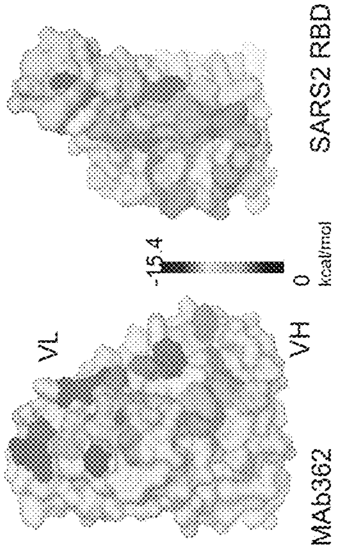
FIGS. 4A-4B are images of surface representations of a structural model depicting the binding domain of MAb362 and SARS-COV-2 S protein RBD.
Figure 4A:
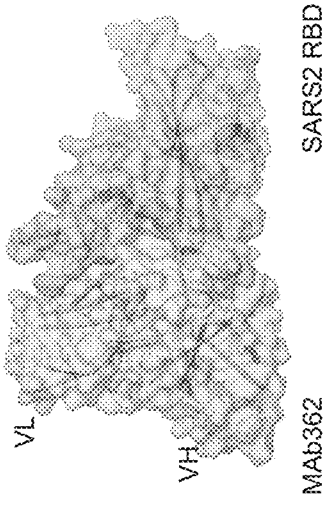
Figure 5A:
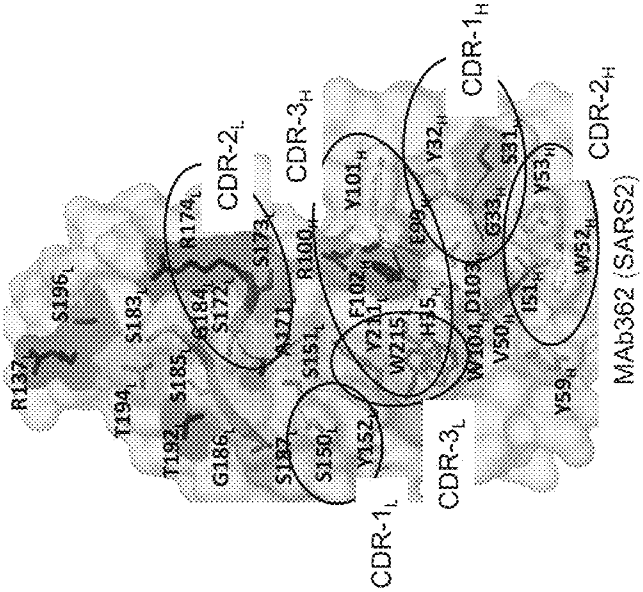
FIGS. 5A-5C are images of surface representations of the binding regions of MAb362 and SARS-CoV-2 S protein RBD.
Figure 5B:
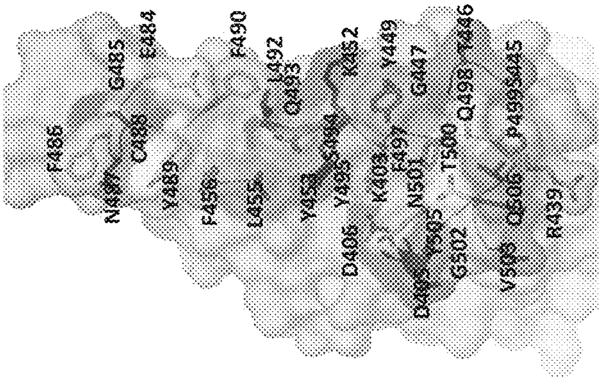
Figure 5C:
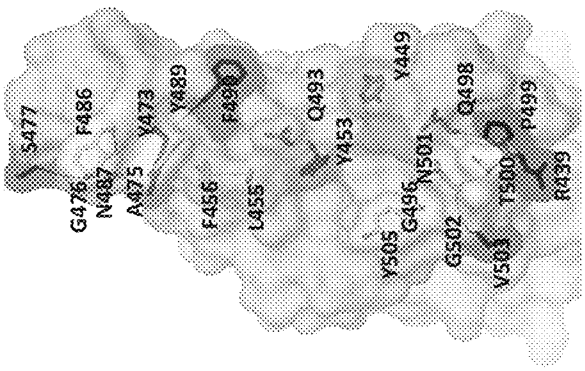
Figure 6A:
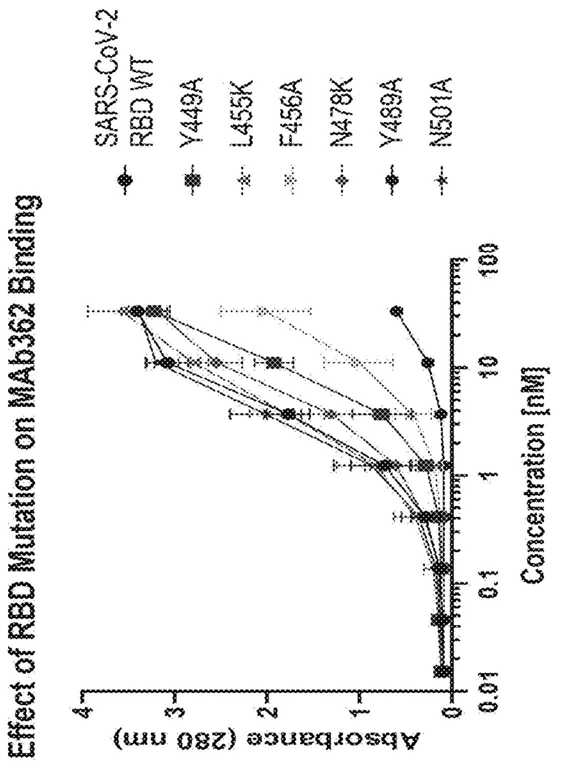
FIG. 6A is a graph depicting the effect of point mutations in SARS-COV-2 RBD on MAb362 binding to SARS-COV-2 S protein.
Figure 6B:
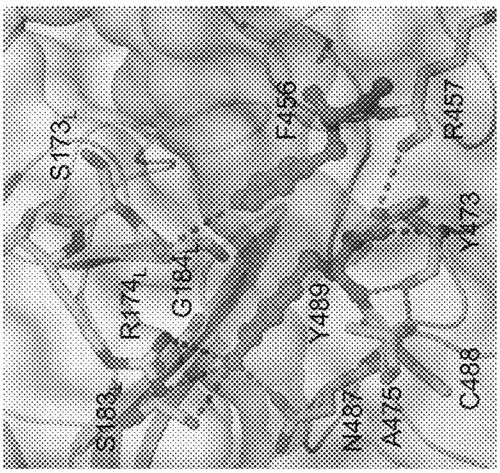
FIGS. 6B-6C are images showing the hydrogen bonding network within the key interaction interfaces between MAb362 and SARS-COV-2 RBD.
Figure 6C:
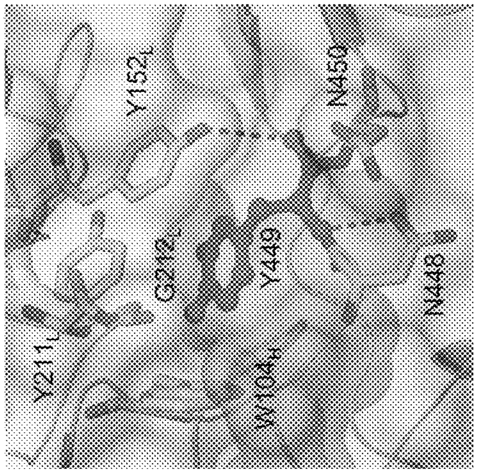
Figure 7A:
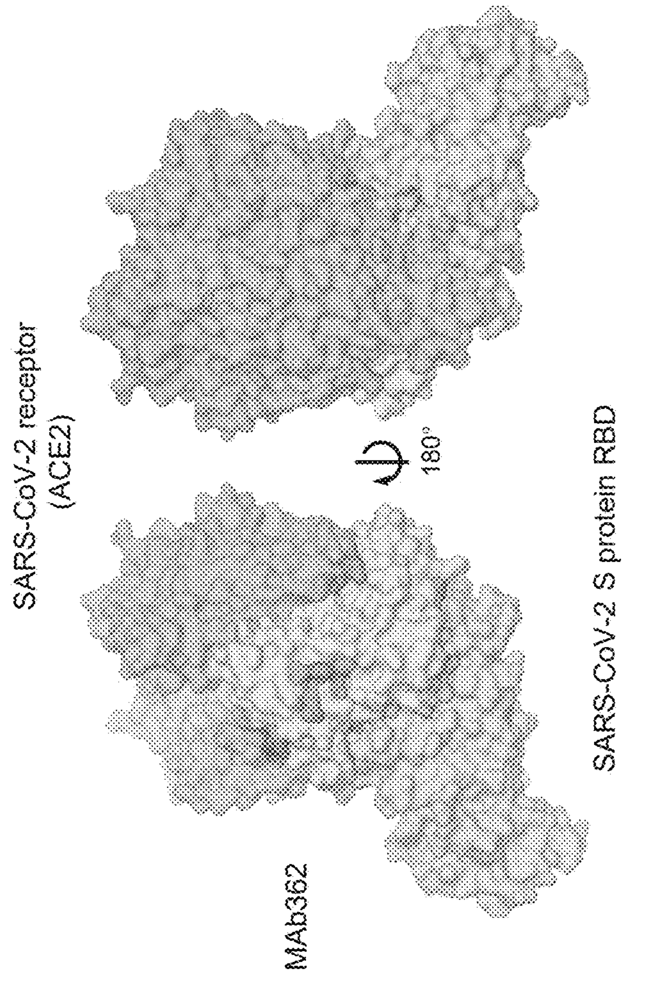
FIGS. 7A-7B are images of surface representations of a structural model depicting the binding of MAb362 to the receptor binding domain of SARS-COV-2 S protein.
Figure 7B:
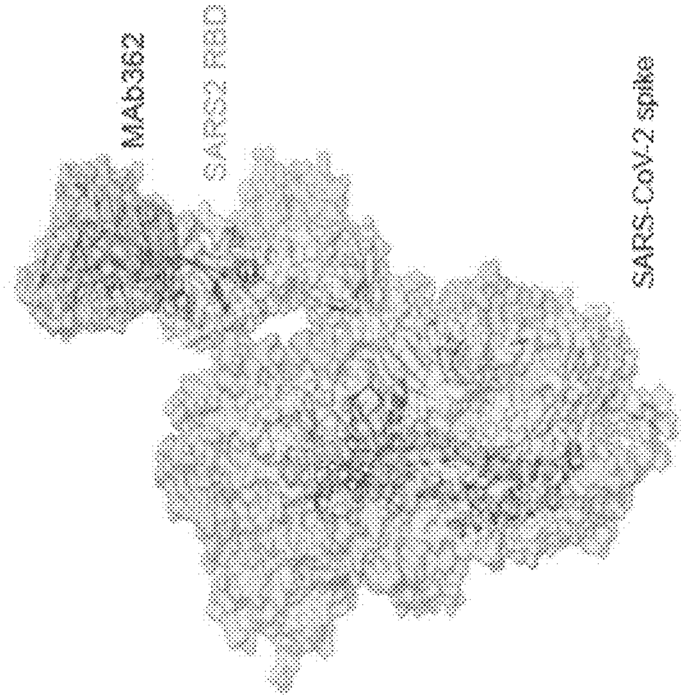
Figure 11D:
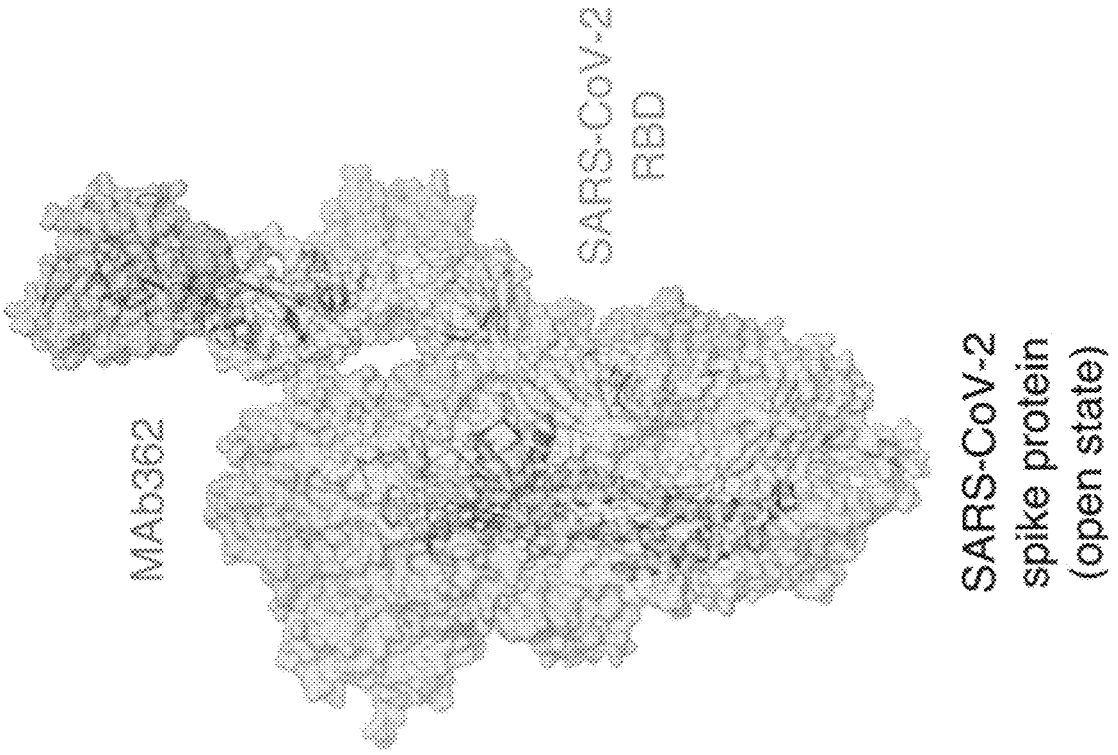

As with the binding of human ACE2, the MAb362 binding epitope would only be exposed if the RBD was in the open confirmation in the trimer (FIG. 11D). In the closed conformation, this epitope would not be accessible to MAb362 without major steric clashes. However, unlike CR3022 (Yuan et al. *Science.* 10.1126/science.abb7269 (2020)), MAb362 could access the epitope(s) when one or more of the trimers is in the open conformation, potentially accounting for its added neutralizing activity. Point mutations were engineered based on this model and the overlap with the hACE2-RBD binding interface further validated this model (FIGS. 4-6). The binding interface of MAb362 is predicted to overlap closely with major points of contact between ACE2 on the SARS-COV-2-RBD (FIGS. 7A-7B). Detailed examinations of these interactions suggested a few residues to be predicted to be extremely complementary. Mutagenesis at these sites showed that residues Y489, F456, and Y449 are important for MAb362 binding to the RBD core.

Figure 8B:
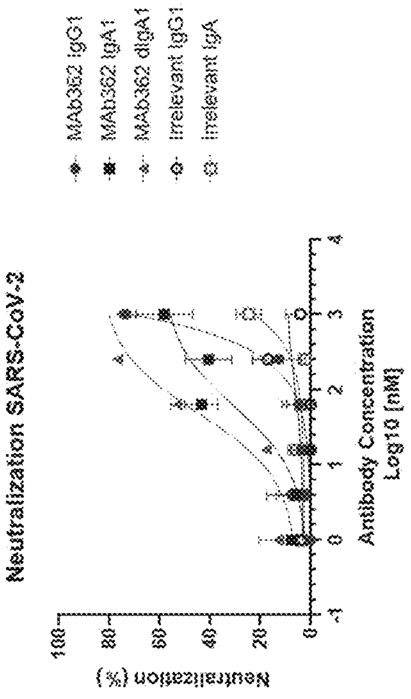
FIGS. 8A-8B are graphs depicting the neutralization of SARS-COV pseudovirus (FIG. 8A) and SARS-COV-2 pseudovirus (FIG. 8B) by MAb362.
Figure 8A:
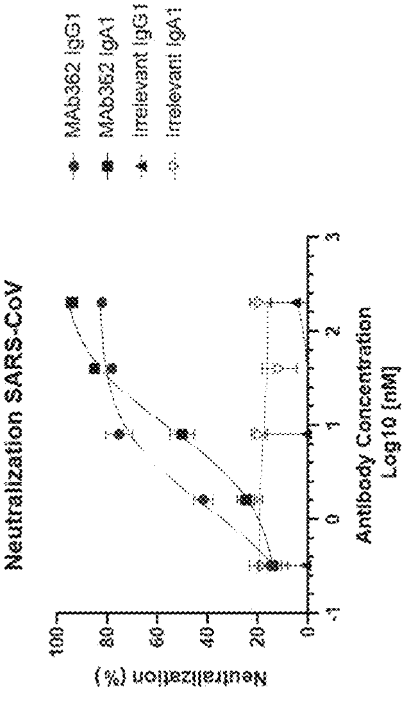
Figure 12A:
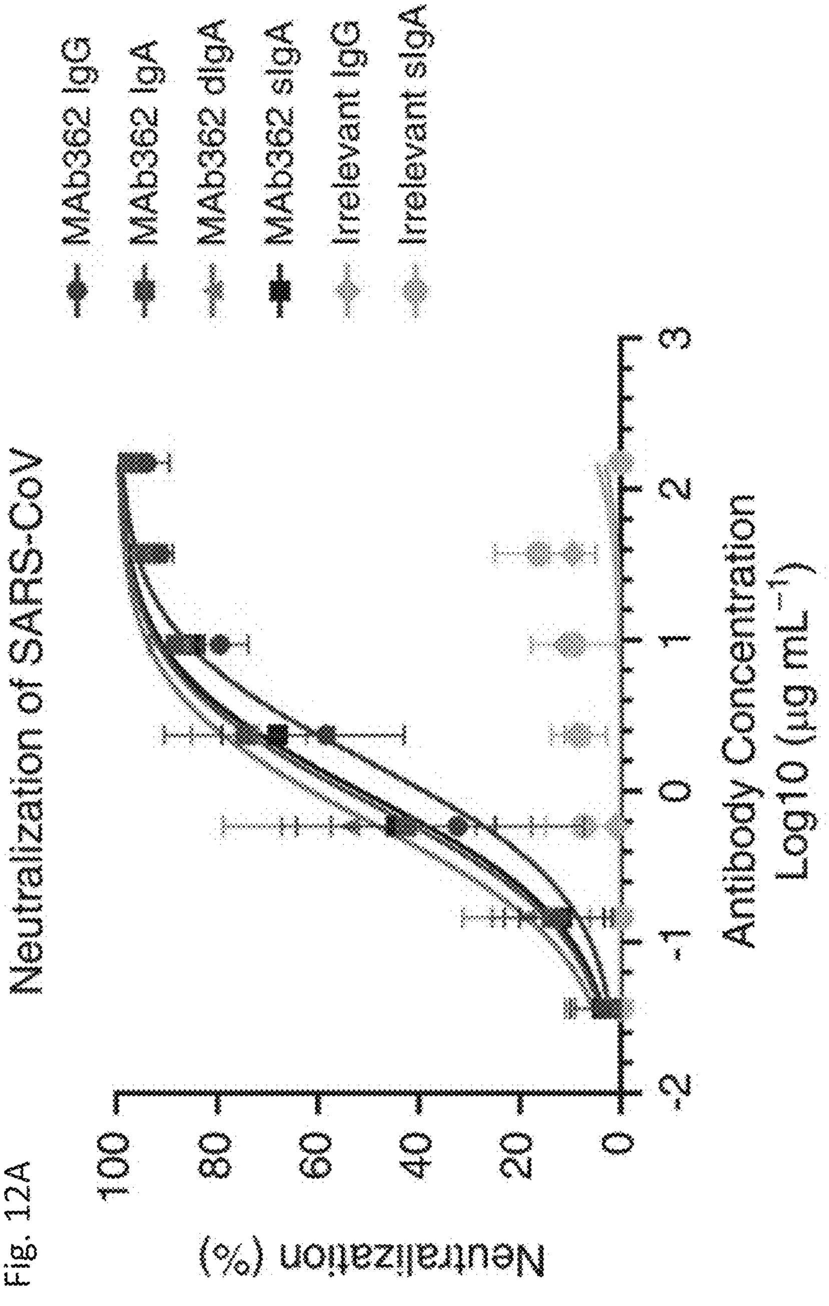
FIGS. 12A-12B are graphs depicting the neutralization of SARS-COV pseudovirus (FIG. 12A) and SARS-COV-2 pseudovirus (FIG. 12B) by MAb362 IgG, IgA, dimeric IgA (dIgA), and secretory IgA (sIgA).
Figure 12B:
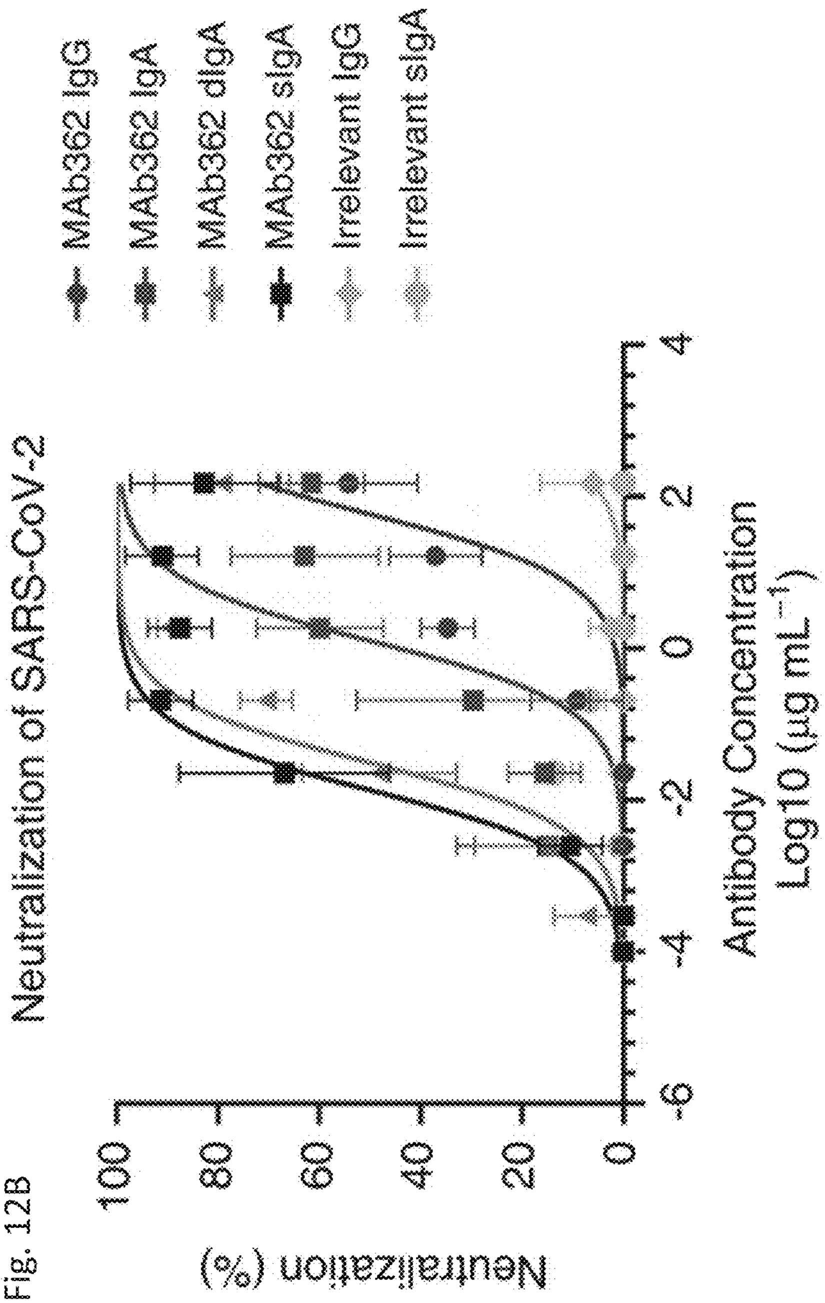

Example 6. MAb362 IgG, mIgA1, and dIgA1 Neutralize SARS-COV and SARS-COV-2 Pseudovirus To evaluate the neutralization potency of cross-reactive MAb362, a pseudovirus assay using lentiviral pseudovirions on 293T cells expressing ACE2 receptor (Ou et al., *Nat. Commun.* 11:1620, 2020) was performed. Both MAb362 IgG and IgA showed potent neutralization activity against SARS-CoV (FIGS. 8A and 12A). MAb362 IgG1 weakly neutralized SARS-COV-2 pseudovirus. Isotype switch to MAb362 IgA1 resulted in significantly enhanced neutralization potency, with an IC50 value of 1.26 μg $ml^{-1}$, compared to its IgG1 subclass variant ($IC_{50}$=58.67 μg $ml^{-1}$) (FIGS. 8B and 12B). Monomeric MAb362 IgA1 was also co-expressed with J chain to produce dimeric IgA (dIgA), which further improved neutralization with an EC50 close to 45 nM (FIG. 8B), and secretory component to produce secretory IgA (sIgA) (Giuntini et al., *Infect. Immun.,* 86: e00355-18, 2018). Both dIgA and sIgA were significantly more effective at neutralizing SARS-COV-2 pseudovirus with an IC50 of 30 ng $ml^{-1}$ and 10 ng $ml^{-1}$, respectively (FIG. 12B). Of note, all MAb362 IgG and IgA isotype variants showed comparable neutralization activity against SARS-COV (FIG. 12A).

Figure 12C:
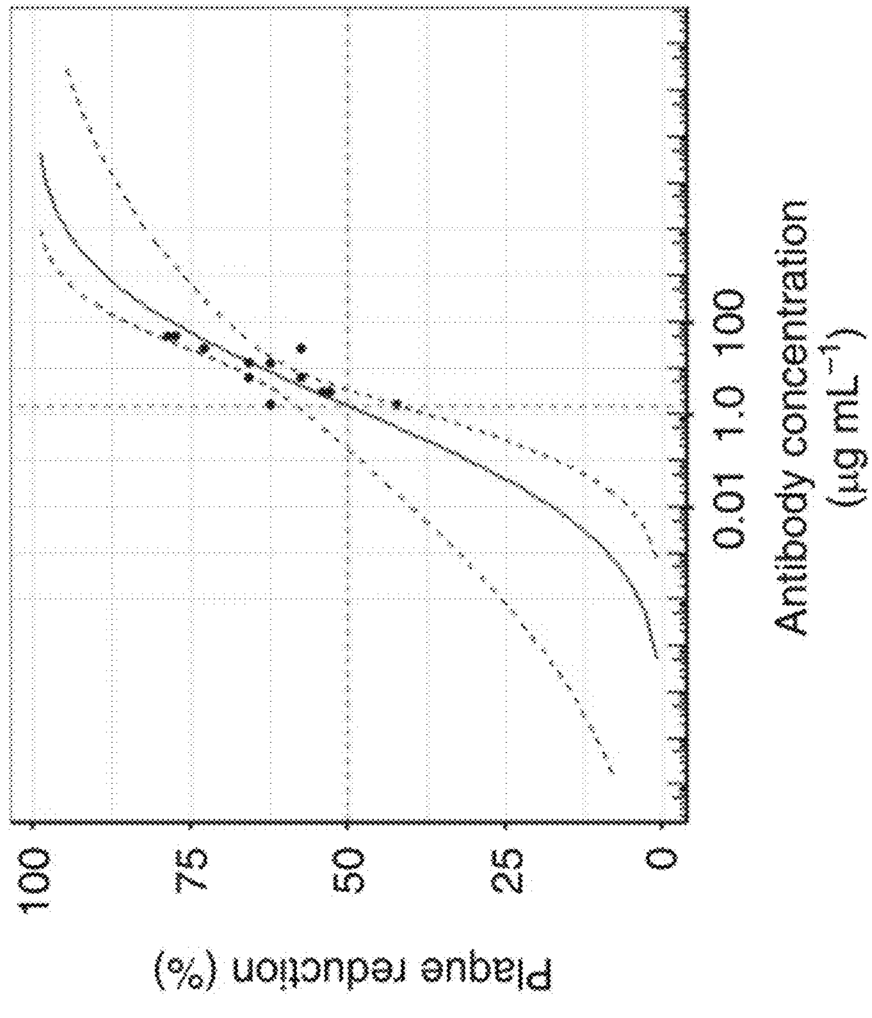
FIG. 12C is a graph showing results of a plaque reduction neutralization assay for SARS-COV-2 contacted with MAb362 IgG or Mab362 IgA.

Further, the most potent form MAb362 sIgA was tested in an authentic virus neutralization assay against SARS-COV-2. MAb362 sIgA neutralized SARS-COV-2 virus with an IC50 value of 9.54 μg $ml^{-1}$ (FIG. 12C). MAb362 IgG failed to neutralize live virus at the highest tested concentration. This is consistent with a prior study showing that isotype switch to IgA lead to improved antibody neutralization of HIV (Yu et al., *J. Immunol.,* 190:205-210, 2013). These data extend this observation to coronavirus, suggesting that IgA may play an important role in SARS-COV-2 neutralization.

Discussion

These results show a unique cross-reactive epitope within the core receptor-binding interface of the S protein of both SARS-COV and SARS-COV-2. MAb362 IgA neutralizes the virus by competing with S protein binding to ACE2 receptors. Interestingly, these results show that despite the same blocking of spike interaction with ACE2, MAb362 IgG weakly neutralizes SARS-COV-2, whereas IgA as monomer, dimer, or secretory antibody has significantly enhanced neutralization potency. These results suggest that compared with IgG, SARS-COV-2-specific IgA antibody may play an important independent role in providing protective mucosal immunity.

Other recent structure studies have characterized antibodies targeting the RBD domain distal from the receptor-binding core interface of SARS-COV-2 that lack the characteristics by which MAb362 interacts the ACE2 binding epitope. These neutralizing IgGs, 47D11 and 309, neutralize SARS-COV-2 with high potency, but do not block receptor binding to ACE2 (Pinto et al., Nature, 583:290-295, 2020; Wang et al., *Nat. Commun.,* 11:2251, 2020). Potentially, hACE2 may not be the sole receptor for SARS-CoV-2, similar to SARS COV (Jeffers et al., *Proc. Natl. Acad. Sci.,* 101:15748-15753, 2004), or these antibodies may prevent a conformational change necessary for viral entry.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated, monoclonal antibody that binds SARS-COV-2 spike(S) protein, wherein the antibody comprises the following complementarity determining regions (CDRs):

(a) a CDR-H1 comprising the amino acid sequence of GFSFSSYGMH (SEQ ID NO: 2);

(b) a CDR-H2 comprising the amino acid sequence of WYDGSDK (SEQ ID NO: 3);

(c) a CDR-H3 comprising the amino acid sequence of ARERYFDWIFDF (SEQ ID NO: 4);

(d) a CDR-L1 comprising the amino acid sequence of RASQSVSSSYLA (SEQ ID NO: 5);

(e) a CDR-L2 comprising the amino acid sequence of GASSRAT (SEQ ID NO:6); and (f) a CDR-L3 comprising the amino acid sequence of QQYGSSWT (SEQ ID NO: 7).

2. The antibody of claim 1, wherein the antibody comprises a heavy chain variable ($V_H$) domain comprising an amino acid sequence having at least 95% sequence identity to the amino acid sequence of SEQ ID NO: 16 and a light chain variable (VL) domain comprising an amino acid sequence having at least 95% sequence identity to the amino acid sequence of SEQ ID NO: 17.

3. The antibody of claim 1, wherein the antibody comprises a $V_H$ domain comprising the amino acid sequence of SEQ ID NO: 16 and a VL domain comprising the amino acid sequence of SEQ ID NO: 17.

4. The antibody of claim 1, wherein:

(a) the antibody binds SARS-COV-2 S protein with a $K_D$ of 300 μM or 13 nM; and/or (b) the antibody binds SARS-COV S protein with a $K_D$ of 1.3 nM or 1.4 nM.

5. The antibody of claim 1, wherein the antibody is a human antibody, an IgG class antibody, and/or an IgA class antibody.

6. The antibody of claim 5, wherein:

(a) the IgG class antibody is an IgG1 subclass antibody; or (b) the IgA class antibody is an IgA1 subclass antibody, an IgA2 subclass antibody, or a secretory IgA (sIgA).

7. The antibody of claim 1, wherein the antibody is an antibody fragment that binds SARS-COV-2 S protein selected from the group consisting of Fab, Fab', Fab'-SH, Fv, single chain variable fragment (scFv), and (Fab') 2 fragments.

8. An isolated nucleic acid encoding the antibody of claim 1.

9. A host cell comprising the nucleic acid of claim 8, wherein the host cell is a cultured host cell.

10. A method of producing an antibody that binds SARS-COV-2 S protein, the method comprising culturing a host cell comprising the nucleic acid of claim 8 in a culture medium.

11. A pharmaceutical composition comprising the antibody of claim 1 and a pharmaceutically acceptable carrier, excipient, or diluent.

12. A method of treating a subject having a SARS-COV-2 or SARS-COV infection, the method comprising administering to the subject an effective amount of an isolated, monoclonal antibody that binds SARS-COV-2 S protein, wherein the antibody comprises the following complementarity determining regions (CDRs):

(a) a CDR-H1 comprising the amino acid sequence of GFSFSSYGMH (SEQ ID NO: 2);
(b) a CDR-H2 comprising the amino acid sequence of WYDGSDK (SEQ ID NO: 3);
(c) a CDR-H3 comprising the amino acid sequence of ARERYFDWIFDF (SEQ ID NO: 4);
(d) a CDR-L1 comprising the amino acid sequence of RASQSVSSSYLA (SEQ ID NO: 5);
(e) a CDR-L2 comprising the amino acid sequence of GASSRAT (SEQ ID NO:6); and
(f) a CDR-L3 comprising the amino acid sequence of QQYGSSWT (SEQ ID NO: 7), thereby treating the subject.

13. The method of claim 12, wherein the antibody is administered to the subject as a combination therapy, wherein the combination therapy comprises administering to the subject one or more additional therapeutic agents.

14. A method of detecting a betacoronavirus in a sample from a subject, the method comprising contacting the sample with an isolated, monoclonal antibody that binds SARS-COV-2 S protein, wherein the antibody comprises the following complementarity determining regions (CDRs):

(a) a CDR-H1 comprising the amino acid sequence of GFSFSSYGMH (SEQ ID NO: 2);
(b) a CDR-H2 comprising the amino acid sequence of WYDGSDK (SEQ ID NO: 3);
(c) a CDR-H3 comprising the amino acid sequence of ARERYFDWIFDF (SEQ ID NO: 4);
(d) a CDR-L1 comprising the amino acid sequence of RASQSVSSSYLA (SEQ ID NO: 5);
(e) a CDR-L2 comprising the amino acid sequence of GASSRAT (SEQ ID NO:6); and
(f) a CDR-L3 comprising the amino acid sequence of QQYGSSWT (SEQ ID NO: 7), under conditions permissive for binding of the antibody to a betacoronavirus and detecting whether a complex is formed between the antibody and the betacoronavirus, wherein the betacoronavirus is SARS-COV-2 or SARS-COV.

15. A kit comprising the antibody of claim 1 and a package insert comprising instructions for using the antibody for treating a subject having a SARS-COV-2 or SARS-COV infection.

* * * * *